(12) United States Patent
Ebdrup et al.

(10) Patent No.: US 8,383,683 B2
(45) Date of Patent: Feb. 26, 2013

(54) PHARMACEUTICAL USE OF SUBSTITUTED AMIDES

(75) Inventors: Soren Ebdrup, Roskilde (DK); Henrik Sune Andersen, Lyngby (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 402 days.

(21) Appl. No.: 12/597,129

(22) PCT Filed: Apr. 10, 2008

(86) PCT No.: PCT/US2008/059903
§ 371 (c)(1),
(2), (4) Date: Oct. 22, 2009

(87) PCT Pub. No.: WO2008/134221
PCT Pub. Date: Nov. 6, 2008

(65) Prior Publication Data
US 2010/0087543 A1    Apr. 8, 2010

Related U.S. Application Data

(60) Provisional application No. 60/926,924, filed on Apr. 30, 2007.

(30) Foreign Application Priority Data

Apr. 24, 2007   (EP) ..................... 07106828

(51) Int. Cl.
*A61K 31/165*   (2006.01)
*C07C 233/91*   (2006.01)
*A61P 3/10*     (2006.01)

(52) U.S. Cl. ...................... 514/622; 564/182
(58) Field of Classification Search .................. 564/182; 514/622
See application file for complete search history.

(56) References Cited

U.S. PATENT DOCUMENTS

| | | |
|---|---|---|
| 2,913,454 A | 11/1959 | Petersen et al. |
| 3,723,442 A | 3/1973 | Nakanishi et al. |
| 3,784,551 A | 1/1974 | Nakanishi et al. |
| 4,350,696 A | 9/1982 | Cross et al. |
| 4,482,555 A | 11/1984 | Doria et al. |
| 4,851,423 A | 7/1989 | Girijavallabhan et al. |
| 4,963,590 A | 10/1990 | Backstrom et al. |
| 5,001,133 A | 3/1991 | Richardson et al. |
| 5,049,695 A | 9/1991 | Abraham et al. |
| 5,112,861 A | 5/1992 | Backstrom et al. |
| 5,122,539 A | 6/1992 | Abraham et al. |
| 5,169,850 A | 12/1992 | Dusza et al. |
| 5,225,402 A | 7/1993 | Ogawa et al. |
| 5,258,407 A | 11/1993 | Washburn et al. |
| 5,260,325 A | 11/1993 | Markwalder et al. |
| 5,272,167 A | 12/1993 | Girijavallabhan et al. |
| 5,274,104 A | 12/1993 | Arnaud et al. |
| 5,290,803 A | 3/1994 | Abraham et al. |
| 5,314,880 A | 5/1994 | Whittaker et al. |
| 5,356,904 A | 10/1994 | Freidinger et al. |
| 5,382,680 A | 1/1995 | Abraham et al. |
| 5,426,105 A | 6/1995 | Manning et al. |
| 5,432,191 A | 7/1995 | Abraham et al. |
| 5,436,254 A | 7/1995 | Ogawa et al. |
| 5,446,194 A | 8/1995 | Backstrom et al. |
| 5,459,144 A | 10/1995 | Girijavallabhan et al. |
| 5,585,394 A | 12/1996 | Di Malta et al. |
| 5,591,892 A | 1/1997 | Abraham et al. |
| 5,596,020 A | 1/1997 | Morris et al. |
| 5,602,137 A | 2/1997 | Ruhter et al. |
| 5,648,375 A | 7/1997 | Abraham et al. |
| 5,650,513 A | 7/1997 | Langhals et al. |
| 5,652,247 A | 7/1997 | Ogawa et al. |
| 5,674,879 A | 10/1997 | Manning et al. |
| 5,677,330 A | 10/1997 | Abraham et al. |
| 5,705,521 A | 1/1998 | Abraham et al. |
| 5,731,454 A | 3/1998 | Abraham et al. |
| 5,750,532 A | 5/1998 | Girijavallabhan et al. |
| 5,786,379 A | 7/1998 | Bernardon |
| 5,795,907 A | 8/1998 | Kalindjian et al. |
| 5,872,282 A | 2/1999 | Abraham et al. |
| 5,912,260 A | 6/1999 | Kalindjian et al. |
| 5,919,829 A | 7/1999 | Kalindjian et al. |
| 5,927,283 A | 7/1999 | Abraham et al. |
| 5,932,569 A | 8/1999 | Janssens et al. |
| 5,939,437 A | 8/1999 | Kalindjian et al. |
| 6,001,879 A | 12/1999 | Seitz et al. |

(Continued)

FOREIGN PATENT DOCUMENTS

| | | |
|---|---|---|
| CN | 1736485 | 2/2006 |
| DE | 4338784 | 5/1995 |

(Continued)

OTHER PUBLICATIONS

Andrew et al., J. Clin. Endocrinol. Metab. vol. 87, pp. 277-285 (2002).
Andrews et al., J. Clin. Endocrinol. Metab. vol. 88, pp. 285-291 (2003).
Barf T et al: "Recent progress in 11-[beta]-hydroxysteroid dehydrogenase type 1 (11-[beta]-HSD1) inhibitor development" Drugs of the Future 2006 Spain, vol. 31, No. 3, Mar. 2006, pp. 231-243.
Bird et al., J. Physiology vol. 585, pp. 187-201 (2007).
Brem et al., Hypertension vol. 31, pp. 459-462 (1998).

(Continued)

*Primary Examiner* — Niloofar Rahmani
(74) *Attorney, Agent, or Firm* — Samuel B. Rollins

(57) ABSTRACT

The use of substituted amides for modulating the activity of 11β-hydroxysteroid dehydro-genase type 1 (11βHSD1) and the use of these compounds as pharmaceutical composi-tions, are described. Also a novel class of substituted amides, their use in therapy, phar-maceutical compositions comprising the compounds, as well as their use in the manufac-ture of medi-caments are described. The present compounds are modula-tors and more specifically inhibitors of the activity of 11βHSD1 and may be useful in the treatment of a range of medical disorders where a decreased intracellular concentra-tion of active gluco-corticoid is desirable.

6 Claims, No Drawings

U.S. PATENT DOCUMENTS

| | | |
|---|---|---|
| 6,096,736 A | 8/2000 | Ogawa et al. |
| 6,124,289 A | 9/2000 | He et al. |
| 6,458,803 B1 | 10/2002 | Sikorski et al. |
| 6,506,783 B1 | 1/2003 | Camden |
| 6,521,641 B1 | 2/2003 | Klein et al. |
| 6,548,549 B1 | 4/2003 | Seitz et al. |
| 6,613,803 B1 | 9/2003 | Wang et al. |
| 6,638,947 B2 | 10/2003 | Wang et al. |
| 6,696,442 B2 | 2/2004 | Wang et al. |
| 6,833,371 B2 | 12/2004 | Atkinson et al. |
| 7,129,242 B2 | 10/2006 | Satoh et al. |
| 7,157,490 B2 | 1/2007 | Colandrea et al. |
| 7,186,735 B2 | 3/2007 | Strobel et al. |
| 7,265,122 B2 | 9/2007 | Wu et al. |
| 7,358,238 B2 | 4/2008 | Andersen et al. |
| 7,501,405 B2 | 3/2009 | Kampen et al. |
| 7,557,110 B2 | 7/2009 | Kataoka et al. |
| 7,700,583 B2 | 4/2010 | Gundertofte et al. |
| 7,723,323 B2 | 5/2010 | Andersen et al. |
| 2002/0006932 A1 | 1/2002 | Galley et al. |
| 2002/115671 A1 | 8/2002 | Goehring |
| 2003/0144256 A1 | 7/2003 | Klein et al. |
| 2004/0142922 A1 | 7/2004 | Alanine et al. |
| 2004/0186102 A1 | 9/2004 | Wu et al. |
| 2005/0009871 A1 | 1/2005 | Ramesh et al. |
| 2005/0054850 A1 | 3/2005 | Wu et al. |
| 2005/0080087 A1 | 4/2005 | Pendri et al. |
| 2005/0154202 A1 | 7/2005 | Hagmann et al. |
| 2005/0261302 A1 | 11/2005 | Hoff et al. |
| 2006/0009918 A1 | 1/2006 | Mallik et al. |
| 2006/0079506 A1 | 4/2006 | Linders et al. |
| 2006/0094699 A1 | 5/2006 | Kampen et al. |
| 2006/0111366 A1 | 5/2006 | Andersen et al. |
| 2006/0149070 A1 | 7/2006 | Rohde et al. |
| 2006/0281773 A1 | 12/2006 | Patel et al. |
| 2007/0054882 A1 | 3/2007 | Klein et al. |
| 2007/0270408 A1 | 11/2007 | Andersen et al. |
| 2008/0108598 A1 | 5/2008 | Andersen et al. |
| 2009/0105289 A1 | 4/2009 | Kilburn et al. |
| 2009/0118259 A1 | 5/2009 | Kilburn et al. |
| 2009/0124598 A1 | 5/2009 | Andersen et al. |
| 2009/0137574 A1 | 5/2009 | Kampen et al. |
| 2009/0264412 A1 | 10/2009 | Kampen et al. |
| 2009/0264414 A1 | 10/2009 | Andersen et al. |
| 2009/0306048 A1 | 12/2009 | Kilburn et al. |
| 2009/0325932 A1 | 12/2009 | Ebdrup et al. |
| 2010/0056600 A1 | 3/2010 | Ebdrup et al. |
| 2010/0076041 A1 | 3/2010 | Kilburn et al. |
| 2010/0120743 A1 | 5/2010 | Gundertofte et al. |
| 2010/0137377 A1 | 6/2010 | Petersen et al. |
| 2010/0168083 A1 | 7/2010 | Ebdrup |
| 2010/0197658 A1 | 8/2010 | Andersen et al. |
| 2010/0292215 A1 | 11/2010 | Ebdrup et al. |
| 2010/0331366 A1 | 12/2010 | Ebdrup |
| 2011/0003852 A1 | 1/2011 | Ebdrup |
| 2011/0003856 A1 | 1/2011 | Ebdrup |
| 2011/0039853 A1 | 2/2011 | Ebdrup |
| 2011/0224244 A1 | 9/2011 | Polisetti et al. |

FOREIGN PATENT DOCUMENTS

| | | |
|---|---|---|
| FR | 2456731 | 12/1980 |
| GB | 825514 | 11/1956 |
| JP | 08-048662 | 2/1996 |
| JP | 09-221476 | 8/1997 |
| JP | 11-152269 | 6/1999 |
| JP | 2001 139574 | 5/2001 |
| JP | 2003-286171 | 10/2003 |
| JP | 2007-231005 | 9/2007 |
| WO | WO 94/01113 | 1/1994 |
| WO | WO 94/18193 | 8/1994 |
| WO | WO 97/07789 | 3/1997 |
| WO | WO 97/22588 | 6/1997 |
| WO | WO 97/24328 | 7/1997 |
| WO | WO 98/46559 | 10/1998 |
| WO | WO 99/30699 | 6/1999 |
| WO | WO 99/61013 | 12/1999 |
| WO | WO 00/12074 | 3/2000 |
| WO | WO 00/46197 | 8/2000 |
| WO | WO 00/47558 | 8/2000 |
| WO | WO 00/63165 | 10/2000 |
| WO | WO 00/73283 | 12/2000 |
| WO | WO 01/02385 | 1/2001 |
| WO | WO 01/22969 | 4/2001 |
| WO | WO 01/32621 | 5/2001 |
| WO | WO 01/44213 | 6/2001 |
| WO | WO 01/64676 | 9/2001 |
| WO | WO 01/90090 | 11/2001 |
| WO | WO 01/90091 | 11/2001 |
| WO | WO 01/90092 | 11/2001 |
| WO | WO 01/90093 | 11/2001 |
| WO | WO 01/90094 | 11/2001 |
| WO | WO 02/00626 | 1/2002 |
| WO | WO 02/02797 | 1/2002 |
| WO | WO 02/10191 | 2/2002 |
| WO | WO 02/072084 | 9/2002 |
| WO | WO 02/076435 | 10/2002 |
| WO | WO 02/089781 | 11/2002 |
| WO | WO 02/094799 | 11/2002 |
| WO | WO 02/100819 | 12/2002 |
| WO | WO 03/000649 | 1/2003 |
| WO | WO 03/028641 | 4/2003 |
| WO | WO 03/028730 | 4/2003 |
| WO | WO 03/029245 | 5/2003 |
| WO | WO 03/037274 | 5/2003 |
| WO | WO 03/037900 | 5/2003 |
| WO | WO 03/065983 | 8/2003 |
| WO | WO 03/070732 | 8/2003 |
| WO | WO 03/086410 | 10/2003 |
| WO | WO 2004/024896 | 3/2004 |
| WO | WO 2004/024897 | 3/2004 |
| WO | WO 2004/033427 | 4/2004 |
| WO | WO 2004/052461 | 6/2004 |
| WO | WO 2004/056744 | 7/2004 |
| WO | WO 2004/056745 | 7/2004 |
| WO | WO 2006/044645 | 7/2004 |
| WO | WO 2004/065351 | 8/2004 |
| WO | WO 2004/075823 | 9/2004 |
| WO | 2004089470 | * 10/2004 |
| WO | WO 2004/087159 | 10/2004 |
| WO | WO 2004/089380 | 10/2004 |
| WO | WO 2004/089415 | 10/2004 |
| WO | WO 2004/089416 | 10/2004 |
| WO | WO 2004/089470 | 10/2004 |
| WO | WO 2004/089471 | 10/2004 |
| WO | WO 2004/089896 | 10/2004 |
| WO | WO 2004/091610 | 10/2004 |
| WO | WO 2005/013950 | 2/2005 |
| WO | WO 2005/028438 | 3/2005 |
| WO | WO 2005/032484 | 4/2005 |
| WO | WO 2005/035534 | 4/2005 |
| WO | WO 2005/085202 | 9/2005 |
| WO | WO 2005/095397 | 10/2005 |
| WO | WO 2005/115975 | 12/2005 |
| WO | WO 2006/009835 | 1/2006 |
| WO | WO 2006/014012 | 2/2006 |
| WO | WO 2006/024627 | 3/2006 |
| WO | WO 2006/028958 | 3/2006 |
| WO | WO 2006/040329 | 4/2006 |
| WO | WO 2006/048330 | 5/2006 |
| WO | WO 2006/055752 | 5/2006 |
| WO | WO 2006/074244 | 7/2006 |
| WO | WO 2006/074330 | 7/2006 |
| WO | WO 2006/094633 | 9/2006 |
| WO | WO 2006/105127 | 10/2006 |
| WO | WO 2006/113261 | 10/2006 |
| WO | WO 2006/136402 | 12/2006 |
| WO | WO 2007/046001 | 4/2007 |
| WO | WO 2007/051810 | 5/2007 |
| WO | WO 2007/051811 | 5/2007 |
| WO | WO 2007/058960 | 5/2007 |
| WO | WO 2007/059905 | 5/2007 |
| WO | WO 2007/066784 | 6/2007 |
| WO | WO 2007/107550 | 9/2007 |
| WO | WO 2007/109160 | 9/2007 |
| WO | WO 2007/115935 | 10/2007 |
| WO | WO 2007/144394 | 12/2007 |

| | | |
|---|---|---|
| WO | WO 2008/002244 | 1/2008 |
| WO | WO 2008/006702 | 1/2008 |
| WO | WO 2008/006703 | 1/2008 |
| WO | WO 2008/101885 | 8/2008 |
| WO | WO 2008/101886 | 8/2008 |
| WO | WO 2008/101907 | 8/2008 |
| WO | WO 2008/101914 | 8/2008 |
| WO | WO 2008/110196 | 9/2008 |
| WO | WO 2008/119017 | 10/2008 |
| WO | WO 2008/127924 | 10/2008 |
| WO | WO 2009/126863 | 10/2009 |
| WO | WO 2010/057126 | 5/2010 |
| WO | WO 2010/059618 | 5/2010 |

OTHER PUBLICATIONS

Brindley et al., Progress Lipid Res. vol. 30, pp. 349-360 (1991).
Bujalska et al., Endocrinology vol. 140, pp. 3188-3196 (1999).
Carruthers et al., J. Chem. Soc. Perkin Trans. 1 vol. 10, pp. 2854-2856 (1990).
Cooper et al., Bone vol. 27, pp. 375-381 (2000).
Coppola, Gary M. et al., "Perhydroquinolylbenzamides as Novel Inhibitors of 11.beta.-Hydroxysteroid Dehydrogenase Type 1" Journal of Medicinal Chemistry, 48 (21), 6696-6712 Coden: Jmcmar; ISSN: 0022-2623, 2005.
Davani et al., J. Biol. Chem. vol. 275, pp. 34841-34844 (2000).
Demchenko, Chem. Hetero. Comp. vol. 36, pp. 985-988 (2000).
Desai et al., Tetrahedron Lett. vol. 34, pp. 7685-7688 (1993).
Donohue et al., J. Comb. Chem. vol. 4, pp. 23-32 (2002).
Evans et al., J. Med. Chem. vol. 35, pp. 3919-3927 (1992).
Fotsch C. et al., "11[beta]-Hydroxysteroid dehydrogenase-1 as a therapeutic target for metabolic diseases" Expert Opinion on Therapeutic Patents, Ashley Publications, GB, vol. 15, No. 3, 2005, pp. 289-303.
Ganguly A.K. et al.; "Sythesis of heterocyclic compounds using radical reactions" Tetrahedron Letters, Elsevier, Amsterdam, NL, vol. 43, No. 38, Sep. 16, 2002, pp. 6865-6868.
Giacomelli et al. Eur. J. Org. Chem. vol. 3, pp. 537-541 (2003).
Hashigaki et al., Chem. Pharm. Bull. vol. 32, pp. 3561-3568 (1984).
Hosfield et al., J. Biol. Chem. vol. 280, pp. 4639-4648 (2005).
Ignatova et al., American Journal of Physiology—Endocrinology and Metabolism, 296(2):E367-E377 (2009).
Johnson et al., J. Org. Chem. vol. 35, pp. 622-626 (1970).
Kondo, Kazumi et al: "Characterization of Orally Active Nonpeptide Vasopressin V2 Receptor Agonist" Journal of Medicinal Chemistry, vol. 45, No. 17, 2002, pp. 3805-3808.
Kondo, Kazumi et al: "Novel Design of Nonpeptide AVP V2 Receptor Agonists: Structural Requirements for and Agonist Having 1-(4-Aminobenzoyl)-2,3,4,5,-tetrahydro-1H-1-benezazepine as a Template" Journal of Medicinal Chemistry, vol. 43, No. 23, 2000, pp. 4388-4397.
Koteletsev et al., Proc. Nat'l Acad. Sci. vol. 94, pp. 14924-14929 (1997).
Leyendecker et al., Nouveau J. de Chimie vol. 9, pp. 13-19 (1985).
Mariani et al., Farmaco vol. 38, pp. 653-663 (1983).
Massa et al., J. Heterocycl. Chem. vol. 27, pp. 1805-1808 (1990).
Masuzaki et al., J. Clin. Invest. vol. 112, pp. 83-90 (2003).
Masuzaki et al., Science vol. 294, pp. 2166-2170 (2001).
McCullough et al., J. Chem. Soc. Perkin Trans. 1 vol. 20, pp. 2553-2560 (1996).
Moisan et al., Endocrinology, vol. 127, pp. 1450-1455 (1990).
Morton et al., J. Biol. Chem. vol. 276, pp. 41293-41300 (2001).
Nankervis et al.: "Calcium sensitizazion as a positive inotropic mechanism . . . " Journal of Cardiovascular Pharmacology, vol. 24, No. 4, 1994, pp. 612-617.
Nieczypor et al., Eu. J. Org. Chem. vol. 2004, pp. 812-819 (2004).
PCT International Preliminary Report on Patentability for Application No. PCT/US2008/059903 dated Nov. 5, 2009.
PCT International Search Report for Application No. PCT/US2008/059903 dated Jul. 25, 2008.
PCT Written Opinion for Application No. PCT/US2008/059903 dated Jul. 25, 2008.
Pending Claims for U.S. Appl. No. 11/665,103, filed Mar. 24, 2011.
Pending Claims for U.S. Appl. No. 12/092,223, filed Mar. 24, 2011.
Pending Claims for U.S. Appl. No. 12/092,230, filed Mar. 25, 2011.
Pending Claims for U.S. Appl. No. 12/293,709, filed Mar. 25, 2011.
Pending Claims for U.S. Appl. No. 12/294,475, filed Jul. 18, 2011.
Pending Claims for U.S. Appl. No. 12/304,501, filed Mar. 25, 2011.
Pending Claims for U.S. Appl. No. 12/307,999, filed May 23, 2011.
Pending Claims for U.S. Appl. No. 12/308,000, filed Mar. 28, 2011.
Pending Claims for U.S. Appl. No. 12/528,227, filed Mar. 28, 2011.
Pending Claims for U.S. Appl. No. 12/528,229, filed Mar. 29, 2011.
Pending Claims for U.S. Appl. No. 12/528,231, filed Mar. 28, 2011.
Pending Claims for U.S. Appl. No. 12/528,233, filed Mar. 29, 2011.
Pending Claims for U.S. Appl. No. 12/529,956, filed Mar. 29, 2011.
Pending Claims for U.S. Appl. No. 12/593,456, filed Mar. 29, 2011.
Pending Claims for U.S. Appl. No. 12/595,310, filed Mar. 29, 2011.
Pending Claims for U.S. Appl. No. 13/078,221, filed Apr. 1, 2011.
Pending Claims for U.S. Appl. No. 13/220,843, filed Aug. 30, 2011.
Rauz et al., Invest. Opthalmol. Vis. Sci. vol. 42, pp. 2037-2042 (2001).
Reed et al., Scand. J. Gastroentreol. vol. 15, pp. 51-56 (1980).
Schwartz et al., Nature vol. 404, pp. 661-671 (2000).
Seefelter et al., Chemische Berichte vol. 96, pp. 3243-3253 (1963).
Skowronska-Ptasinska et al: "Effect of Different Dialkylamino Groups on the Regioselectivity of Lithiation of 0-Protected 3-(Dialkylamino)phenols" Journal of Organic Chemistry, vol. 50, No. 15, 1985, pp. 2690-2698.
Sohar R et al: "Conformational Analysis of N-Acylazabycyclooctanes," Magnetic Resonance in Chemistry, John Wiley, Chichester, GB, vol. 23, No. 7, Jan. 1, 1985, pp. 506-513.
Souness et al., Steroids vol. 67, pp. 195-201 (2002).
Tabuchi, S. et al.: "Novel Potent Antagonists of Human Neuropeptide Y Y5 Receptor. Part 1:2-Oxobenzothiazolin-3-acetic Acid Derivatives" Bioorganic & Medicinal Chemistry Letters, vol. 12, 2002, pp. 1171-1175.
Tannin et al., J. Biol. Chem. vol. 266, pp. 16653-16658 (1991).
Tomlinson et al., J. Clin. Endocrinol. Metab. vol. 87, pp. 57-62 (2002).
Villani, F.J. et al.; "Derivatives of 2-Azabicyclo[2.2.2]octane" Journal of Medicinal Chemistry, 1966, pp. 264-265.
Walker et al., J. Clin. Endocrinol. Metab. vol. 80, pp. 3155-3159 (1995).
Whitworth et al., J. Hypertens. vol. 20, pp. 1035-1043 (2002).
Whorwood et al., J. Clin. Endocrinol. Metab. vol. 86, pp. 2296-2308 (2001).
Willoughby C A et al: "Solid Phase Synthesis of Aryl Amines" Tetrahedron Letters, Elsevier, Amsterdam, NL, vol. 37, No. 40, Sep. 30, 1996, pp. 7181-7184 XP004030858 ISSN: 0040-4039 table 2; compound 1.
Wu et al., Toxicology vol. 236, pp. 1-6 (2007).
Yang et al., Bioorg. Med. Chem. Lett. vol. 8, pp. 107-112 (1998).
Yau et al., Proc. Nat'l Acad. Sci. vol. 98, pp. 4716-4721 (2001).
Yudt et al., Mol. Endocrinol. vol. 16, pp. 1719-1726 (2002).
Office Action mailed Nov. 8, 2011 for Taiwanese Patent Application No. 097114965.
Restriction Requirement dated Jan. 27, 2012 for U.S. Appl. No. 12/595,310.
European Search Report for European Patent Application No. 08745501.0 dated Apr. 6, 2011.
Patel et al., "Discovery of Adamantane Ethers as Inhibitors of 11beta-HSD-1: Synthesis and Biological Evaluation", Bioorganic & Medicinal Chemistry Letters, 17(3):750-755 (2007).
Office Action for U.S. Appl. No. 13/128,045 dated Sep. 26, 2012.
Rauz et al., "Inhibition of 11beta-hydroxysteroid dehydrogenase type 1 lowers intraocular pressure in patients with ocular hypertension" Q. J. Med., 96:481-490 (2003).
Tomlinson, et al., "11beta-Hydroxysteroid Dehydrogenase Type 1: A Tissue-Specific Regulator of Glucocorticoid Response," Endocrine Reviews, 25(5):831-866 (2004).

* cited by examiner

PHARMACEUTICAL USE OF SUBSTITUTED AMIDES

CROSS-REFERENCE TO RELATED APPLICATIONS

This application is the United States national stage application, pursuant to 35 U.S.C. §371, of PCT/US2008/059903, filed Apr. 10, 2008, which claims benefit of U.S. Provisional Patent Application No. 60/926,924, filed Apr. 30, 2007, and European Patent Application No. 07106828.2, filed Apr. 24, 2007.

FIELD OF INVENTION

The present invention relates to use of substituted amides and pharmaceutical compositions comprising the same for treating disorders where it is desirable to modulate the activity of 11β-hydroxysteroid dehydrogenase type 1 (11βHSD1). The present invention also relates to novel substituted amides, to their use in therapy, to pharmaceutical compositions comprising the same, to the use of said compounds in the manufacture of medicaments, and to therapeutic methods comprising the administration of the compounds. The present compounds modulate the activity of 11β-hydroxysteroid dehydrogenase type 1 (11βHSD1) and are accordingly useful in the treatment of diseases in which such a modulation is beneficial, such as the metabolic syndrome.

BACKGROUND OF THE INVENTION

The metabolic syndrome is a major global health problem. In the US, the prevalence in the adult population is currently estimated to be approximately 25%, and it continues to increase both in the US and worldwide. The metabolic syndrome is characterised by a combination of insulin resistance, dyslipidemia, obesity and hypertension leading to increased morbidity and mortality of cardiovascular diseases. People with the metabolic syndrome are at increased risk of developing frank type 2 diabetes, the prevalence of which is equally escalating.

In type 2 diabetes, obesity and dyslipidemia are also highly prevalent and around 70% of people with type 2 diabetes additionally have hypertension once again leading to increased mortality of cardiovascular diseases.

In the clinical setting, it has long been known that glucocorticoids are able to induce all of the cardinal features of the metabolic syndrome and type 2 diabetes.

11β-hydroxysteroid dehydrogenase type 1 (11βHSD1) catalyses the local generation of active glucocorticoid in several tissues and organs including predominantly the liver and adipose tissue, but also e.g., skeletal muscle, bone, pancreas, endothelium, ocular tissue and certain parts of the central nervous system. Thus, 11βHSD1 serves as a local regulator of glucocorticoid actions in the tissues and organs where it is expressed (Tannin et al., J. Biol. Chem., 266, 16653 (1991); Bujalska et al., Endocrinology, 140, 3188 (1999); Whorwood et al., J. Clin Endocrinol Metab., 86, 2296 (2001); Cooper et al., Bone, 27, 375 (2000); Davani et al., J. Biol. Chem., 275, 34841 (2000); Brem et al., Hypertension, 31, 459 (1998); Rauz et al., Invest. Opthalmol. Vis. Sci., 42, 2037 (2001); Moisan et al., Endocrinology, 127, 1450 (1990)).

The role of 11βHSD1 in the metabolic syndrome and type 2 diabetes is supported by several lines of evidence. In humans, treatment with the non-specific 11βHSD1 inhibitor carbenoxolone improves insulin sensitivity in lean healthy volunteers and people with type 2 diabetes. Likewise, 11βHSD1 knock-out mice are resistant to insulin resistance induced by obesity and stress. Additionally, the knock-out mice present with an anti-atherogenic lipid profile of decreased VLDL triglycerides and increased HDL-cholesterol. Conversely, mice that overexpress 11βHSD1 in adipocytes develop insulin resistance, hyperlipidemia and visceral obesity, a phenotype that resembles the human metabolic syndrome (Andrews et al., J. Clin. Endocrinol. Metab., 88, 285 (2003); Walker et al., J. Clin. Endocrinol. Metab., 80, 3155 (1995); Morton et al., J. Biol. Chem., 276, 41293 (2001); Kotelevtsev et al., Proc. Natl. Acad. Sci. USA, 94, 14924 (1997); Masuzaki et al., Science, 294, 2166 (2001)).

The more mechanistic aspects of 11βHSD1 modulation and thereby modulation of intracellular levels of active glucocorticoid have been investigated in several rodent models and different cellular systems. 11βHSD1 promotes the features of the metabolic syndrome by increasing hepatic expression of the rate-limiting enzymes in gluconeogenesis, namely phosphoenolpyuvate carboxykinase and glucose-6-phosphatase, promoting the differentiation of preadipocytes into adipocytes thus facilitating obesity, directly and indirectly stimulating hepatic VLDL secretion, decreasing hepatic LDL uptake and increasing vessel contractility (Kotelevtsev et al., Proc. Natl. Acad. Sci. USA, 94, 14924 (1997); Morton et al., J. Biol. Chem. 276, 41293 (2001); Bujalska et al., Endocrinology, 140, 3188 (1999); Souness et al., Steroids, 67, 195 (2002), Brindley & Salter, Prog. Lipid Res., 30, 349 (1991)).

WO 01/90090, WO 01/90091, WO 01/90092, WO 01/90093, and WO 01/90094 discloses various thiazol-sulfonamides as inhibitors of the human 11β-hydroxysteroid dehydro-genase type 1 enzyme, and further states that said compounds may be useful in treating diabetes, obesity, glaucoma, osteoporosis, cognitive disorders, immune disorders and depression.

We have now found substituted amides that modulate the activity of 11βHSD1 leading to altered intracellular concentrations of active glucocorticoid. More specifically, the present compounds inhibit the activity of 11βHSD1 leading to decreased intracellular concentrations of active glucocorticoid. Thus, the present compounds can be used to treat disorders where a decreased level of active intracellular glucocorticoid is desirable, such as e.g., the metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, and adverse effects of treatment or therapy with glucocorticoid receptor agonists.

One object of the present invention is to provide compounds, pharmaceutical compositions and use of compounds that modulate the activity of 11βHSD1.

Definitions

In the following structural formulas and throughout the present specification, the following terms have the indicated meaning. The examples provided in the definitions present in this application are non-inclusive unless otherwise stated. They include but are not limited to the recited examples.

The term "halogen" "halo" includes fluorine, chlorine, bromine, and iodine.

The term "trihalomethyl" includes trifluoromethyl, trichloromethyl, tribromomethyl, and triiodomethyl.

The term "trihalomethoxy" includes trifluorometoxy, trichlorometoxy, tribromometoxy, and triiodometoxy.

The term "hydroxy" shall mean the radical —OH.

The term "carboxy" shall mean the radical —(C=O)OH.

The term "cyano" shall mean the radical —CN.

The term "$C_1$-$C_6$alkyl" as used herein represents a saturated, branched or straight hydrocarbon group having from 1 to 6 carbon atoms, e.g. $C_1$-$C_2$alkyl, $C_1$-$C_3$alkyl, $C_1$-$C_4$alkyl, $C_1$-$C_6$alkyl, $C_2$-$C_6$alkyl, $C_3$-$C_6$alkyl, and the like. Representative examples are methyl, ethyl, propyl (e.g. prop-1-yl, prop-2-yl (or iso-propyl)), butyl (e.g. 2-methylprop-2-yl (or tent-butyl), but-1-yl, but-2-yl), pentyl (e.g. pent-1-yl, pent-2-yl, pent-3-yl), 2-methylbut-1-yl, 3-methylbut-1-yl, hexyl (e.g. hex-1-yl), and the like. The term "$C_1$-$C_4$alkyl" as used herein represents a saturated, branched or straight hydrocarbon group having from 1 to 4 carbon atoms, e.g. $C_1$-$C_2$alkyl, $C_1$-$C_3$alkyl, $C_1$-$C_4$ alkyl, and the like. Representative examples are methyl, ethyl, propyl (e.g. prop-1-yl, prop-2-yl (or iso-propyl)), butyl (e.g. 2-methylprop-2-yl (or tent-butyl), but-1-yl, but-2-yl), and the like.

The term "bridge" as used herein represents a connection in a saturated or partly saturated ring between two atoms of such ring that are not neighbors through a chain of 1 to 3 atoms selected from carbon, nitrogen, oxygen and sulfur. Representative examples of such connecting chains are —$CH_2$—, —$CH_2CH_2$—, —$CH_2NHCH_2$—, —$CH_2CH_2CH_2$—, —$CH_2OCH_2$—, and the like. In one embodiment according to the invention, the connecting chain is selected from the group consisting of —$CH_2$—, —$CH_2CH_2$—, or —$CH_2OCH_2$—.

The term "spiro atom" as used herein represents a carbon atom in a saturated or partly saturated ring that connects both ends of a chain of 3 to 7 atoms selected from carbon, nitrogen, oxygen and sulfur. Representative examples are —$(CH_2)_5$—, —$(CH_2)_3$—, —$(CH_2)_4$—, —$CH_2NHCH_2CH_2$—, —$CH_2CH_2NHCH_2CH_2$—, —$CH_2NHCH_2CH_2CH_2$—, —$CH_2CH_2OCH_2$—, —$OCH_2$—$CH_2O$—, and the like.

The term "saturated or partially saturated monocyclic, bicyclic, or tricyclic ring system" represents but is not limited to aziridinyl, azepanyl, azocanyl, pyrrolinyl, pyrrolidinyl, 2-imidazolinyl, imidazolidinyl, 2-pyrazolinyl, morpholinyl, piperidinyl, thiomorpholinyl, piperazinyl, phthalimide, 1,2,3,4-tetrahydro-quinolinyl, 1,2,3,4-tetrahydro-isoquinolinyl, 1,2,3,4-tetrahydro-quinoxalinyl, indolinyl, 1,6-aza-bicyclo[3.2.1]octane, 2-aza-bicyclo[4.1.1]octane, 2-aza-bicyclo[3.2.1]octanyl, 7-aza-bicyclo[4.1.1]octanyl, 9-aza-bicyclo[3.3.2]decanyl, 4-aza-tricyclo[4.3.1.1$^{3,8}$]undecanyl, 9-aza-tricyclo[3.3.2.0$^{3,7}$]decanyl.

The term "saturated or partially saturated ring" represents cyclopropyl, cyclobutyl, cyclopentyl, cyclohexyl, cyclobutenyl, cyclopentenyl, cyclohexenyl, cycloheptenyl, cyclooctenyl, cyclononenyl, cyclodecenyl, tetrahydrofuranyl, and tetrahydropyranyl.

The term "saturated or partially saturated aromatic ring" represents cyclopentyl, cyclohexyl, cyclobutenyl, cyclopentenyl, cyclohexenyl, cycloheptenyl, cyclooctenyl, cyclononenyl, cyclodecenyl, tetrahydrofuranyl, tetrahydropyranyl, phenyl, pyridyl, and pyrimidinyl.

The term "$C_3$-$C_{10}$cycloalkyl" as used herein represents a saturated monocyclic carbocyclic ring having from 3 to 10 carbon atoms, e.g. $C_{3-6}$-alkyl, $C_{3-8}$-alkyl, $C_{3-10}$-alkyl, and the like. In one aspect of the invention, $C_3$-$C_{10}$cycloalkyl is $C_3$-$C_6$cycloalkyl. Representative examples of $C_3$-$C_{10}$cycloalkyl are cyclopropyl, cyclobutyl, cyclopentyl, cyclohexyl, cycloheptyl, cyclooctyl, and the like. Representative examples of $C_3$-$C_6$cycloalkyl are cyclopropyl, cyclobutyl, cyclopentyl, and cyclohexyl. $C_3$-$C_{10}$cycloalkyl is also intended to represent a saturated bicyclic carbocyclic ring having from 4 to 10 carbon atoms. Representative examples are decahydronaphthalenyl, bicyclo[3.3.0]octanyl, and the like. $C_3$-$C_{10}$cycloalkyl is also intended to represent a saturated carbocyclic ring having from 3 to 10 carbon atoms and containing one or two carbon bridges. Representative examples are adamantyl, norbornanyl, nortricyclyl, bicyclo[3.2.1]octanyl, bicyclo[2.2.2]octanyl, tricyclo[5.2.1.0/2,6]-decanyl, bicyclo[2.2.1]heptyl, and the like. $C_3$-$C_{10}$cycloalkyl is also intended to represent a saturated carbocyclic ring having from 3 to 10 carbon atoms and containing one or more spiro atoms. Representative examples are spiro[2.5]octanyl, spiro[4.5]decanyl, and the like.

The term "cycloalkylalkyl" represents a cycloalkyl group as defined above attached through an alkyl group having the indicated number of carbon atoms or substituted alkyl group as defined above (e.g., cyclopropylmethyl, cyclobutylethyl, and adamantylmethyl).

The term "cycloalkenyl" represents a partially saturated, mono-, bi-, tri- or spiro-carbocyclic group having the specified number of carbon atoms (e.g., cyclobutenyl, cyclopentenyl, cyclohexenyl, cycloheptenyl, cyclooctenyl, cyclononenyl, and cyclodecenyl).

The term "cycloalkylcarbonyl" represents a cycloalkyl group as defined above having the indicated number of carbon atoms attached through a carbonyl group (e.g., cyclopropylcarbonyl and cyclohexylcarbonyl).

The term "cycloalkylalkylcarbonyl" represents a cycloalkyl group as defined above attached through an alkyl group having the indicated number of carbon atoms or substituted alkyl group as defined above (e.g., cyclohexylmethylcarbonyl and cycloheptylethylcarbonyl).

The term "hetcycloalkyl" represents a saturated mono-, bi-, tri-, or spiro-carbocyclic group having the specified number of atoms with 1-4 of the specificied number being heteroatoms or groups selected from nitrogen, oxygen, sulphur, and $S(O)_m$ (m=0-2) (e.g., tetrahydrofuranyl, tetrahydropyranyl, tertahydrothiopyranyl, piperidine, and pyridzine).

The term "hetcycloalkylalkyl" represents a hetcycloalkyl group as defined above attached through an alkyl group having the indicated number of carbon atoms (e.g., tetrahydrofuranylmethyl, tetrahydropyranylethyl, and tertahydrothiopyranylmethyl).

The term "hetcycloalkylcarbonyl" represents a hetcycloalkyl group as defined above having the indicated number of carbon atoms attached through a carbonyl group (e.g., 1-piperidin-4-yl-carbonyl and 1-(1,2,3,4-tetrahydro-isoquinolin-6-yl)carbonyl).

The term "alkyloxy" represents an alkyl group having the indicated number of carbon atoms attached through an oxygen bridge (e.g., methoxy, ethoxy, propyloxy, allyloxy, and cyclohexyloxy).

The term "alkyloxyalkyl" represents an alkyloxy group as defined above attached through an alkyl group having the indicated number of carbon atoms (e.g., methyloxymethyl).

The term "aryl" represent monocyclic, bicyclic or polycyclic carbocyclic aromatic rings. Representative examples are phenyl, naphthyl (e.g. naphth-1-yl, naphth-2-yl), anthryl (e.g. anthr-1-yl, anthr-9-yl), phenanthryl (e.g. phenanthr-1-yl, phenanthr-9-yl), and the like. Aryl is also intended to include monocyclic, bicyclic or polycyclic carbocyclic aromatic rings substituted with carbocyclic aromatic rings. Representative examples are biphenyl (e.g. biphenyl-2-yl, biphenyl-3-yl, biphenyl-4-yl), phenylnaphthyl (e.g. 1-phenylnaphth-2-yl, 2-phenylnaphth-1-yl), and the like. Aryl is also intended to include partially saturated bicyclic or polycyclic carbocyclic rings with at least one unsaturated moiety (e.g. a benzo moiety). Representative examples are, indanyl (e.g. indan-1-yl, indan-5-yl), indenyl (e.g. inden-1-yl, inden-5-yl), 1,2,3,4- tetrahydronaphthyl (e.g. 1,2,3,4-tetrahydronaphth-1-yl, 1,2,3,4-tetra-hydronaphth-2-yl, 1,2,3,4-tetrahydronaphth-6-yl), 1,2-dihydronaphthyl (e.g. 1,2-dihydronaphth-1-yl, 1,2-dihydronaphth-4-yl, 1,2-dihydronaphth-6-yl), fluorenyl (e.g. fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (e.g. benzonorborn-3-yl, benzonorborn-6-yl), 1,4-ethano-1,2,3,4-tetrahydronapthyl (e.g. 1,4-ethano-1,2,3,4-tetrahydronapth-2-yl, 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro-[piperidine-4,2'-indane]-1-yl, spiro[piperidine-4,1'-indane]-3'-yl, spiro[pyrrolidine-3,2'-indane]-1-yl, spiro[pyrrolidine-3,1'-(3',4'-dihydronaphthalene)]-1-yl, spiro[piperidine-3,1'-(3',4'-dihydronaphthalene)]-1-yl, spiro[piperidine-4,1'-(3',4'-dihydronaphthalene)]-1-yl, spiro[imidazolidine-4,2'-indane]-1-yl, spiro[piperidine-4,1'-indene]-1-yl, and the like.

The term "heteroaryl" or "hetaryl" includes as used herein is intended to include monocyclic heterocyclic aromatic rings containing one or more heteroatoms selected from nitrogen, oxygen, sulfur, SO and $S(=O)_2$. Representative examples are pyrrolyl (e.g. pyrrol-1-yl, pyrrol-2-yl, pyrrol-3-yl), furanyl (e.g. furan-2-yl, furan-3-yl), thienyl (e.g. thien-2-yl, thien-3-yl), oxazolyl (e.g. oxazol-2-yl, oxazol-4-yl, oxazol-5-yl), thiazolyl (e.g. thiazol-2-yl, thiazol-4-yl, thiazol-5-yl), imidazolyl (e.g. imidazol-2-yl, imidazol-4-yl, imidazol-5-yl), pyrazolyl (e.g. pyrazol-1-yl, pyrazol-3-yl, pyrazol-5-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), 1,2,3-triazolyl (e.g. 1,2,3-triazol-1-yl, 1,2,3-triazol-4-yl, 1,2,3-triazol-5-yl), 1,2,4-triazolyl (e.g. 1,2,4-triazol-1-yl, 1,2,4-triazol-3-yl, 1,2,4-triazol-5-yl), 1,2,3-oxadiazolyl (e.g. 1,2,3-oxadiazol-4-yl, 1,2,3-oxadiazol-5-yl), 1,2,4-oxadiazolyl (e.g. 1,2,4-oxadiazol-3-yl, 1,2,4-oxadiazol-5-yl), 1,2,5-oxadiazolyl (e.g. 1,2,5-oxadiazol-3-yl, 1,2,5-oxadiazol-4-yl), 1,3,4-oxadiazolyl (e.g. 1,3,4-oxadiazol-2-yl, 1,3,4-oxadiazol-5-yl), 1,2,3-thiadiazolyl (e.g. 1,2,3-thiadiazol-4-yl, 1,2,3-thiadiazol-5-yl), 1,2,4-thiadiazolyl (e.g. 1,2,4-thiadiazol-3-yl, 1,2,4-thiadiazol-5-yl), 1,2,5-thiadiazolyl (e.g. 1,2,5-thiadiazol-3-yl, 1,2,5-thiadiazol-4-yl), 1,3,4-thiadiazolyl (e.g. 1,3,4-thiadiazol-2-yl, 1,3,4-thiadiazol-5-yl), tetrazolyl (e.g. tetrazol-1-yl, tetrazol-5-yl), pyranyl (e.g. pyran-2-yl), pyridinyl (e.g. pyridine-2-yl, pyridine-3-yl, pyridine-4-yl), pyridazinyl (e.g. pyridazin-2-yl, pyridazin-3-yl), pyrimidinyl (e.g. pyrimidin-2-yl, pyrimidin-4-yl, pyrimidin-5-yl), pyrazinyl, 1,2,3-triazinyl, 1,2,4-triazinyl, 1,3,5-triazinyl, thiadiazinyl, azepinyl, azecinyl, and the like. Heteroaryl is also intended to include bicyclic heterocyclic aromatic rings containing one or more heteroatoms selected from nitrogen, oxygen, sulfur, $S(=O)$ and $S(=O)_2$. Representative examples are indolyl (e.g. indol-1-yl, indol-2-yl, indol-3-yl, indol-5-yl), isoindolyl, benzofuranyl (e.g. benzo[b]furan-2-yl, benzo[b]furan-3-yl, benzo[b]furan-5-yl, benzo[c]furan-2-yl, benzo[c]furan-3-yl, benzo[c]furan-5-yl), benzothienyl (e.g. benzo-[b]thien-2-yl, benzo[b]thien-3-yl, benzo[b]thien-5-yl, benzo[c]thien-2-yl, benzo[c]thien-3-yl, benzo[c]thien-5-yl), indazolyl (e.g. indazol-1-yl, indazol-3-yl, indazol-5-yl), indolizinyl (e.g. indolizin-1-yl, indolizin-3-yl), benzopyranyl (e.g. benzo[b]pyran-3-yl, benzo[b]pyran-6-yl, benzo[c]pyran-1-yl, benzo[c]pyran-7-yl), benzimidazolyl (e.g. benzimidazol-1-yl, benzimidazol-2-yl, benzimidazol-5-yl), benzothiazolyl (e.g. benzothiazol-2-yl, benzothiazol-5-yl), benzisothiazolyl, benzoxazolyl, benzisoxazolyl, benzoxazinyl, benzotriazolyl, naphthyridinyl (e.g. 1,8-naphthyridin-2-yl, 1,7-naphthyridin-2-yl, 1,6-naphthyridin-2-yl), phthalazinyl (e.g. phthalazin-1-yl, phthalazin-5-yl), pteridinyl, purinyl (e.g. purin-2-yl, purin-6-yl, purin-7-yl, purin-8-yl, purin-9-yl), quinazolinyl (e.g. quinazolin-2-yl, quinazolin-4-yl, quinazolin-6-yl), cinnolinyl, quinoliny (e.g. quinolin-2-yl, quinolin-3-yl, quinolin-4-yl, quinolin-6-yl), isoquinolinyl (e.g. isoquinolin-1-yl, isoquinolin-3-yl, isoquinolin-4-yl), quinoxalinyl (e.g. quinoxalin-2-yl, quinoxalin-5-yl), pyrrolopyridinyl (e.g. pyrrolo[2,3-b]pyridinyl, pyrrolo[2,3-c]pyridinyl, pyrrolo[3,2-c]pyridinyl), furopyridinyl (e.g. furo[2,3-b]pyridinyl, furo[2,3-c]pyridinyl, furo[3,2-c]pyridinyl), thienopyridinyl (e.g. thieno[2,3-b]pyridinyl, thieno[2,3-c]pyridinyl, thieno[3,2-c]pyridinyl), imidazopyridinyl (e.g. imidazo[4,5-b]pyridinyl, imidazo[4,5-c]pyridinyl, imidazo[1,5-a]pyridinyl, imidazo[1,2-a]pyridinyl), imidazopyrimidinyl (e.g. imidazo[1,2-a]pyrimidinyl, imidazo[3,4-a]pyrimidinyl), pyrazolopyridinyl (e.g. pyrazolo[3,4-b]pyridinyl, pyrazolo[3,4-c]pyridinyl, pyrazolo[1,5-a]pyridinyl), pyrazolopyrimidinyl (e.g. pyrazolo[1,5-a]pyrimidinyl, pyrazolo[3,4-d]pyrimidinyl), thiazolopyridinyl (e.g. thiazolo[3,2-d]pyridinyl), thiazolopyrimidinyl (e.g. thiazolo[5,4-d]pyrimidinyl), imidazothiazolyl (e.g. imidazo[2,1-b]thiazolyl), triazolopyridinyl (e.g. triazolo[4,5-b]pyridinyl), triazolopyrimidinyl (e.g. 8-azapurinyl), and the like. Heteroaryl is also intended to include polycyclic heterocyclic aromatic rings containing one or more heteroatoms selected from nitrogen, oxygen, sulfur, $S(=O)$ and $S(=O)_2$. Representative examples are carbazolyl (e.g. carbazol-2-yl, carbazol-3-yl, carbazol-9-yl), phenoxazinyl (e.g. phenoxazin-10-yl), phenazinyl (e.g. phenazin-5-yl), acridinyl (e.g. acridin-9-yl, acridin-10-yl), phenothiazinyl (e.g. phenothiazin-10-yl), carbolinyl (e.g. pyrido[3,4-b]indol-1-yl, pyrido[3,4-b]indol-3-yl), phenanthrolinyl (e.g. phenanthrolin-5-yl), and the like. Heteroaryl is also intended to include partially saturated monocyclic, bicyclic or polycyclic heterocyclic rings containing one or more heteroatoms selected from nitrogen, oxygen, sulfur, $S(=O)$ and $S(=O)_2$. Representative examples are pyrrolinyl, pyrazolinyl, imidazolinyl (e.g. 4,5-dihydroimidazol-2-yl, 4,5-dihydroimidazol-1-yl), indolinyl (e.g. 2,3-dihydroindol-1-yl, 2,3-dihydroindol-5-yl), dihydrobenzofuranyl (e.g. 2,3-dihydrobenzo[b]furan-2-yl, 2,3-dihydrobenzo[b]furan-4-yl), dihydrobenzothienyl (e.g. 2,3-dihydrobenzo[b]thien-2-yl, 2,3-dihydrobenzo[b]thien-5-yl), 4,5,6,7-tetrahydrobenzo[b]furan-5-yl), dihydrobenzopyranyl (e.g. 3,4-dihydrobenzo-[b]pyran-3-yl, 3,4-dihydrobenzo[b]pyran-6-yl, 3,4-dihydrobenzo[c]pyran-1-yl, dihydrobenzo[c]pyran-7-yl), oxazolinyl (e.g. 4,5-dihydrooxazol-2-yl, 4,5-dihydrooxazol-4-yl, 4,5-dihydrooxazol-5-yl), isoxazolinyl, oxazepinyl, tetrahydroindazolyl (e.g. 4,5,6,7-tetrahydroindazol-1-yl, 4,5,6,7-tetrahydroindazol-3-yl, 4,5,6,7-tetrahydroindazol-4-yl, 4,5,6,7-tetrahydroindazol-6-yl), tetrahydrobenzimidazolyl (e.g. 4,5,6,7-tetrahydrobenzimidazol-1-yl, 4,5,6,7-tetrahydrobenzimidazol-5-yl), tetrahydroimidazo[4,5-c]pyridyl (e.g. 4,5,6,7-tetrahydroimidazo[4,5-c]pyrid-1-yl, 4,5,6,7-tetrahydroimidazo[4,5-c]pyrid-5-yl, 4,5,6,7-tetrahydroimidazo[4,5-c]pyrid-6-yl), tetrahydroquinolinyl (e.g. 1,2,3,4-tetrahydro-quinolinyl, 5,6,7,8-tetrahydroquinolinyl), tetrahydroisoquinolinyl (e.g. 1,2,3,4-tetrahydro-isoquinolinyl, 5,6,7,8-tetrahydroisoquinolinyl), tetrahydroquinoxalinyl (e.g. 1,2,3,4-tetrahydro-quinoxalinyl, 5,6,7,8-tetrahydroquinoxalinyl), and the like. Heteroaryl is also intended to include partially saturated bicyclic or polycyclic heterocyclic rings containing one or more spiro atoms. Representative examples are spiro[isoquinoline-3,1'-cyclohexan]-1-yl, spiro[piperidine-4,1'-benzo[c]thiophen]-1-yl, spiro[piperidine-4,1'-benzo[c]furan]-1-yl, spiro[piperidine-4,3'-benzo-[b]furan]-1-yl, spiro[piperidine-4,3'-coumarin]-1-yl, and the like.

The term "arylalkyl" represents an aryl group as defined above attached through an alkyl group having the indicated number of carbon atoms (e.g., benzyl, phenylethyl, 3-phenylpropyl, 1-naphtylmethyl, and 2-(1-naphtyl)ethyl).

The term "hetarylalkyl" or "hetaralkyl" represents a hetaryl group as defined above attached through an alkyl group having the indicated number of carbon atoms (e.g., (2-furyl)methyl, (3-furyl)methyl, (2-thienyl)methyl, (3-thienyl)methyl, (2-pyridyl)methyl, and 1-methyl-1-(2-pyrimidyl)ethyl).

The term "aryloxyhetaryl" represents an aryloxy group as defined above attached through a hetaryl group (e.g., 2-phenoxy-pyridyl).

The term "aryloxy" represents an aryl group as defined above attached through an oxygen bridge (e.g., phenoxy and naphthyloxy).

The term "hetaryloxy" represents a hetaryl group as defined above attached through an oxygen bridge (e.g., 2-pyridyloxy).

The term "arylalkyloxy" represents an arylalkyl group as defined above attached through an oxygen bridge (e.g., phenethyloxy and naphthylmethyloxy).

The term "hetarylalkyloxy" represents a hetarylalkyl group as defined above attached through an oxygen bridge (e.g., 2-pyridylmethyloxy).

The term "alkyloxycarbonyl" represents an alkyloxy group as defined above attached through a carbonyl group (e.g., methylformiat and ethylformiat).

The term "aryloxycarbonyl" represents an aryloxy group as defined above attached through a carbonyl group (e.g., phenylformiat and 2-thiazolylformiat).

The term "arylalkyloxycarbonyl" represents an "arylalkyloxy" group as defined above attached through a carbonyl group (e.g., benzylformiat and phenyletylformiat).

The term "hetaryloxyaryl" represents a hetaryloxy group as defined above attached through an aryl group as defined above (e.g. 1-phenoxy-isoquinolyl and 2-phenoxy-pyridyl).

The term "hetaryloxyhetaryl" represents a hetaryloxy group as defined above attached through a hetaryl group as defined above (e.g. 1-(2-pyridyloxy-isoquinoline) and 2-(imidazol-2-yloxy-pyridine)).

The term "aryloxyalkyl" represents an aryloxy group as defined above attached through an alkyl group having the indicated number of carbon atoms (e.g., phenoxymethyl and naphthyloxyethyl).

The term "aryloxyaryl" represents an aryloxy group as defined above attached through an aryl group as defined above (e.g., 1-phenoxy-naphthalene and phenyloxyphenyl).

The term "arylalkyloxyalkyl" represents an arylalkyloxy group as defined above attached through an alkyl group having the indicated number of carbon atoms (e.g. ethoxymethylbenzene and 2-methoxymethyl-naphthalene).

The term "hetaryloxyalkyl" represents a hetaryloxy group as defined above attached through an alkyl group having the indicated number of carbon atoms (e.g., 2-pyridyloxymethyl and 2-quinolyloxyethyl).

The term "hetarylalkyloxyalkyl" represents a hetarylalkyloxy group as defined above attached through an alkyl group having the indicated number of carbon atoms (e.g., 4-methoxymethyl-pyrimidine and 2-methoxymethyl-quinoline).

The term "alkylcarbonyl" represents an alkyl group as defined above having the indicated number of carbon atoms attached through a carbonyl group (e.g., octylcarbonyl, pentylcarbonyl, and 3-hexenylcarbonyl).

The term "arylcarbonyl" represents an aryl group as defined above attached through a carbonyl group (e.g., benzoyl).

The term "hetarylcarbonyl" represents a hetaryl group as defined above attached through a carbonyl group (e.g., 2-thiophenylcarbonyl, 3-methoxy-anthrylcarbonyl, and oxazolylcarbonyl).

The term "carbonylalkyl" represents a carbonyl group attached through an alkyl group having the indicated number of carbon atoms (e.g., acetyl).

The term "alkylcarbonylalkyl" represents an alkylcarbonyl group as defined above attached through an alkyl group having the indicated number of carbon atoms (e.g., propan-2-one and 4,4-dimethyl-pentan-2-one).

The term "arylcarbonylalkyl" represents a arylcarbonyl group as defined above attached through an alkyl group having the indicated number of carbon atoms (e.g., 1-phenylpropan-1-one and 1-(3-chloro-phenyl)-2-methyl-butan-1-one).

The term "hetarylcarbonylalkyl" represents a hetarylcarbonyl group as defined above attached through an alkyl group having the indicated number of carbon atoms (e.g., 1-pyridin-2-yl-propan-1-one and 1-(1-H-imidazol-2-yl)-propan-1-one).

The term "arylalkylcarbonyl" represents an arylalkyl group as defined above having the indicated number of carbon atoms attached through a carbonyl group (e.g., phenylpropylcarbonyl and phenylethylcarbonyl).

The term "hetarylalkylcarbonyl" represents a hetarylalkyl group as defined above wherein the alkyl group is in turn attached through a carbonyl (e.g., imidazolylpentylcarbonyl).

The term "alkylcarboxy" represents an alkylcarbonyl group as defined above wherein the carbonyl is in turn attached through an oxygen bridge (e.g., heptylcarboxy, cyclopropylcarboxy, and 3-pentenylcarboxy).

The term "arylcarboxy" represents an arylcarbonyl group as defined above wherein the carbonyl is in turn attached through an oxygen bridge (e.g., benzoic acid).

The term "alkylcarboxyalkyl" represents an alkylcarboxy group as defined above wherein the oxygen is attached via an alkyl bridge (e.g., heptylcarboxymethyl, propylcarboxy tert-butyl, and 3-pentylcarboxyethyl).

The term "arylalkylcarboxy" represents an arylalkylcarbonyl group as defined above wherein the carbonyl is in turn attached through an oxygen bridge (e.g., benzylcarboxy and phenylpropylcarboxy).

The term "arylalkylcarboxyalkyl" represents an arylalkylcarboxy group as defined above wherein the carboxy group is in turn attached through an alkyl group having the indicated number of carbon atoms (e.g., benzylcarboxymethyl and phenylpropylcarboxypropyl).

The term "hetarylcarboxy" represents a hetarylcarbonyl group as defined above wherein the carbonyl is in turn attached through an oxygen bridge (e.g., pyridine-2-carboxylic acid).

The term "hetarylalkylcarboxy" represents a hetarylalkylcarbonyl group as defined above wherein the carbonyl is in turn attached through an oxygen bridge (e.g. (1-H-imidazol-2-yl)-acetic acid and 3-pyrimidin-2-yl-propionic acid).

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent, the substituents may be the same or different.

The term "treatment" or "treating" is defined as the management and care of a patient for the purpose of combating or alleviating the disease, condition, or disorder, and the term includes the administration of the active compound to prevent or delay the onset of the symptoms or complications; alleviating (both temporary and permanent) the symptoms or complications; and/or eliminating the disease, condition, or disorder. Thus, "treatment" or "treating" includes prevention and/or prophylaxis of the disease, condition, or disorder.

The term "pharmaceutically acceptable" is defined as being suitable for administration to humans without adverse events.

The term "prodrug" is defined as a chemically modified form of the active drug, said prodrug being administered to the patient and subsequently being converted to the active drug. Techniques for development of prodrugs are well known in the art.

SUMMARY OF THE INVENTION

In one aspect of the invention substituted benzamide based inhibitors that modulate the activity of 11βHSD1 leading to altered intracellular concentrations of active gluco-corticoid, are provided. More specifically, the present compounds inhibit the activity of 11βHSD1 leading to decreased intracellular concentrations of active glucocorticoid. Thus, the present compounds can be used to treat disorders where a decreased level of active intracellular glucocorticoid is desirable, such as e.g. the metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, and adverse effects of treatment or therapy with glucocorticoid receptor agonists.

One object of the present invention is to provide compounds, pharmaceutical compositions and use of compounds that modulate the activity of 11βHSD1.

The present invention furthermore relates to the use in therapy of the compounds according to the invention, to pharmaceutical compositions comprising the compounds, to the use of said compounds in the manufacture of medicaments, and to therapeutic methods comprising the administration of said compounds.

DETAILED DESCRIPTION OF THE INVENTION

The invention provides for a compound of the general formula (I):

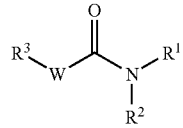

(I)

wherein $R^1$ is hydrogen, methyl, ethyl, isopropyl and cyclopropyl;

$R^2$ is selected from one of the following structural elements:

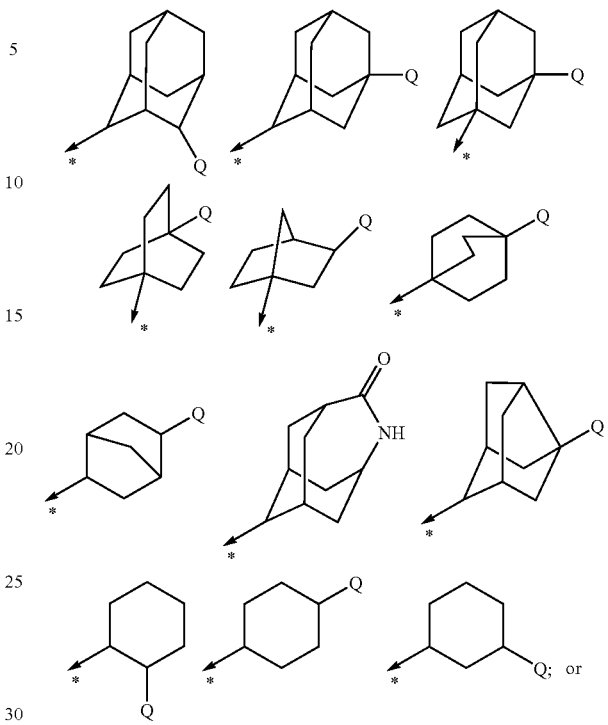

$R^2$ is selected from $C_1$-$C_6$alkyl, $C_3$-$C_{10}$cycloalkyl, aryl, hetaryl, aryl$C_1$-$C_6$alkyl, and hetaryl$C_1$-$C_6$alkyl, wherein each of the alkyl, cycloalkyl, aryl, and hetaryl groups are independently substituted with 0-3 $R^{11}$;

alternatively, $R^1$ and $R^2$ together with the nitrogen to which they are attached, is selected from the following structural elements:

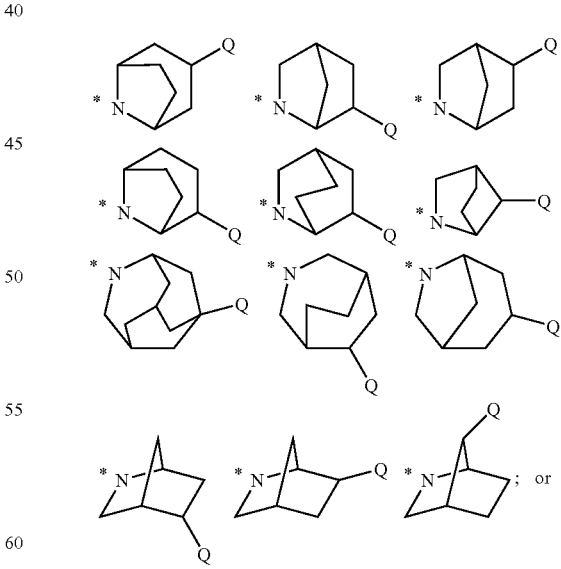

$R^1$ and $R^2$ together with the nitrogen to which they are attaced, form a 5-12 membered saturated or partially saturated monocyclic, bicyclic, or tricyclic ring consisting of the shown nitrogen, 4-10 carbon atoms, and 0-2 additional heteroatoms selected from nitrogen, oxygen, and $S(O)_m$, wherein this ring is substituted with 0-3 groups selected from $C_1$-$C_6$alkyl, $C_3$-$C_{10}$cycloalkyl, $C_3$-$C_{10}$hetcycloalkyl, $C_3$-$C_6$-spirocycloalkyl, 3-6 membered spirohetcycloalkyl, aryl, hetaryl, aryl$C_1$-$C_6$alkyl, hetaryl$C_1$-$C_6$alkyl, —C(=O)$R^{12}$, —S(O)$_n$ $R^{12}$—OH, oxo, $C_1$-$C_6$alkyloxy, aryl$C_1$-$C_6$alkyl-oxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl and aryl/hetaryl group is substituted with 0-3 $R^{11}$;

Q is selected from hydroxy, carboxy, hydroxymethylene, —SO$_2$N$R^4R^5$, —SO$_2R^6$, $C_1$-$C_6$alkyl, $C_3$-$C_6$cycloalkyl or —C(O)$R^6$; wherein the alkyl and cycloalkyl groups are optionally substituted with hydroxy, —OC(=O)CH$_3$ or —C(=O)OCH$_3$;

W is —Y—(C$R^7R^8$)$_n$—X—(C$R^9R^{10}$)$_m$—;

X is a chemical bond or S(O)$_n$;

Y is O or S;

m is 0, 1 or 2;

n is 1 or 2;

$R^3$ is selected from $C_3$-$C_{10}$cycloalkyl, 3-10 membered heterocycloalkyl, aryl or hetaryl, wherein the alkyl, cycloalkyl, aryl and hetaryl groups are independently substituted with 0-3 $R^{11}$;

$R^4$ and $R^5$ are independently selected from hydrogen, $C_1$-$C_6$alkyl, $C_3$-$C_{10}$cycloalkyl, aryl, hetaryl, aryl$C_1$-$C_6$alkyl, and hetaryl$C_1$-$C_6$alkyl, wherein each of the alkyl, cycloalkyl, aryl, and hetaryl groups are independently substituted with 0-3 $R^{11}$;

alternatively, $R^4$ and $R^5$ together with the nitrogen to which they are attaced, form a 5-12 membered saturated or partially saturated monocyclic, bicyclic, or tricyclic ring consisting of the shown nitrogen, 4-10 carbon atoms, and 0-2 additional heteroatoms selected from nitrogen, oxygen, and S(O)$_m$, wherein this ring is substituted with 0-3 groups selected from $C_1$-$C_6$alkyl, aryl, hetaryl, aryl$C_1$-$C_6$alkyl, hetaryl$C_1$-$C_6$alkyl, OH, oxo, $C_1$-$C_6$alkyloxy, aryl$C_1$-$C_6$alkyloxy, hetaryl$C_1$-$C_6$alkyloxy, $C_1$-$C_6$alkyloxo$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkylcarboxy, and hetaryl$C_1$-$C_6$alkylcarboxy;

$R^6$ is selected from OH, $C_1$-$C_6$alkyl, $C_3$-$C_{10}$cycloalkyl, 3-10 membered heterocycloalkyl, trihalomethyl, trihalomethyloxy, $C_1$-$C_6$alkyloxy, aryl, aryloxy, aryl$C_1$-$C_6$alkyl, aryl$C_1$-$C_6$alkyloxy, hetaryl, hetaryloxy, hetaryl$C_1$-$C_6$alkyl, hetaryl$C_1$-$C_6$alkyloxy, and N$R^4R^5$;

$R^7$ and $R^8$ are independently selected from hydrogen, halo, cyano, trihalomethyl, trihalomethyloxy, $C_1$-$C_6$alkyl, $C_3$-$C_6$cycloalkyl, 3-10 membered hetcycloalkyl, aryl, hetaryl, aryl$C_1$-$C_6$alkyl, hetaryl$C_1$-$C_6$alkyl, —C(O)$R^6$, —S(O)$_n R^6$, —S(O)$_n$N$R^4R^5$, —N($R^4$)S(O)$_nR^6$, —N($R^4$)C(O)N$R^4R^5$, OH, oxo, $C_1$-$C_6$alkyloxy, aryl$C_1$-$C_6$alkyloxy, hetaryl$C_1$-$C_6$alkyloxy, $C_1$-$C_6$alkyloxo$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, cycloalkyl and aryl/hetaryl group is optionally substituted with 0-3 $R^{12}$;

alternatively, $R^7$ and $R^8$ together with the carbon atom to which they are attached forms a $C_3$-$C_6$cycloalkyl or a 3-10 membered hetcycloalkyl ring optionally substituted with 0-3 $R^{12}$;

$R^9$ and $R^{10}$ are selected from hydrogen, halo, cyano, trihalomethyl, trihalomethyloxy, $C_1$-$C_6$alkyl, $C_3$-$C_6$cycloalkyl, 3-10 membered hetcycloalkyl, aryl, hetaryl, aryl$C_1$-$C_6$alkyl, hetaryl$C_1$-$C_6$alkyl, —C(O)$R^6$, —S(O)$_nR^6$, —S(O)$_n$N$R^4R^5$, —N($R^4$)S(O)$_nR^6$, —N($R^4$)C(O)N$R^4R^5$, OH, oxo, $C_1$-$C_6$alkyloxy, aryl$C_1$-$C_6$alkyloxy, hetaryl$C_1$-

$C_6$alkyloxy, $C_1$-$C_6$alkyloxo$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, cycloalkyl and aryl/hetaryl group is optionally substituted with 0-3 $R^{12}$;

alternatively, $R^9$ and $R^{10}$ together with the carbon atom to which they are attached forms a $C_3$-$C_6$cycloalkyl or a 3-10 membered hetcycloalkyl ring optionally substituted with 0-3 $R^{12}$;

$R^{11}$ is selected from halo, cyano, trihalomethyl, trihalomethyloxy, $C_1$-$C_6$alkyl, $C_3$-$C_6$cycloalkyl, 3-10 membered hetcycloalkyl, $C_3$-$C_6$-spirocycloalkyl, 3-6 membered spirohetcycloalkyl, aryl, hetaryl, aryl$C_1$-$C_6$alkyl, hetaryl$C_1$-$C_6$alkyl, —C(O)$R^6$, —S(O)$_nR^6$, —S(O)$_n$N$R^4R^5$, N($R^4$)S(O)$_nR^6$, —N($R^4$)C(O)N$R^4R^5$, OH, oxo, $C_1$-$C_6$alkyloxy, aryl$C_1$-$C_6$alkyloxy, hetaryl$C_1$-$C_6$alkyloxy, $C_1$-$C_6$alkyloxo$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, cycloalkyl and aryl/hetaryl group is optionally substituted with 0-3 $R^{12}$;

$R^{12}$ is selected from halo, OH, oxo, COOH, cyano, $C_1$-$C_6$alkyloxy, trihalomethyl, $C_3$-$C_{10}$-cycloalkyloxy, aryloxy, hetaryloxy, hetarylthio and aryl$C_1$-$C_6$alkyloxy;

or a salt thereof with a pharmaceutically acceptable acid or base, or any optical isomer or mixture of optical isomers, including a racemic mixture, or any tautomeric forms.

In one aspect, the invention provides for a compound of the general formula (I) wherein:

$R^1$ is hydrogen, methyl, ethyl, isopropyl and cyclopropyl;

$R^2$ is selected from one of the following structural elements:

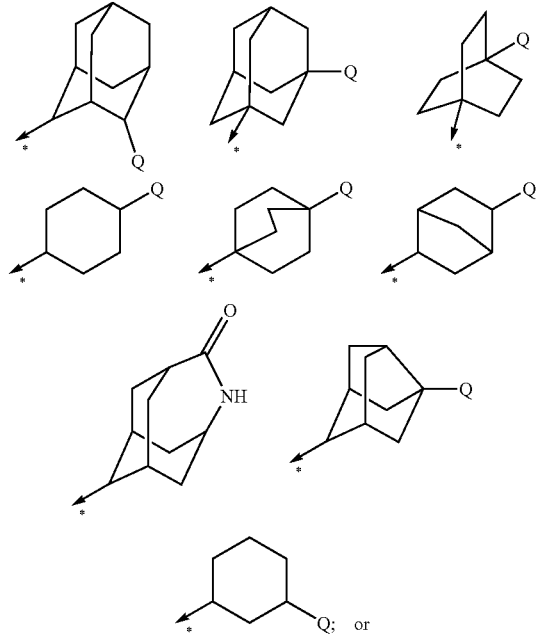

$R^2$ is selected from $C_1$-$C_6$alkyl, $C_3$-$C_{10}$cycloalkyl, aryl, hetaryl, aryl$C_1$-$C_6$alkyl, and hetaryl$C_1$-$C_6$alkyl, wherein each of the alkyl, cycloalkyl, aryl, and hetaryl groups are independently substituted with 0-3 $R^{11}$;

alternatively, $R^1$ and $R^2$ together with the nitrogen to which they are attached, is selected from the following structural elements:

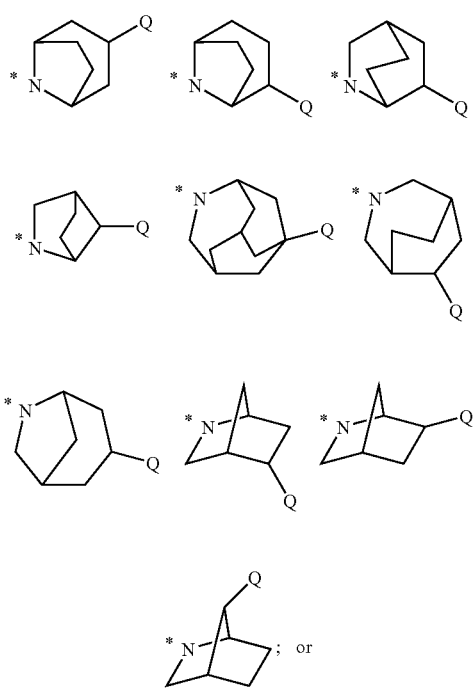

R[1] and R[2] together with the nitrogen to which they are attaced, form a 5-12 membered saturated or partially saturated monocyclic, bicyclic, or tricyclic ring consisting of the shown nitrogen, 4-10 carbon atoms, and 0-2 additional heteroatoms selected from nitrogen, oxygen, and $S(O)_m$, wherein this ring is substituted with 0-3 groups selected from $C_1$-$C_6$alkyl, $C_3$-$C_{10}$cycloalkyl, $C_3$-$C_{10}$hetcycloalkyl, $C_3$-$C_6$-spirocycloalkyl, 3-6 membered spirohetcycloalkyl, aryl, hetaryl, aryl$C_1$-$C_6$alkyl, hetaryl$C_1$-$C_6$alkyl, —C(=O)$R^{12}$, —S(O)$_n$ $R^{12}$—OH, oxo, $C_1$-$C_6$alkyloxy, aryl$C_1$-$C_6$alkyl-oxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl and aryl/hetaryl group is substituted with 0-3 $R^{11}$;

Q is selected from hydroxy, carboxy, hydroxymethylene, —$SO_2NR^4R^5$, $C_1$-$C_6$alkyl, $C_3$-$C_6$-cycloalkyl or —C(O) $R^6$; wherein the alkyl, and cycloalkyl groups are optionally substituted with hydroxy;

W is —Y—(CR[7]R[8])$_n$—X—(CR[9]R[10])$_m$—;
X is a chemical bond or $S(O)_n$;
Y is O or S;
m is 0, 1 or 2;
n is 1 or 2;

R[3] is selected from $C_3$-$C_{10}$cycloalkyl, 3-10 membered heterocycloalkyl, aryl or hetaryl, wherein the alkyl, cycloalkyl, aryl and hetaryl groups are independently substituted with 0-3 $R^{11}$;

R[4] and R[5] are independently selected from hydrogen, $C_1$-$C_6$alkyl, $C_3$-$C_{10}$cycloalkyl, aryl, hetaryl, aryl$C_1$-$C_6$alkyl, and hetaryl$C_1$-$C_6$alkyl, wherein each of the alkyl, cycloalkyl, aryl, and hetaryl groups are independently substituted with 0-3 $R^{11}$;

alternatively, R[4] and R[5] together with the nitrogen to which they are attaced, form a 5-12 membered saturated or partially saturated monocyclic, bicyclic, or tricyclic ring consisting of the shown nitrogen, 4-10 carbon atoms, and 0-2 additional heteroatoms selected from nitrogen, oxygen, and $S(O)_m$, wherein this ring is substituted with 0-3 groups selected from $C_1$-$C_6$alkyl, aryl, hetaryl, aryl$C_1$-$C_6$alkyl, hetaryl$C_1$-$C_6$alkyl, OH, oxo, $C_1$-$C_6$alkyloxy, aryl$C_1$-$C_6$alkyloxy, hetaryl$C_1$-$C_6$alkyloxy, $C_1$-$C_6$alkyloxo$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkylcarboxy, and hetaryl$C_1$-$C_6$alkylcarboxy;

R[6] is selected from OH, $C_1$-$C_6$alkyl, $C_3$-$C_{10}$cycloalkyl, 3-10 membered heterocycloalkyl, trihalomethyl, trihalomethyloxy, $C_1$-$C_6$alkyloxy, aryl, aryloxy, aryl$C_1$-$C_6$alkyl, aryl$C_1$-$C_6$alkyloxy, hetaryl, hetaryloxy, hetaryl$C_1$-$C_6$alkyl, hetaryl$C_1$-$C_6$alkyloxy, and $NR^4R^5$;

R[7] and R[8] are independently selected from hydrogen, halo, cyano, trihalomethyl, trihalomethyloxy, $C_1$-$C_6$alkyl, $C_3$-$C_6$cycloalkyl, 3-10 membered hetcycloalkyl, aryl, hetaryl, aryl$C_1$-$C_6$alkyl, hetaryl$C_1$-$C_6$alkyl, —C(O)$R^6$, —S(O)$_n$$R^6$, —S(O)$_n$$NR^4R^5$, —N($R^4$)S(O)$_n$$R^6$, —N($R^4$)C(O)$NR^4R^5$, OH, oxo, $C_1$-$C_6$alkyloxy, aryl$C_1$-$C_6$alkyloxy, hetaryl$C_1$-$C_6$alkyloxy, $C_1$-Colkyloxo$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, cycloalkyl and aryl/hetaryl group is optionally substituted with 0-3 $R^{12}$;

alternatively, R[7] and R[8] together with the carbon atom to which they are attached forms a $C_3$-$C_6$cycloalkyl or a 3-10 membered hetcycloalkyl ring optionally substituted with 0-3 $R^{12}$;

R[9] and R[10] are selected from hydrogen, halo, cyano, trihalomethyl, trihalomethyloxy, $C_1$-$C_6$alkyl, $C_3$-$C_6$cycloalkyl, 3-10 membered hetcycloalkyl, aryl, hetaryl, aryl$C_1$-$C_6$alkyl, hetaryl$C_1$-$C_6$alkyl, —C(O)$R^6$, —S(O)$_n$$R^6$, —S(O)$_n$$NR^4R^5$, —N($R^4$)S(O)$_n$$R^6$, —N($R^4$)C(O)$NR^4R^5$, OH, oxo, $C_1$-$C_6$alkyloxy, aryl$C_1$-$C_6$alkyloxy, hetaryl$C_1$-$C_6$alkyloxy, $C_1$-$C_6$alkyloxo$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, cycloalkyl and aryl/hetaryl group is optionally substituted with 0-3 $R^{12}$;

alternatively, R[9] and R[10] together with the carbon atom to which they are attached forms a $C_3$-$C_6$cycloalkyl or a 3-10 membered hetcycloalkyl ring optionally substituted with 0-3 $R^{12}$; R[11] is selected from halo, cyano, trihalomethyl, trihalomethyloxy, $C_1$-$C_6$alkyl, $C_3$-$C_6$cycloalkyl, 3-10 membered hetcycloalkyl, $C_3$-$C_6$-spirocycloalkyl, 3-6 membered spirohetcycloalkyl, aryl, hetaryl, aryl$C_1$-$C_6$alkyl, hetaryl$C_1$-$C_6$alkyl, —C(O)$R^6$, —S(O)$_n$$R^6$, —S(O)$_n$$NR^4R^5$, —N($R^4$)S(O)$_n$$R^6$, —N($R^4$)C(O)$NR^4R^5$, OH, oxo, $C_1$-$C_6$alkyloxy, aryl$C_1$-$C_6$alkyloxy, hetaryl$C_1$-$C_6$alkyloxy, $C_1$-$C_6$alkyloxo$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, cycloalkyl and aryl/hetaryl group is optionally substituted with 0-3 $R^{12}$;

R[11] is selected from halo, hydroxy, oxo, —COOH, —S(O)$_n$ $R^{13}$, cycloalkyl, —$OR^{13}$, $C_1$-$C_6$alkyl, $C_1$-$C_6$alkyloxy, aryl and hetaryl, wherein $R^{13}$ is $C_1$-$C_6$alkyl; and wherein each alkyl, cycloalkyl and aryl, hetaryl group is optionally substituted with 0-3 $R^{12}$;

R[12] is selected from halo, OH, oxo, COOH, cyano, $C_1$-$C_6$alkyloxy, trihalomethyl, $C_3$-$C_{10}$-cycloalkyloxy, aryloxy, hetaryloxy, hetarylthio and aryl$C_1$-$C_6$alkyloxy;

or a salt thereof with a pharmaceutically acceptable acid or base, or any optical isomer or mixture of optical isomers, including a racemic mixture, or any tautomeric forms.

In another aspect of the invention, $R^2$ is selected from:

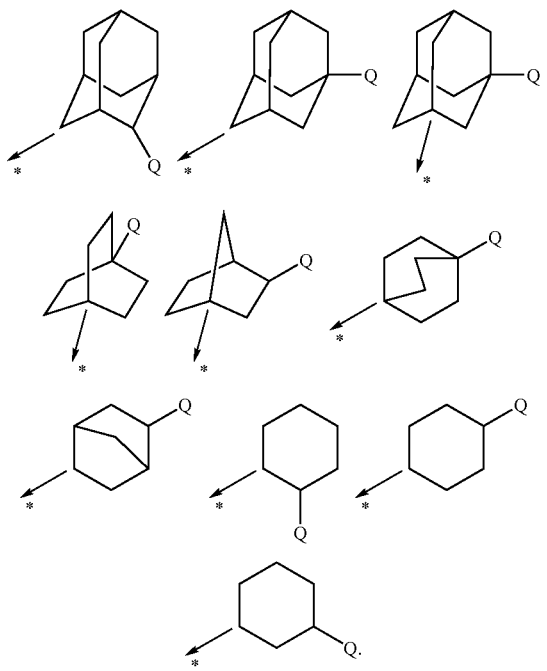

In another aspect of the invention, $R^2$ is selected from:

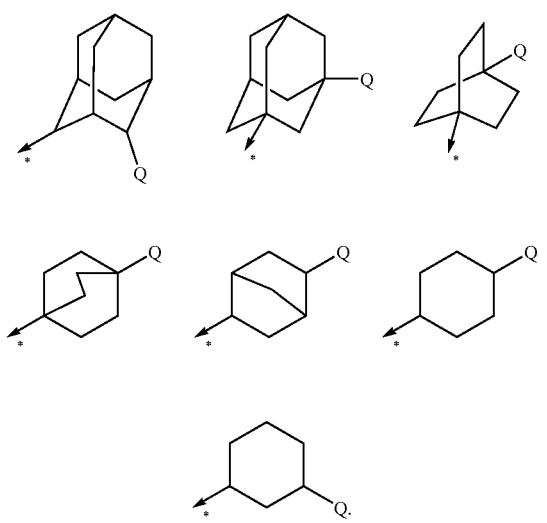

In another aspect of the invention, $R^2$ is selected from:

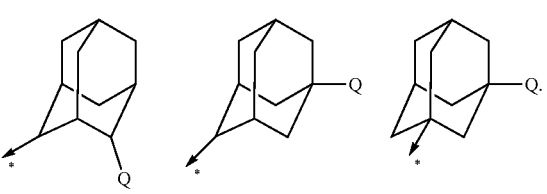

In another aspect of the invention, $R^2$ is

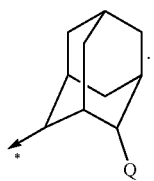

In another aspect of the invention, $R^2$ is

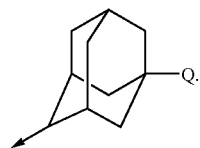

In another aspect of the invention, $R^2$ is

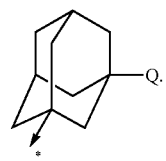

In another aspect of the invention, $R^2$ is selected from:

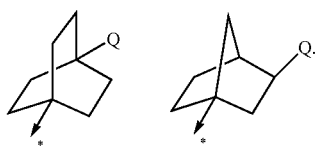

In another aspect of the invention, $R^2$ is

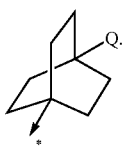

In another aspect of the invention, $R^2$ is

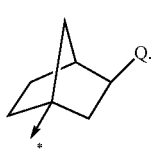

In another aspect of the invention, $R^2$ is selected from:

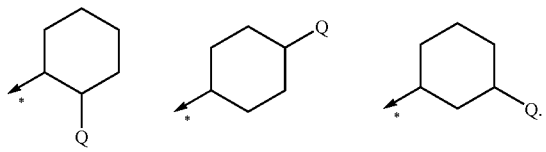

In another aspect of the invention, $R^2$ is

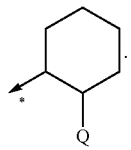

In another aspect of the invention, $R^2$ is

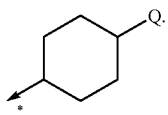

In another aspect of the invention, $R^2$ is

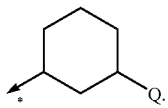

In another aspect of the invention, $R^2$ is

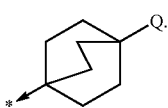

In another aspect of the invention, $R^2$ is

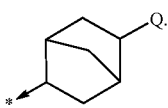

In another aspect of the invention, $R^2$ is

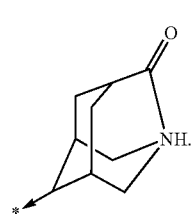

In another aspect of the invention, $R^2$ is

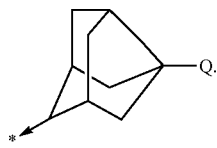

In another aspect of the invention, $R^2$ is selected form $C_1$-$C_6$alkyl, $C_3$-$C_{10}$cycloalkyl, aryl, hetaryl, aryl$C_1$-$C_6$alkyl, and hetaryl$C_1$-$C_6$alkyl, wherein each of the alkyl, cycloalkyl, aryl, and hetaryl groups are independently substituted with 0-2 $R^{11}$.

In another aspect of the invention, $R^2$ is selected form $C_1$-$C_6$alkyl and $C_3$-$C_{10}$cycloalkyl, each of which is substituted with 0-2 $R^{11}$.

In another aspect of the invention, $R^2$ is selected from aryl and hetaryl, each of which is substituted with 0-2 $R^{11}$.

In another aspect of the invention, $R^2$ is selected form aryl$C_1$-$C_6$alkyl and hetaryl$C_1$-$C_6$alkyl, each of which is substituted with 0-2 $R^{11}$.

In another aspect of the invention, $R^1$ and $R^2$ together with the nitrogen to which they are attaced attached, is selected from the following structural elements:

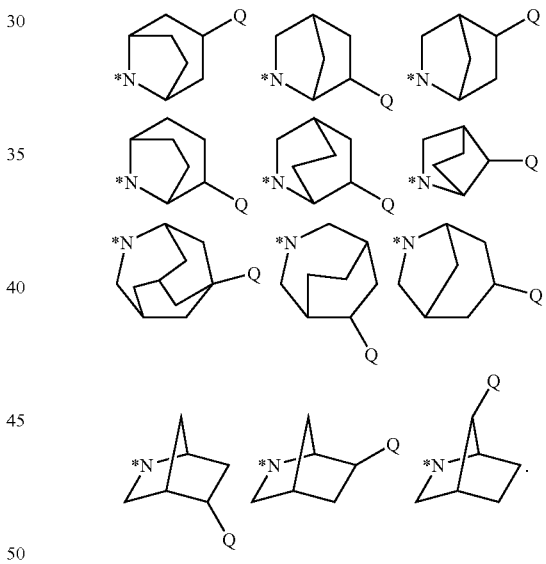

In another aspect of the invention, $R^1$ and $R^2$ together with the nitrogen to which they are attaced attached, is selected from the following structural elements:

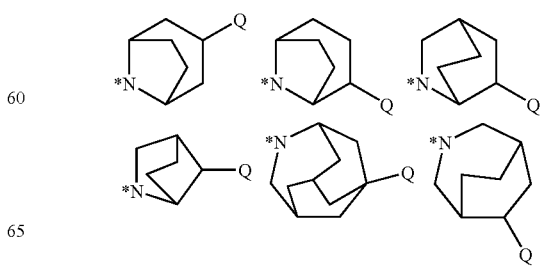

-continued

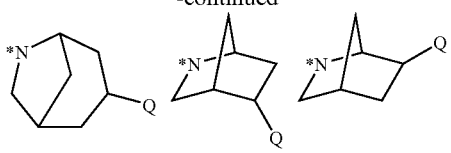

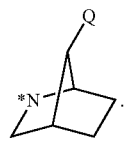

In another aspect of the invention, R¹ and R² together with the nitrogen to which they are attaced is:

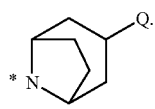

In another aspect of the invention R¹ and R² together with the nitrogen to which they are attaced is:

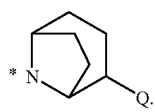

In another aspect of the invention R¹ and R² together with the nitrogen to which they are attaced is:

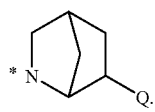

In another aspect of the invention R¹ and R² together with the nitrogen to which they are attaced is:

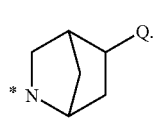

In another aspect of the invention R¹ and R² together with the nitrogen to which they are attaced is:

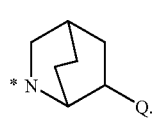

In another aspect of the invention R¹ and R² together with the nitrogen to which they are attaced is:

In another aspect of the invention R¹ and R² together with the nitrogen to which they are attaced is:

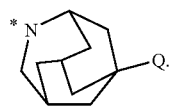

In another aspect of the invention R¹ and R² together with the nitrogen to which they are attaced is:

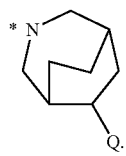

In another aspect of the invention R¹ and R² together with the nitrogen to which they are attaced is:

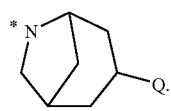

In another aspect of the invention R¹ and R² together with the nitrogen to which they are attaced is:

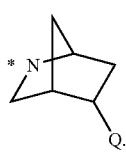

In another aspect of the invention R¹ and R² together with the nitrogen to which they are attaced is:

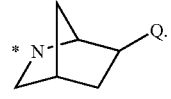

In another aspect of the invention R¹ and R² together with the nitrogen to which they are attaced is:

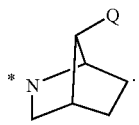

In another aspect of the invention, R¹ and R² together with the nitrogen to which they are attaced, form a 5-12 membered saturated or partially saturated monocyclic, bicyclic, or tricyclic ring consisting of the shown nitrogen, 4-10 carbon atoms, and 0-2 additional heteroatoms selected from nitrogen, oxygen, and $S(O)_m$, wherein this ring is substituted with 0-3 groups selected from $C_1$-$C_6$alkyl, aryl, hetaryl, aryl$C_1$-$C_6$alkyl, hetaryl$C_1$-$C_6$-alkyl, wherein the alkyl, aryl and hetaryl groups are optionally substituted with 0-3 $R^{11}$.

In another aspect of the invention, R¹ and R² together with the nitrogen to which they are attaced, form a pyrrolinyl, pyrrolidinyl, 2-imidazolinyl, imidazolidinyl, 2-pyrazolinyl, piperidinyl, piperazinyl wherein each ring is substituted with 0-3 groups selected from $C_1$-$C_6$alkyl, aryl, hetaryl, aryl$C_1$-$C_6$alkyl, hetaryl$C_1$-$C_6$alkyl, wherein the alkyl, aryl and hetaryl groups are optionally substituted with 0-3 $R^{11}$.

In another aspect of the invention, R³ is selected from $C_3$-$C_{10}$cycloalkyl or 3-10 membered heterocycloalkyl each of which is substituted with 0-3 $R^{11}$.

In another aspect of the invention, R³ is selected from aryl or hetaryl, each of which is substituted with 0-3 $R^{11}$.

In another aspect of the invention, R³ is selected from phenyl which is optionally substituted with halogen.

In another aspect of the invention, R³ is selected from pyridinyl or pyridazinyl.

In another aspect of the invention, Q is selected from hydroxy, carboxy, —$SO_2R^6$, $C_1$-$C_6$alkyl, $C_3$-$C_6$cycloalkyl or —$C(O)R^6$; wherein the alkyl and cycloalkyl groups are optionally substituted with hydroxy, —OC(=O)CH₃ or —C(=O)OCH₃.

In another aspect of the invention, Q is selected from hydroxy, carboxy, $C_1$-$C_6$alkyl, $C_3$-$C_6$cycloalkyl or —C(O)R⁶; wherein the alkyl, and cycloalkyl groups are optionally substituted with hydroxy.

In another aspect of the invention, Q is $C_1$-$C_6$alkyl, optionally substituted with —OC(=O)CH₃ or —C(=O)OCH₃.

In another aspect of the invention, Q is hydroxy.

In another aspect of the invention, Q is carboxy.

In another aspect of the invention, X is a chemical bond.

In another aspect of the invention, X is $S(O)_n$.

In another aspect of the invention, Y is O.

In another aspect of the invention, Y is S.

In another aspect of the invention, m is 0.

In another aspect of the invention, m is 1.

In another aspect of the invention, m is 2.

In another aspect of the invention, n is 1.

In another aspect of the invention, n is 2.

In another aspect of the invention, $R^{11}$ is halogen.

In another aspect, the present invention provides for a compound of formula (Ia):

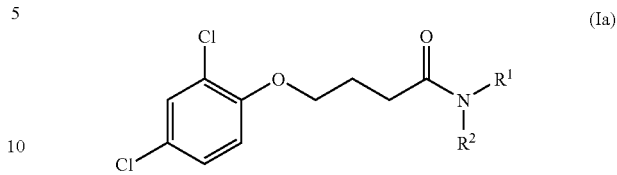

In another aspect, the present invention provides for a compound of formula (Ib):

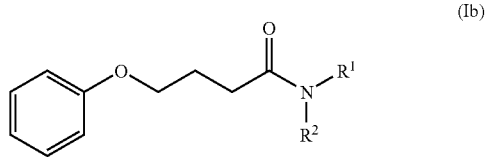

In another aspect, the present invention provides for a compound of formula (Ic):

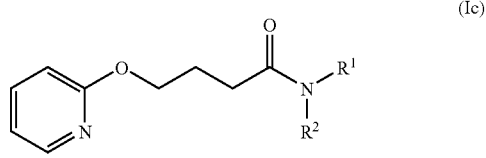

In another aspect, the present invention provides for a compound of formula (Id):

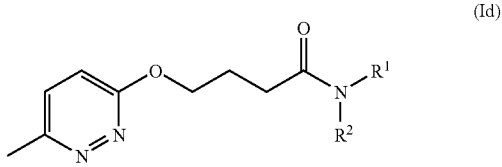

In another aspect, the present invention provides for a compound of formula (Ie):

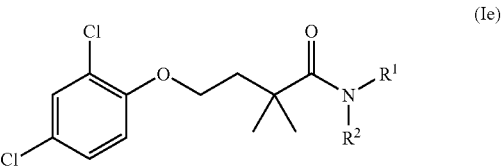

In another aspect, the present invention provides for a compound of formula (If):

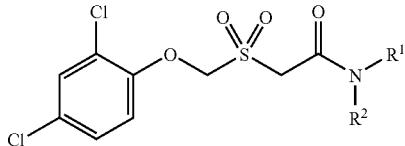
(If)

In another aspect of the invention, a compound is selected from the group consisting of:

1-[2-(4-Chloro-phenyl)-pyrrolidin-1-yl]-4-(2,4-dichloro-phenoxy)-butan-1-one;
N-(Cyclopropyl-phenyl-methyl)-4-(2,4-dichloro-phenoxy)-butyramide;
1-[2-(2-Chloro-phenyl)-piperidin-1-yl]-4-(2,4-dichloro-phenoxy)-butan-1-one;
4-(2,4-Dichloro-phenoxy)-N-(1-phenyl-cyclobutyl)-butyramide;
4-(2,4-Dichloro-phenoxy)-N-(1-phenyl-cyclopropyl)-butyramide;
4-(2,4-Dichloro-phenoxy)-N-[1-(3-trifluoromethyl-phenyl)-cyclopropyl]butyramide;
N-[1-(3-Chloro-phenyl)-cyclobutyl]-4-(2,4-dichloro-phenoxy)-butyramide;
4-(2,4-Dichloro-phenoxy)-1-(4-phenyl-piperidin-1-yl)-butan-1-one;
4-(2,4-Dichloro-phenoxy)-1-(2-phenyl-piperidin-1-yl)-butan-1-one;
4-(2,4-Dichloro-phenoxy)-N-((1S,2R,5S)-6,6-dimethyl-bicyclo[3.1.1]hept-2-ylmethyl)butyramide;
N-[(1R,2R)-2-(4-Chloro-phenyl)-cyclopentyl]-4-(2,4-dichloro-phenoxy)-butyramide;
N-[(1R,2S)-2-(4-Chloro-phenyl)-cyclopentyl]-4-(2,4-dichloro-phenoxy)-butyramide;
4-(2,4-Dichloro-phenoxy)-N-(2-phenyl-cyclopentyl)-butyramide;
1-(3-Aza-bicyclo[3.2.2]-non-3-yl)-4-(2,4-di-chloro-phenoxy)-butan-1-one;
(1S,2R,3S,4R)-3-[4-(2,4-Dichloro-phenoxy)-butyrylamino]bicyclo-[2.2.1]heptane-2-carboxylic acid ethyl ester;
8-[4-(2,4-Dichloro-phenoxy)-butyryl]-8-aza-bicyclo[3.2.1]octane-3-carboxylic acid methyl ester;
N-Cyclopropyl-4-(2,4-dichloro-phenoxy)-N-(5-hydroxy-adamantan-2-yl)-butyramide;
N-Cyclopropyl-4-(2,4-dichloro-phenoxy)-N-(5-hydroxy-adamantan-2-yl)-butyramide;
4-(2,4-Dichloro-phenoxy)-N-(5-hydroxy-adamantan-2-yl)-2,2,N-trimethyl-butyramide;
3-[4-(2,4-Dichloro-phenoxy)-butyrylamino]-adamantane-1-carboxylic acid;
4-(2,4-Dichloro-phenoxy)-N-(5-hydroxy-methyl-adamantan-2-yl)-2,2-dimethyl-butyramide;
4-(2,4-Dichloro-phenoxy)-N-(5-hydroxy-adamantan-2-yl)-2,2-dimethyl-butyramide;
4-(2,4-Dichloro-phenoxy)-N-(4-hydroxy-methyl-adamantan-2-yl)-butyramide;
4-(2,4-Dichloro-phenoxy)-1-(1-hydroxy-4-aza-tricyclo[4.3.1.1{3,8}]undec-4-yl)-butan-1-one;
4-(2,4-Dichloro-phenoxy)-1-(3-hydroxy-8-aza-bicyclo[3.2.1]oct-8-yl)-2,2-dimethyl-butan-1-one;
1-[2-(2,4-Dichloro-phenoxy)-ethyl]cyclo-propanecarboxylic acid (5-hydroxy-adamantan-2-yl)-amide;
2-(2,4-Dichloro-phenoxy-methanesulfonyl)-N-(5-hydroxy-adamantan-2-yl)-N-methylacetamide;
2-(2,4-Dichloro-phenoxy-methanesulfonyl)-N-(3-hydroxymethyl-adamantan-1-yl)-acetamide;
Acetic acid 3-[2-(2,4-dichloro-phenoxy-methanesulfonyl)-acetylamino]-adamantan-1-ylmethyl ester;
4-(2,4-Dichloro-phenoxy)-1-(6-hydroxy-2-aza-bicyclo[2.2.1]hept-2-yl)-butan-1-one;
4-(2,4-Dichloro-phenoxy)-1-(5-hydroxy-2-aza-bicyclo[2.2.1]hept-2-yl)-butan-1-one;
4-(2,4-Dichloro-phenoxy)-1-(3-hydroxy-6-aza-bicyclo[3.2.1]oct-6-yl)-butan-1-one;
4-(2,4-Dichloro-phenoxy)-N-(4-hydroxy-cyclohexyl)-N-methyl-butyramide;
4-(2,4-Dichloro-phenoxy)-N-(5-hydroxy-adamantan-2-yl)-butyramide;
4-(2,4-Dichloro-phenoxy)-N-(3-hydroxy-methyl-adamantan-1-yl)-butyramide;
4-(2,4-Dichloro-phenoxy)-1-(7-hydroxy-2-aza-bicyclo[2.2.1]hept-2-yl)-butan-1-one;
3-[4-(2,4-Dichloro-phenoxy)-butyrylamino]-adamantane-1-carboxylic acid methyl ester;
3-[4-(2,4-Dichloro-phenoxy)-butyrylamino]-adamantane-1-carboxylic acid;
4-(2,4-Dichloro-phenoxy)-N-(5-hydroxy-adamantan-2-yl)-N-methyl-butyramide;
4-(2,4-Dichloro-phenoxy)-N-ethyl-N-(5-hydroxy-adamantan-2-yl)-butyramide;
4-(2,4-Dichloro-phenoxy)-N-ethyl-N-(5-hydroxy-adamantan-2-yl)-butyramide;
4-(2,4-Dichloro-phenoxy)-1-(8-hydroxy-3-aza-bicyclo[3.2.1]oct-3-yl)-butan-1-one;
4-(2,4-Dichloro-phenoxy)-1-(5-hydroxy-2-aza-bicyclo[2.2.2]oct-2-yl)-butan-1-one;
N-(4-Hydroxy-cyclohexyl)-N-methyl-4-phenoxy-butyramide;
N-(5-Hydroxy-adamantan-2-yl)-4-phenoxy-butyramide;
N-(5-Hydroxy-adamantan-2-yl)-4-phenoxy-butyramide;
1-(5-Hydroxy-2-aza-bicyclo[2.2.2]oct-2-yl)-4-phenoxy-butan-1-one;
1-(8-Hydroxy-3-aza-bicyclo[3.2.1]oct-3-yl)-4-phenoxy-butan-1-one;
N-(5-Hydroxy-adamantan-2-yl)-N-methyl-4-phenoxy-butyramide;
N-(5-Hydroxy-adamantan-2-yl)-N-methyl-4-phenoxy-butyramide;
1-(3-Hydroxy-6-aza-bicyclo[3.2.1]oct-6-yl)-4-phenoxy-butan-1-one;
N-(3-Hydroxymethyl-adamantan-1-yl)-4-phenoxy-butyramide;
1-(5-Hydroxy-2-aza-bicyclo[2.2.1]hept-2-yl)-4-phenoxy-butan-1-one;
1-(6-Hydroxy-2-aza-bicyclo[2.2.1]hept-2-yl)-4-phenoxy-butan-1-one;
1-(7-Hydroxy-2-aza-bicyclo[2.2.1]hept-2-yl)-4-phenoxy-butan-1-one;
N-(5-Hydroxy-adamantan-2-yl)-N-isopropyl-4-phenoxy-butyramide;
N-Ethyl-N-(5-hydroxy-adamantan-2-yl)-4-phenoxy-butyramide;
N-Ethyl-N-(5-hydroxy-adamantan-2-yl)-4-phenoxy-butyramide;
3-(4-Phenoxy-butyryl-amino)adamantane-1-carboxylic acid methyl ester;
3-(4-Phenoxy-butyryl-amino)adamantane-1-carboxylic acid;

N-(5-Hydroxymethyl-adamantan-2-yl)-4-phenoxy-butyramide;
4-(2,4-Dichloro-phenoxy)-N-(5-hydroxy-methyl-adamantan-2-yl)-butyramide;
4-(2,4-Dichloro-phenoxy)-N-(5-hydroxy-adamantan-2-yl)-N-isopropyl-butyramide;
4-(2,4-Dichloro-phenoxy)-N-((1S,2S)-2-hydroxy-cyclohexyl)-N-methyl-butyramide;
3-{[4-(2,4-Dichloro-phenoxy)-butyryl]-methyl-amino}-cyclo-hexanecarboxylic acid;
4-(2,4-Dichloro-phenoxy)-N-(3-hydroxy-methyl-cyclohexyl)-N-methyl-butyramide;
4-(2,4-Dichloro-phenoxy)-N-(4-hydroxy-methyl-cyclohexyl)-N-methyl-butyramide;
4-(2,4-Dichloro-phenoxy)-N-(3-hydroxy-cyclohexyl)-N-methyl-butyramide;
4-(2,4-Dichloro-phenoxy)-N—((S)-2-hydroxymethyl-cyclo-hexyl)-N-methyl-butyramide;
(S)-2-{(R)-[4-(2,4-Dichloro-phenoxy)-butyryl]methyl-amino}-cyclohexanecarboxylic acid;
4-(2,4-Dichloro-phenoxy)-N-(5-hydroxy-bicyclo[2.2.1]hept-2-yl)-N-methyl-butyramide;
4-(2,4-Dichloro-phenoxy)-N-(5-hydroxy-methyl-adamantan-2-yl)-N-methyl-butyramide;
4-[4-(2,4-Dichloro-phenoxy)-butyryl]-4-aza-tricyclo[4.3.1.1{3,8}]undecane-1-carboxylic acid methyl ester;
4-[4-(2,4-Dichloro-phenoxy)-butyryl]-4-aza-tricyclo[4.3.1.1{3,8}]undecane-1-carboxylic acid;
4-[4-(2,4-Dichloro-phenoxy)-butyrylamino]-adamantane-1-carboxylic acid methyl ester;
4-(2,4-Dichloro-phenoxy)-N-methyl-N-(4-sulfamoyl-cyclohexyl)-butyramide;
4-(2,4-Dichloro-phenoxy)-N-(4-dimethyl-sulfamoyl-cyclohexyl)-N-methyl-butyramide;
4-(2,4-Dichloro-phenoxy)-N-(4-dimethyl-sulfamoyl-cyclohexyl)-N-methyl-butyramide;
4-[4-(2,4-Dichloro-phenoxy)-butyrylamino]bicyclo[2.2.2]octane-1-carboxylic acid ethyl ester;
4-(2,4-Dichloro-phenoxy)-N-(4-hydroxy-methyl-bicyclo[2.2.2]oct-1-yl)-butyramide;
4-{[4-(2,4-Dichloro-phenoxy)-butyryl]-methyl-amino}-cyclo-hexanecarboxylic acid;
4-(2,4-Dichloro-phenoxy)-N-(4-hydroxy-methyl-cyclohexyl)-butyramide;
4-{[4-(2,4-Dichloro-phenoxy)-butyryl]-methyl-amino}-cyclo-hexanecarboxylic acid amide;
4-{[4-(2,4-Dichloro-phenoxy)-butyryl]-methyl-amino}-cyclo-hexanecarboxylic acid dimethylamide;
4-(2,4-Dichloro-phenoxy)-N-[4-(1-hydroxy-1-methyl-ethyl)-cyclohexyl]-N-methyl-butyramide;
4-(2,4-Dichloro-phenoxy)-N-[4-(1-hydroxy-1-methyl-ethyl)-cyclohexyl]butyramide;
5-{[4-(2,4-Dichloro-phenoxy)-butyryl]-methyl-amino}-bicyclo[2.2.1]heptane-2-carboxylic acid ethyl ester;
4-(2,4-Dichloro-phenoxy)-N-[5-(1-hydroxy-1-methyl-ethyl)-adamantan-2-yl]-N-methyl-butyramide;
4-(2,4-Dichloro-phenoxy)-N-[5-(1-hydroxy-1-methyl-ethyl)-adamantan-2-yl]-N-methyl-butyramide;
4-(2,4-Dichloro-phenoxy)-N-[5-(1-hydroxy-1-methyl-ethyl)-adamantan-2-yl]butyramide;
4-(2,4-Dichloro-phenoxy)-N-(5-hydroxymethyl-adamantan-2-yl)-N-methyl-butyramide;
N-(5-Hydroxy-adamantan-2-yl)-4-(4-methane-sulfonyl-phenoxy)-butyramide
N-(5-Hydroxy-adamantan-2-yl)-4-(pyridin-2-yloxy)-butyramide;
N-(5-Hydroxy-adamantan-2-yl)-4-(pyridin-2-yloxy)-butyramide;
N-(5-Hydroxy-adamantan-2-yl)-4-(6-methyl-pyridazin-3-yloxy)-butyramide;
N-(5-Hydroxy-adamantan-2-yl)-4-(6-methyl-pyridazin-3-yloxy)-butyramide;
4-(2,4-Dichloro-phenoxy)-N-(4-methane-sulfonyl-cyclohexyl)-N-methyl-butyramide;
4-(2,4-Dichloro-phenoxy)-N-(4-methane-sulfonyl-cyclohexyl)-N-methyl-butyramide;
4-(2,4-Dichloro-phenoxy)-N-(5-hydroxy-methyl-bicyclo[2.2.2]oct-2-yl)-N-methyl-butyramide;
4-(2,4-Dichloro-phenoxy)-N-((1R,3S,5R,7S)-3-hydroxy-adamantan-1-yl)-butyramide; or a salt thereof with a pharmaceutically acceptable acid or base, or any optical isomer or mixture of optical isomers, including a racemic mixture, or any tautomeric forms.

In another embodiment, the present invention provides for the novel preparation of a pharmaceutical composition for the treatment of conditions, disorders, or diseases wherein a modulation or an inhibition of the activity of 11βHSD1 is beneficial.

In another embodiment, the present invention provides for the novel preparation of a pharmaceutical composition, wherein: the conditions, disorders, and diseases that are influenced by intracellular glucocorticoid levels.

In another embodiment, the present invention provides for the novel preparation of a pharmaceutical composition, wherein: the conditions, disorders, or diseases are selected from metabolic syndrome, insulin resistance, dyslipidemia, hypertension, obesity, type 2 diabetes, impaired glucose tolerance (IGT), impaired fasting glucose (IFG), the progression from IGT to type 2 diabetes, the progression of the metabolic syndrome into type 2 diabetes, diabetic late complications, neurodegenerative and psychiatric disorders, and the adverse effects of glucocorticoid receptor agonist treatment or therapy.

In another embodiment, the present invention provides for the novel preparation of a pharmaceutical composition, wherein: the pharmaceutical composition is suitable for a route of administration selected from oral, nasal, buccal, transdermal, pulmonal, and parenteral.

In another embodiment, the present invention provides a novel method for the treatment of conditions, disorders, or diseases wherein a modulation or an inhibition of the activity of 11βHSD1 is beneficial, the method comprising administering to a subject in need thereof an effective amount of a compound of the present invention.

In another embodiment, the present invention provides a novel method wherein the conditions, disorders, and diseases that are influenced by intracellular glucocorticoid levels.

In another embodiment, the present invention provides a novel method wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), progression from IGT to type 2 diabetes, progression of metabolic syndrome into type 2 diabetes, diabetic late complications, neurodegenerative and psychiatric disorders, and the adverse effects of glucocorticoid receptor agonist treatment or therapy.

In another embodiment, the present invention provides a novel method wherein the administering is via a route selected from oral, nasal, buccal, transdermal, pulmonal, and parenteral.

In another embodiment, the present invention provides a novel compound, which is an agent useful for the treatment of conditions, disorders, or diseases wherein a modulation or an inhibition of the activity of 11βHSD1 is beneficial.

In another embodiment, the present invention provides a novel method wherein the conditions, disorders, and diseases that are influenced by intracellular glucocorticoid levels.

In another embodiment, the present invention provides a novel method wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), progression from IGT to type 2 diabetes, progression of metabolic syndrome into type 2 diabetes, diabetic late complications, neurodegenerative and psychiatric disorders, and the adverse effects of glucocorticoid receptor agonist treatment or therapy.

In another embodiment, the present invention provides a novel method pharmaceutical composition comprising, as an active ingredient, at least one compound according of the present invention together with one or more pharmaceutically acceptable carriers or excipients.

In another embodiment, the present invention provides a novel pharmaceutical composition, which is suitable for oral, nasal, buccal, transdermal, pulmonal, or parenteral administration.

The compounds of the present invention have asymmetric centers and may occur as racemates, racemic mixtures, and as individual enantiomers or diastereoisomers, with all isomeric forms being included in the present invention as well as mixtures thereof.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, and nitric acids. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, and ketoglutarates. Further examples of pharmaceutically acceptable inorganic or organic acid addition salts include the pharmaceutically acceptable salts listed in J. Pharm. Sci., 66, 2 (1977), which is incorporated herein by reference. Examples of metal salts include lithium, sodium, potassium, barium, calcium, magnesium, zinc, and calcium salts. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylene-diamine, N-benzylphenylethylamine, N-methyl-D-glucamine, and guanidine. Examples of cationic amino acids include lysine, arginine, and histidine.

Further, some of the compounds of the present invention may form solvates with water or common organic solvents. Such solvates are encompassed within the scope of the invention.

The pharmaceutically acceptable salts are prepared by reacting a compound of the present invention with 1 to 4 equivalents of a base such as sodium hydroxide, sodium methoxide, sodium hydride, potassium tert-butoxide, calcium hydroxide, and magnesium hydroxide, in solvents such as ether, THF, methanol, tert-butanol, dioxane, and isopropanol, ethanol. Mixtures of solvents may be used. Organic bases such as lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, and tartaric acid in solvents such as ethyl acetate, ether, alcohols, acetone, THF, and dioxane. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, and lactic acid, wherever applicable or chiral bases such as brucine, (R)- or (S)-phenylethylamine, cinchona alkaloids and their derivatives. Commonly used methods are compiled by Jaques et al. in "Enantiomers, Racemates and Resolution" (Wiley Interscience, 1981). More specifically the compound of the present invention may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of the compounds forming part of this invention may be prepared by crystallization of said compounds under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, it spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the present invention. Conventional procedures for the selection and preparation of suitable prodrug derivatives are described, for example, in "Design of Prodrugs", ed. H. Bundgaard, Elsevier, 1985.

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver and/or poor uptake in cells. Although the factors determining bioavailability are not completely understood, there are many examples in the scientific literature—well known to those skilled in the art of how to modify compounds, which are potent and selective in biochemical assays but show low or no activity in vivo, into drugs that are biologically active.

It is within the scope of the invention to modify the compounds of the present invention, termed the 'original compound', by attaching chemical groups that will improve the bioavailability of said compounds in such a way that the uptake in cells or mammals is facilitated.

Examples of said modifications, which are not intended in any way to limit the scope of the invention, include changing of one or more carboxy groups to esters (for instance methyl esters, ethyl esters, tert-butyl, acetoxymethyl, pivaloyloxymethyl esters or other acyloxymethyl esters). Compounds of the invention, original compounds, such modified by attaching chemical groups are termed 'modified compounds'.

The invention also encompasses active metabolites of the present compounds.

The compounds according to the invention alter, and more specifically, reduce the level of active intracellular glucocorticoid and are accordingly useful for the treatment of conditions, disorders, and diseases in which such a modulation or reduction is beneficial.

Accordingly, the present compounds may be applicable for the treatment of the metabolic syndrome, insulin resistance, dyslipidemia, hypertension, obesity, type 2 diabetes, impaired glucose tolerance (IGT), impaired fasting glucose (IFG), Latent Autoimmune Diabetes in the Adult (LADA), type 1 diabetes, diabetic late complications including cardiovascular diseases, cardiovascular disorders, disorders of lipid metabolism, neurodegenerative and psychiatric disorders, dysregulation of intraocular pressure including glaucoma, immune disorders, inappropriate immune responses, musculo-skeletal disorders, gastrointestinal disorders, polycystic ovarie syndrome (PCOS), reduced hair growth or other diseases, disorders or conditions that are influenced by intracellular glucocorticoid levels, adverse effects of increased blood levels of active endogenous or exogenous gluco-corticoid, and any combination thereof, adverse effects of increased plasma levels of endogenous active glucocorticoid, Cushing's disease, Cushing's syndrome, adverse effects of gluco-corticoid receptor agonist treatment of autoimmune diseases, adverse effects of gluco-corticoid receptor agonist treatment of inflammatory diseases, adverse effects of glucocorticoid receptor agonist treatment of diseases with an inflammatory component, adverse effects of glucocorticoid receptor agonist treatment as a part of cancer chemotherapy, adverse effects of glucocorticoid receptor agonist treatment for surgical/post-surgical or other trauma, adverse effects of glucocorticoid receptor agonist therapy in the context of organ or tissue transplantation or adverse effects of glucocorticoid receptor agonist treatment in other diseases, disorders or conditions where glucocorticoid receptor agonists provide clinically beneficial effects.

More specifically the present compounds may be applicable for the treatment of the metabolic syndrome, type 2 diabetes, diabetes as a consequence of obesity, insulin resistance, hyperglycemia, prandial hyperglycemia, hyperinsulinemia, inappropriately low insulin secretion, impaired glucose tolerance (IGT), impaired fasting glucose (IFG), increased hepatic glucose production, type 1 diabetes, LADA, pediatric diabetes, dyslipidemia, diabetic dyslipidemia, hyperlipidemia, hypertriglyceridemia, hyperlipoproteinemia, hypercholesterolemia, decreased HDL cholesterol, impaired LDL/HDL ratio, other disorders of lipid metabolism, obesity, visceral obesity, obesity as a consequence of diabetes, increased food intake, hypertension, diabetic late complications, micro-/macroalbuminuria, nephropathy, retinopathy, neuropathy, diabetic ulcers, cardiovascular diseases, arteriosclerosis, atherosclerosis, coronary artery disease, cardiac hypertrophy, myocardial ischemia, heart insufficiency, congestive heart failure, stroke, myocardial infarction, arrythmia, decreased blood flow, erectile dysfunction (male or female), myopathy, loss of muscle tissue, muscle wasting, muscle catabolism, osteoporosis, decreased linear growth, neurodegenerative and psychiatric disorders, Alzheimers disease, neuronal death, impaired cognitive function, depression, anxiety, eating disorders, appetite regulation, migraine, epilepsy, addiction to chemical substances, disorders of intraocular pressure, glaucoma, polycystic ovary syndrome (PCOS), inappropriate immune responses, inappropriate T helper-1/T helper-2 polarisation, bacterial infections, mycobacterial infections, fungal infections, viral infections, parasitic infestations, suboptimal responses to immunizations, immune dysfunction, partial or complete baldness, or other diseases, disorders or conditions that are influenced by intracellular glucocorticoid levels and any combination thereof, adverse effects of gluco-corticoid receptor agonist treatment of allergic-inflammatory diseases such as asthma and atopic dermatitis, adverse effects of glucocorticoid receptor agonist treatment of disorders of the respiratory system e.g., asthma, cystic fibrosis, emphysema, bronchitis, hypersensitivity, pneumonitis, eosinophilic pneumonias, pulmonary fibrosis, adverse effects of gluco-corticoid receptor agonist treatment of inflammatory bowel disease such as Crohn's disease and ulcerative colitis; adverse effects of glucocorticoid receptor agonist treatment of disorders of the immune system, connective tissue and joints e.g., reactive arthritis, rheumatoid arthritis, Sjögren's syndrome, systemic lupus erythematosus, lupus nephritis, Henoch-Schölein purpura, Wegener's granulomatosis, temporal arteritis, systemic sclerosis, vasculitis, sarcoidosis, dermatomyositis-polymyositis, pemphigus vulgaris; adverse effects of glucocorticoid receptor agonist treatment of endocrinological diseases such as hyperthyroidism, hypoaldosteronism, hypopituitarism; adverse effects of glucocorticoid receptor agonist treatment of hematological diseases e.g., hemolytic anemia, thrombocytopenia, paroxysmal nocturnal hemoglobinuria; adverse effects of glucocorticoid receptor agonist treatment of cancer such as spinal cord diseases, neoplastic compression of the spinal cord, brain tumours, acute lymphoblastic leukemia, Hodgkin's disease, chemotherapy-induced nausea, adverse effects of glucocorticoid receptor agonist treatment of diseases of muscle and at the neuro-muscular joint e.g., myasthenia gravis and heriditary myopathies (e.g., Duchenne muscular dystrophy), adverse effects of glucocorticoid receptor agonist treatment in the context of surgery & transplantation e.g., trauma, post-surgical stress, surgical stress, renal transplantation, liver transplantation, lung transplantation, pancreatic islet transplantation, blood stem cell transplantation, bone marrow transplantation, heart transplantation, adrenal gland transplantation, tracheal transplantation, intestinal transplantation, corneal transplantation, skin grafting, keratoplasty, lens implantation and other procedures where immunosuppression with glucocorticoid receptor agonists is beneficial; adverse effects of glucocorticoid receptor agonist treatment of brain absess, nausea/vomiting, infections, hypercalcemia, adrenal hyperplasia, autoimmune hepatitis, spinal cord diseases, saccular aneurysms or adverse effects to glucocorticoid receptor agonist treatment in other diseases, disorders and conditions where glucocorticoid receptor agonists provide clinically beneficial effects.

Accordingly, in a further aspect the invention relates to a compound according to the invention for use as a pharmaceutical composition.

The invention also relates to pharmaceutical compositions comprising, as an active ingredient, at least one compound according to the invention together with one or more pharmaceutically acceptable carriers or diluents.

The pharmaceutical composition preferably in unit dosage form comprises from about 0.05 mg/day to about 2000 mg/day, preferably from about 0.1 mg/day to about 1000 mg/day, and more preferably from about 0.5 mg/day to about 500 mg/day of a compound according to the invention.

In another embodiment, the patient is treated with a compound according to the invention for at least about 1 week, for at least about 2 weeks, for at least about 4 weeks, for at least about 2 months or for at least about 4 months.

In yet another embodiment, the pharmaceutical composition is for oral, nasal, buccal, transdermal, pulmonal or parenteral administration.

Furthermore, the invention relates to the use of a compound according to the invention for the preparation of a pharmaceutical composition for the treatment of disorders and diseases wherein a modulation or an inhibition of the activity of 11βHSD1 is beneficial.

The invention also relates to a method for the treatment of disorders and diseases wherein a modulation or an inhibition of the activity of 11βHSD1 is beneficial, the method comprising administering to a subject in need thereof an effective amount of a compound according to the invention.

In a preferred embodiment of the invention the present compounds are used for the preparation of a medicament for the treatment of any diseases and conditions that are influenced by intracellular glucocorticoid levels as mentioned above.

Thus, in a preferred embodiment of the invention the present compounds are used for the preparation of a medicament for the treatment of conditions and disorders where a decreased level of active intracellular glucocorticoid is desirable, such as the conditions and diseases mentioned above.

In yet a preferred embodiment of the invention the present compounds are used for the preparation of a medicament for the treatment of metabolic syndrome, insulin resistance, dyslipidemia, hypertension obesity, type 2 diabetes, impaired glucose tolerance (IGT), impaired fasting glucose (IFG), progression from IGT to type 2 diabetes, progression of the metabolic syndrome into type 2 diabetes, diabetic late complications (e.g., cardiovascular diseases, arteriosclerosis, and atherosclerosis), neurodegenerative and psychiatric disorders, and, the adverse effects of glucocorticoid receptor agonist treatment or therapy.

In another embodiment of the present invention, the route of administration may be any route which effectively transports a compound according to the invention to the appropriate or desired site of action, such as oral, nasal, buccal, transdermal, pulmonal, or parenteral.

In still a further aspect of the invention the present compounds are administered in combination with one or more further active substances in any suitable ratios. Such further active substances may e.g., be selected from antiobesity agents, antidiabetics, agents modifying the lipid metabolism, antihypertensive agents, glucocorticoid receptor agonists, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor.

In one embodiment of the invention the antiobesity agent is leptin; dexamphetamine or amphetamine; fenfluramine or dexfenfluramine; sibutramine; orlistat; mazindol or phentermine.

Suitable antidiabetic agents include insulin, insulin analogues and derivatives such as those disclosed in EP 792 290 (Novo Nordisk NS), e.g., $N^{\epsilon B29}$-tetradecanoyl des (B30) human insulin, EP 214 826 and EP 705 275 (Novo Nordisk NS), e.g., $Asp^{B28}$ human insulin, U.S. Pat. No. 5,504,188 (Eli Lilly), e.g., $Lys^{B28}$ $Pro^{B29}$ human insulin, EP 368 187 (Aventis), eg Lantus, which are all incorporated herein by reference, GLP-1 (glucagon like peptide-1) and GLP-1 derivatives such as those disclosed in WO 98/08871 to Novo Nordisk NS, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk NS which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as PPARα modulators, PPARδ modulators, cholesterol absorption inhibitors, HSL (hormone-sensitive lipase) inhibitors and HMG CoA inhibitors (statins), nicotinic acid, fibrates, anion exchangers, compounds lowering food intake, bile acid resins, RXR agonists and agents acting on the ATP-dependent potassium channel of the β-cells.

In one embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment the present compounds are administered in combination with a sulphonylurea e.g., tolbutamide, glibenclamide, glipizide or glicazide.

In another embodiment the present compounds are administered in combination with a biguanide e.g., metformin.

In yet another embodiment the present compounds are administered in combination with a meglitinide e.g., repaglinide or senaglinide.

In still another embodiment the present compounds are administered in combination with a thiazolidinedione e.g., troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl] thiazolidine-2,4-dione or a pharmaceutically acceptable salt thereof, preferably the potassium salt.

In yet another embodiment the present compounds may be administered in combination with the insulin sensitizers disclosed in WO 99/19313 such as (−) 3-[4-[2-phen-oxazin-10-yl)ethoxy]phenyl]-2-ethoxypropanoic acid or a pharmaceutically acceptable salts thereof, preferably the arginine salt.

In a further embodiment the present compounds are administered in combination with an α-glucosidase inhibitor e.g., miglitol or acarbose.

In another embodiment the present compounds are administered in combination with an agent acting on the ATP-dependent potassium channel of the β-cells e.g., tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g., cholestyramine, colestipol, clofibrate, gemfibrozil, fenofibrate, bezafibrate, tesaglitazar, EML-4156, LY-818, MK-767, atorvastatin, fluvastatin, lovastatin, pravastatin, simvastatin, acipimox, probucol, ezetimibe or dextrothyroxine.

In a further embodiment the present compounds are administered in combination with more than one of the above-mentioned compounds e.g., in combination with a sulphonylurea and metformin, a sulphonylurea and acarbose, repaglinide and metformin, insulin and a sulphonylurea, insulin and metformin, insulin, insulin and lovastatin, etc.

Further, the present compounds may be administered in combination with one or more antihypertensive agents. Examples of antihypertensive agents are β-blockers such as alprenolol, atenolol, timolol, pindolol, propranolol, metoprolol, bisoprololfumerate, esmolol, acebutelol, metoprolol, acebutolol, betaxolol, celiprolol, nebivolol, tertatolol, oxprenolol, amusolalul, carvedilol, labetalol, β2-receptor blockers e.g., S-atenolol, OPC-1085, ACE (angiotensin converting enzyme) inhibitors such as quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP 00481522), omapatrilat, gemopatrilat and GW-660511, calcium channel blockers such as nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, α-blockers such as doxazosin, urapidil, prazosin, terazosin, bunazosin and OPC-28326, diuretics such as thiazides/sulphonamides (e.g., bendroflumetazide, chlorothalidone, hydrochlorothiazide and clopamide), loopdiuretics (e.g., bumetanide, furosemide and torasemide) and potassium sparing diuretics (e.g., amiloride, spironolactone), endothelin ET-A antagonists such as ABT-546, ambriestan, atrasentan, SB-234551, CI-1034, S-0139 and YM-598, endothelin antagonists e.g., bosentan and J-104133, renin inhibitors such as aliskiren, vasopressin V1 antagonists e.g., OPC-21268, vasopressin V2 antagonists such as tolvaptan, SR-121463 and OPC-31260, B-type natriuretic peptide agonists e.g., Nesiritide, angiotensin II antagonists such as irbesartan, candesartancilexetil, losartan, valsartan, telmisartan, eprosartan, candesartan, CL-329167, eprosartan, iosartan, olmesartan, pratosartan, TA-606, and YM-358, 5-HT2 agonists e.g., fenoldopam and ketanserin, adenosine A1 antagonists such as naftopidil, N-0861 and FK-352, thromboxane A2 antagonists such as KT2-962, endopeptidase inhibitors e.g., ecadotril, nitric oxide agonists such as LP-805, dopamine D1 antagonists e.g., MYD-37, dopamine D2 agonists such as nolomirole, n-3 fatty acids e.g., omacor, prostacyclin agonists such as treprostinil, beraprost, PGE1 agonists e.g., ecraprost, Na+/K+ATPase modulators e.g., PST-2238, Potassium channel activators e.g., KR-30450, vaccines such as PMD-3117, Indapamides, CGRP-unigene, guanylate cyclase stimulators, hydralazines, methyldopa, docarpamine, moxonidine, CoAprovel, MondoBiotech-811.

Further reference can be made to Remington: The Science and Practice of Pharmacy, 19$^{th}$ Edition, Gennaro, Ed., Mack Publishing Co., Easton, Pa., 1995.

Furthermore, the present compounds may be administered in combination with one or more glucocorticoid receptor agonists. Examples of such glucocorticoid receptor agonists are betametasone, dexamethasone, hydrocortisone, methylprednisolone, prednisolone, prednisone, beclomethasone, butixicort, clobetasol, flunisolide, flucatisone (and analogues), momethasone, triamcinolonacetonide, triamcinolonhexacetonide GW-685698, NXC-1015, NXC-1020, NXC-1021, NS-126, P-4112, P-4114, RU-24858 and T-25 series.

It should be understood that any suitable combination of the compounds according to the invention with one or more of the above-mentioned compounds and optionally one or more further pharmacologically active substances are considered to be within the scope of the present invention.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, crèmes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 2000 mg, e.g., from about 0.1 to about 1000 mg, from about 0.5 mg to about 500 mg., from about 1 mg to about 200 mg, e.g., about 100 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which are generally prepared by reacting the free base with a suitable organic or inorganic acid or by reacting the acid with a suitable organic or inorganic base. When a compound for use according to the present invention, contains a free base such salts are prepared in a conventional manner by treating a solution or suspension of the compound with a chemical equivalent of a pharmaceutically acceptable acid. When a compounds for use according to the present invention, contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of suitable carriers are water, salt solutions, alcohols, polyethylene glycols, polyhydroxyethoxylated castor oil, peanut oil, olive oil, syrup, phospholipids, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents.

The pharmaceutical compositions formed by combining the compounds of the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide such as lecithin, or condensation products of an alkyl oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds for use according to the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds for use according to the present invention may form solvates with water or common organic solvents. Such solvates are also encompassed within the scope of the present invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet which may be prepared by conventional tabletting techniques may contain:

Core:

| | |
|---|---|
| Active compound (as free compound or salt thereof) | 5.0 mg |
| Lactosum PH. Eur. | 67.8 mg |
| Cellulose, microcryst. (Avicel) | 31.4 mg |
| Amberlite ® IRP88* | 1.0 mg |
| Magnesii stearas PH. Eur. | q.s. |

Coating:

| | |
|---|---|
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

The compounds of the invention may be administered to a patient which is a mammal, especially a human in need thereof. Such mammals include also animals, both domestic animals, e.g., household pets, and non-domestic animals such as wildlife.

Any novel feature or combination of features described herein is considered essential to this invention.

The present invention also relate to the below methods of preparing the compounds of the invention.

The present invention is further illustrated in the following representative examples which are, however, not intended to limit the scope of the invention in any way.

EXAMPLES, COMPOUNDS OF GENERAL FORMULA (I)

The following examples and general procedures refer to intermediate compounds and final products for general formula (I) identified in the specification and in the synthesis schemes. The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed by either elemental analysis or nuclear magnetic resonance (NMR), where peaks assigned to characteristic protons in the title compounds are presented where appropriate. $^1$H NMR shifts ($\delta_H$) are given in parts per million (ppm) down field from tetramethylsilane as internal reference standard. M.p.: is melting point and is given in ° C. and is not corrected. Column chromatography was carried out using the technique described by W. C. Still et al., *J. Org. Chem.* 43: 2923 (1978) on Merck silica gel 60 (Art. 9385). HPLC analyses are performed using 5 μm C18 4×250 mm column eluted with various mixtures of water and acetonitrile, flow=1 ml/min, as described in the experimental section.

Microwave oven synthesis: The reaction was heated by microwave irradiation in sealed microwave vessels in a single mode Emrys Optimizer EXP from PersonalChemistry®.

Preparative HPLC: Column: 1.9×15 cm Waters XTerra RP-18. Buffer: linear gradient 5-95% in 15 min, MeCN, 0.1% TFA, flow rate of 15 ml/min. The pooled fractions are either evaporated to dryness in vacuo, or evaporated in vacuo until the MeCN is removed, and then frozen and freeze dried.

The abbreviations as used in the examples have the following meaning:
TLC: Thin layer chromatography
CDCl$_3$: Deuterio chloroform
CD$_3$OD: Tetradeuterio methanol
DCM: Dichloromethane
DMF: N,N-dimethylformamide
DMSO-d$_6$: Hexadeuterio dimethylsulfoxide
DMSO: Dimethylsulfoxide
DIPEA: Diisopropylethylamine
EDAC: 1-(3-Dimethylaminopropyl)-3-ethylcarbodiimide hydrochloride
EtOAc: Ethyl acetate
THF: Tetrahydrofuran
HOBT: 1-Hydroxy-benzotriazole
MeCN: Acetonitrile
NMP: N-Methylpyrrolidinone
TFA: Trifluoroacetic acid
min: Minutes
hrs: Hours General method A:

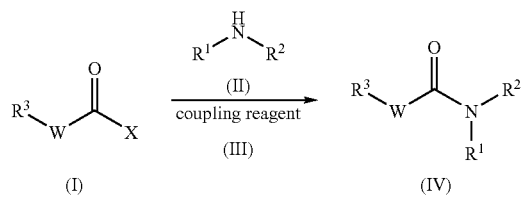

By allowing an acid (I) wherein X is OH and R$^3$ and W are defined as above to be coupled with an amine (II) wherein R$^1$ and R$^2$ are defined as above under standard amide forming conditions using a coupling reagent (III) (e.g. HOBT, EDAC and DIPEA in dry THF) affording amide (IV) wherein R$^1$, R$^2$, R$^3$, and W are defined as above; or by allowing a acid derivative (I) wherein X is halo, R$^3$—W—(C=O)O—, R$^{20}$—(C=O)O—, C$_1$-C$_6$alkyloxy or arylC$_1$-C$_6$-alkyloxy and R$^3$ and W are defined as above and R$^{20}$ is C$^1$-C$^6$alkyl, to be reacted with an amine (II) wherein R$^1$, R$^2$, R$^3$, and W are defined as above under basic conditions (e.g. triethylamine, K$_2$CO$_3$, NaH and the like) in a solvent (e.g. THF, DCM, DMF, NMP and the like) affording amide (IV); wherein R$^1$, R$^2$, R$^3$, and W are defined as above.

General method B:

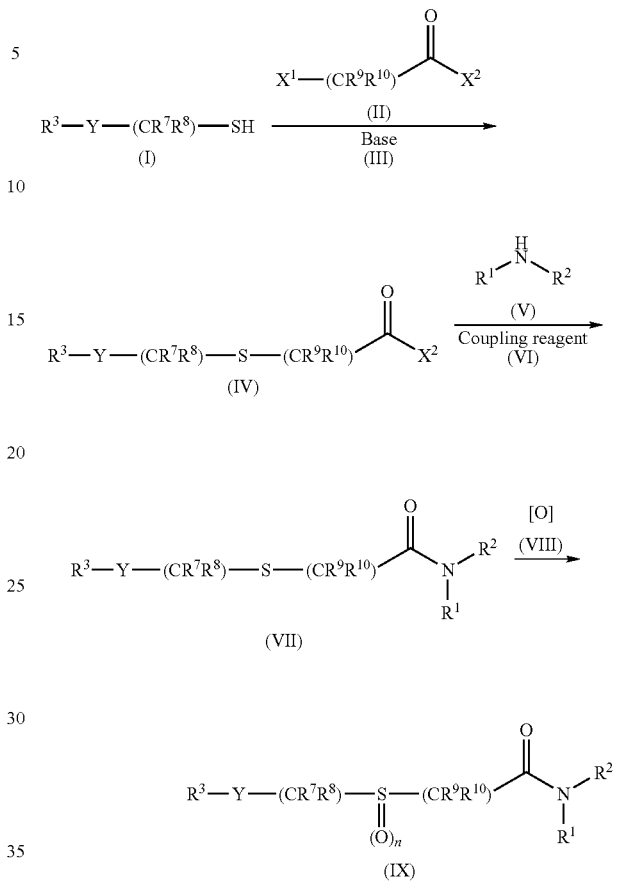

By allowing a mercaptane (I) wherein R$^3$, R$^7$, R$^8$ and Y are defined as above to be alkylated with an activated alkane (II) wherein R$^9$ and R$^{10}$ are defined as above and X$^1$ is halogene or OS(O)$_2$Me and X$^2$ is C$_1$-C$_6$alkyloxy or arylC$_1$-C$_6$alkyloxy under standard alkylation conditions using a base (III) (e.g. triethylamine, K$_2$CO$_3$, NaH and the like) in a solvent (e.g. THF, DCM, DMF, NMP and the like) affording a thioether (IV) wherein R$^3$, R$^7$, R$^8$, R$^9$, R$^{10}$, and Y are defined above and X$^2$ is C$_1$-C$_6$alkyloxy or arylC$_1$-C$_6$alkyloxy.

Activated acid (IV) wherein R$^3$, R$^7$, R$^8$, R$^9$, R$^{10}$, and Y are defined above and X$^2$ is OH is next coupled with an amine (V) wherein R$^1$ and R$^2$ are defined above under standard amide forming conditions using a coupling reagent (VI) (e.g. HOBT, EDAC and DIPEA in dry THF) affording amide (VII) wherein R$^1$, R$^2$, R$^3$, R$^7$, R$^8$, R$^9$, R$^{10}$ and Y are defined as above; or by allowing a acid derivative (IV) wherein X is halo, R$^{20}$—(C=O)O—, C$_1$-C$_6$alkyloxy or arylC$_1$-C$_6$alkyloxy and R$^3$, R$^7$, R$^8$, R$^9$, R$^{10}$ and Y are defined as above and R$^{20}$ is C$_1$-C$_6$-alkyl, to be reacted with an amine (V) wherein R$^1$ and R$^2$ are defined as above under basic conditions (e.g. triethylamine, K$_2$CO$_3$, NaH and the like) in a solvent (e.g. THF, DCM, DMF, NMP and the like) affording amide (VII); wherein R$^1$, R$^2$, R$^3$, R$^7$, R$^8$, R$^9$, and Y are defined as above.

Further thioether (VIII) wherein R$^1$, R$^2$, R$^3$, R$^7$, R$^8$, R$^9$, R$^{10}$ and Y are defined above is allowed to react with an oxidation reagent (e.g. H$_2$O$_2$ or CH$_3$C(=O)OOH or the like) in a solvent such as DCM or AcOH affording either sulfoxide (n=1) (IX) or sulphone (n=2) (IX) wherein R$^1$, R$^2$, R$^3$, R$^7$, R$^8$, R$^9$, R$^{10}$, Y, and n are defined above.

EXAMPLES

Example 1-1

General Procedure (A)

4-(2,4-Dichloro-phenoxy)-N-((1R,3S,5R,7S)-3-hydroxy-adamantan-1-yl)-butyramide

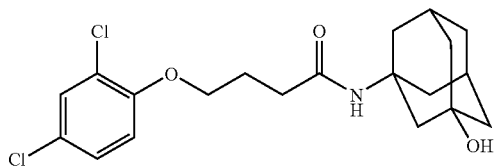 [SMILES: O=C(CCCOc1ccc(Cl)cc1Cl)NC12CC3CC(CC(O)(C3)C1)C2]

To a stirred solution of 4-(2,4-dichloro-phenoxy)-butyric acid (0.8 g, 3.21 mmol) in dry THF (25 mL) was added HOBt (0.48 mg, 3.533 mmol) and EDAC (0.68 g, 3.533 mmol). After stirring for 10 min. at room temperature, DIPEA (0.62 mL) and 3-amino-adamantan-1-ol (0.59 g, 3.533 mmol) were added and the resulting mixture was stirred for 16 hrs. at room temperature. The volatiles were removed in vacuo and to the residue was added water (25 mL) followed by extraction with EtOAc (3×35 mL). The combined organic phases were washed with brine, dried ($Na_2SO_4$), filtered and the solvent evaporated in vacuo. The oily residue was crystallised from diethyl ether (5 mL) affording after drying at 50° C. in vacuo 800 mg (62%) of the title compound as a solid.

$^1$H NMR (400 MHz, DMSO-$d_6$) δ 1.35-1.58 (m, 6H), 1.70-1.85 (m, 6H), 1.91 (q, 2H) 2.09 (br.s., 2H), 2.21 (t, 2H), 4.04 (t, 2H), 4.48 (br.s., 1H), 7.15 (d, 1H), 7.36 (dd, 1H), 7.40 (br.s., 1H), 7.57 (d, 1H).

In a similar way as described in example 1-1 the following compounds were made.

| Example No | Structure | Mw | IUPAC Name | LC/MS |
|---|---|---|---|---|
| 1-2 | 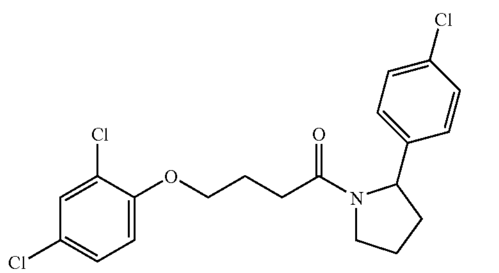 [SMILES: O=C(CCCOc1ccc(Cl)cc1Cl)N1CCCC1c1ccc(Cl)cc1] | 412.75 | 1-[2-(4-Chloro-phenyl)-pyrrolidin-1-yl]-4-(2,4-dichloro-phenoxy)-butan-1-one | 413 |
| 1-3 | 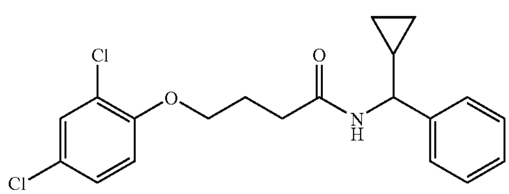 [SMILES: O=C(CCCOc1ccc(Cl)cc1Cl)NC(c1ccccc1)C1CC1] | 378.30 | N-(Cyclopropyl-phenyl-methyl)-4-(2,4-dichloro-phenoxy)-butyramide | 379 |
| 1-4 | 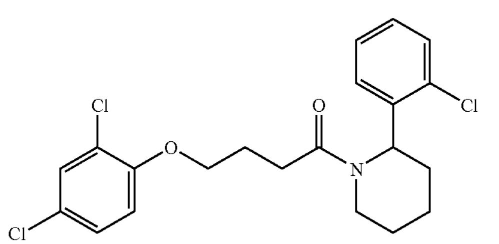 [SMILES: O=C(CCCOc1ccc(Cl)cc1Cl)N1CCCCC1c1ccccc1Cl] | 426.77 | 1-[2-(2-Chloro-phenyl)-piperidin-1-yl]-4-(2,4-dichloro-phenoxy)-butan-1-one | 427 |
| 1-5 | 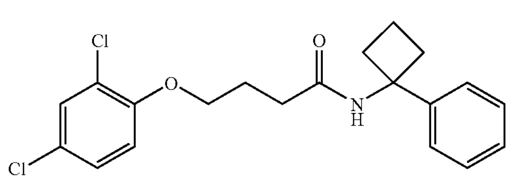 [SMILES: O=C(CCCOc1ccc(Cl)cc1Cl)NC1(c2ccccc2)CCC1] | 378.30 | 4-(2,4-Dichloro-phenoxy)-N-(1-phenyl-cyclobutyl)-butyramide | 379 |

-continued

| Example No | Structure | Mw | IUPAC Name | LC/MS |
|---|---|---|---|---|
| 1-6 | 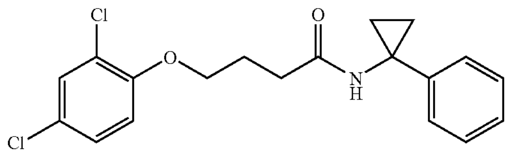 [SMILES: O=C(CCCOc1ccc(Cl)cc1Cl)NC1(c2ccccc2)CC1] | 364.28 | 4-(2,4-Dichloro-phenoxy)-N-(1-phenyl-cyclopropyl)-butyramide | 365 |
| 1-7 | 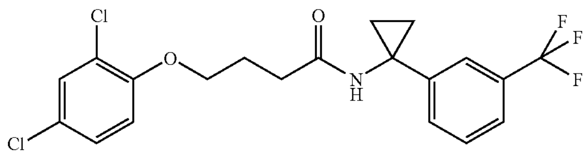 [SMILES: O=C(CCCOc1ccc(Cl)cc1Cl)NC1(c2cccc(C(F)(F)F)c2)CC1] | 432.27 | 4-(2,4-Dichloro-phenoxy)-N-[1-(3-trifluoromethyl-phenyl)-cyclopropyl]-butyramide | 433 |
| 1-8 | 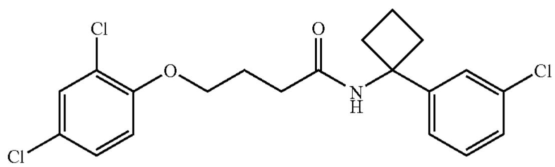 [SMILES: O=C(CCCOc1ccc(Cl)cc1Cl)NC1(c2cccc(Cl)c2)CCC1] | 412.75 | N-[1-(3-Chloro-phenyl)-cyclobutyl]-4-(2,4-dichloro-phenoxy)-butyramide | 413 |
| 1-9 | 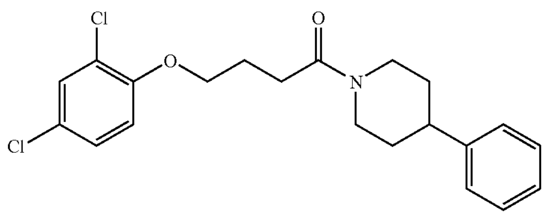 [SMILES: O=C(CCCOc1ccc(Cl)cc1Cl)N1CCC(c2ccccc2)CC1] | 392.33 | 4-(2,4-Dichloro-phenoxy)-1-(4-phenyl-piperidin-1-yl)-butan-1-one | 393 |
| 1-10 | 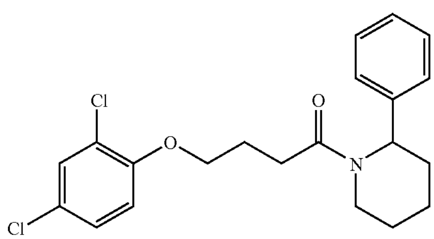 [SMILES: O=C(CCCOc1ccc(Cl)cc1Cl)N1CCCCC1c1ccccc1] | 392.33 | 4-(2,4-Dichloro-phenoxy)-1-(2-phenyl-piperidin-1-yl)-butan-1-one | 393 |
| 1-11 | 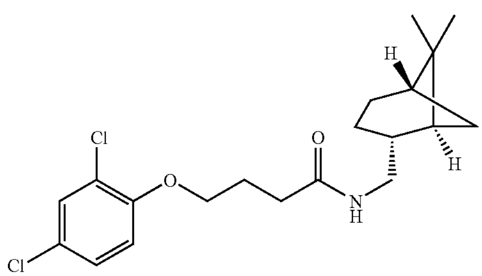 [SMILES: CC1(C)[C@H]2CC[C@@H](CNC(=O)CCCOc3ccc(Cl)cc3Cl)[C@@H]1C2] | 384.35 | 4-(2,4-Dichloro-phenoxy)-N-((1S,2R,5S)-6,6-dimethyl-bicyclo[3.1.1]-hept-2-ylmethyl)-butyramide | 385 |
| 1-12 | 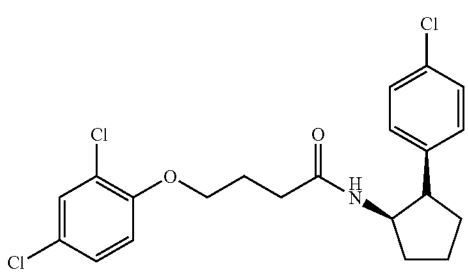 | 426.77 | N-[(1R,2R)-2-(4-Chloro-phenyl)-cyclopentyl]-4-(2,4-dichloro-phenoxy)-butyramide | 427 |

-continued

| Example No | Structure | Mw | IUPAC Name | LC/MS |
|---|---|---|---|---|
| 1-13 | 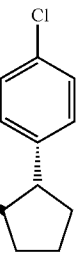 | 426.77 | N-[(1R,2S)-2-(4-Chloro-phenyl)-cyclopentyl]-4-(2,4-dichloro-phenoxy)-butyramide | 427 |
| 1-14 | 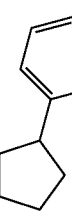 | 392.33 | 4-(2,4-Dichloro-phenoxy)-N-(2-phenyl-cyclopentyl)-butyramide | 393 |
| 1-15 | 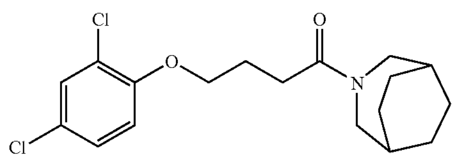 [SMILES: O=C(CCCOc1ccc(Cl)cc1Cl)N1CC2CCC(CC2)C1] | 356.30 | 1-(3-Aza-bicyclo[3.2.2]-non-3-yl)-4-(2,4-di-chloro-phenoxy)-butan-1-one | 357 |
| 1-16 | 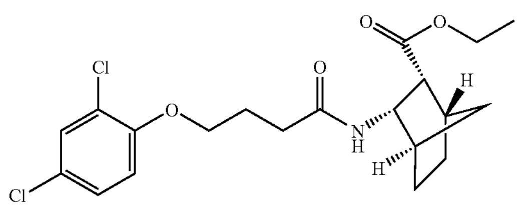 [SMILES: CCOC(=O)[C@@H]1[C@H]2CC[C@H](C2)[C@@H]1NC(=O)CCCOc1ccc(Cl)cc1Cl] | 414.33 | (1S,2R,3S,4R)-3-[4-(2,4-Dichloro-phenoxy)-butyrylamino]-bicyclo-[2.2.1]heptane-2-carboxylic acid ethyl ester | 415 |
| 1-17 | 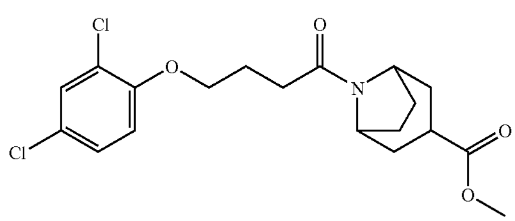 [SMILES: COC(=O)C1CC2CCC(C1)N2C(=O)CCCOc1ccc(Cl)cc1Cl] | 400.31 | 8-[4-(2,4-Dichloro-phenoxy)-butyryl]-8-aza-bicyclo[3.2.1]octane-3-carboxylic acid methyl ester | 401 |
| 1-18 | 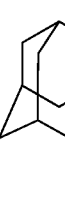 | 438.40 | N-Cyclopropyl-4-(2,4-dichloro-phenoxy)-N-(5-hydroxy-adamantan-2-yl)-butyramide | 439 |
| 1-19 | 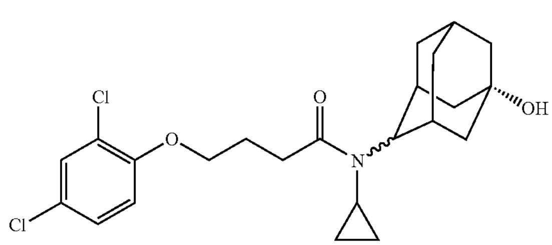 | 438.40 | N-Cyclopropyl-4-(2,4-dichloro-phenoxy)-N-(5-hydroxy-adamantan-2-yl)-butyramide | 439 |

-continued

| Example No | Structure | Mw | IUPAC Name | LC/MS |
|---|---|---|---|---|
| 1-20 | 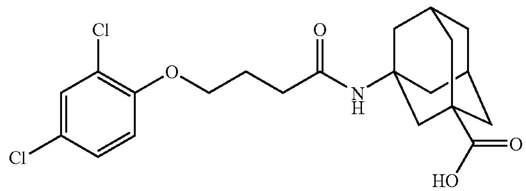 [SMILES: O=C(CCCOc1ccc(Cl)cc1Cl)NC12CC3CC(C1)CC(C(=O)O)(C3)C2] | 426.34 | 3-[4-(2,4-Dichloro-phenoxy)-butyrylamino]-adamantane-1-carboxylic acid | 427 |
| 1-21 | 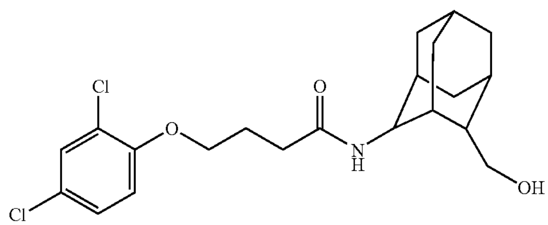 [SMILES: O=C(CCCOc1ccc(Cl)cc1Cl)NC1C2CC3CC(C2)C(CO)C1C3] | 412.36 | 4-(2,4-Dichloro-phenoxy)-N-(4-hydroxy-methyl-adamantan-2-yl)-butyramide | 413 |
| 1-22 | 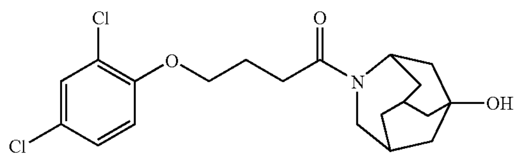 [SMILES: O=C(CCCOc1ccc(Cl)cc1Cl)N1CC2CC3CC1CC(O)(C3)C2] | 398.33 | 4-(2,4-Dichloro-phenoxy)-1-(1-hydroxy-4-aza-tricyclo-[4.3.1.1{3,8}]undec-4-yl)-butan-1-one | 399 |
| 1-23 | 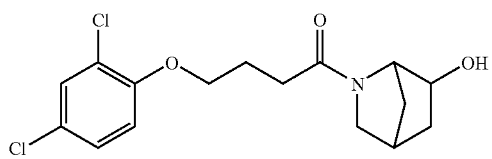 [SMILES: O=C(CCCOc1ccc(Cl)cc1Cl)N1CC2CC(O)C1C2] | 343.07 | 4-(2,4-Dichloro-phenoxy)-1-(6-hydroxy-2-aza-bicyclo[2.2.1]hept-2-yl)-butan-1-one | 344 |
| 1-24 | 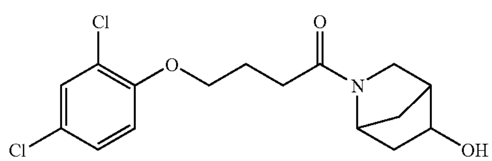 [SMILES: O=C(CCCOc1ccc(Cl)cc1Cl)N1CC2CC1CC2O] | 343.07 | 4-(2,4-Dichloro-phenoxy)-1-(5-hydroxy-2-aza-bicyclo[2.2.1]hept-2-yl)-butan-1-one | 344 |
| 1-25 | 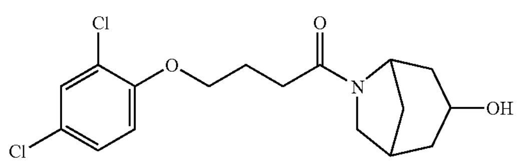 [SMILES: O=C(CCCOc1ccc(Cl)cc1Cl)N1CC2CC(O)CC1C2] | 357.09 | 4-(2,4-Dichloro-phenoxy)-1-(3-hydroxy-6-aza-bicyclo[3.2.1]oct-6-yl)-butan-1-one | 358 |
| 1-26 | 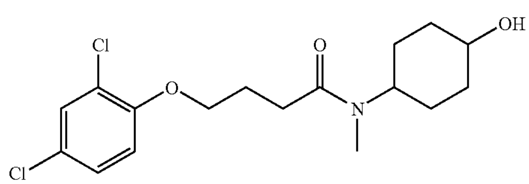 [SMILES: CN(C(=O)CCCOc1ccc(Cl)cc1Cl)C1CCC(O)CC1] | 359.11 | 4-(2,4-Dichloro-phenoxy)-N-(4-hydroxy-cyclohexyl)-N-methyl-butyramide | 360 |
| 1-27 | 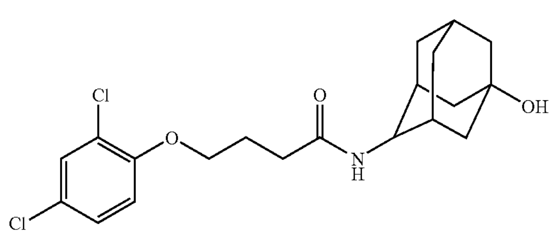 [SMILES: O=C(CCCOc1ccc(Cl)cc1Cl)NC1C2CC3CC1CC(O)(C3)C2] | 397.12 | 4-(2,4-Dichloro-phenoxy)-N-(5-hydroxy-adamantan-2-yl)-butyramide | 398 |

-continued

| Example No | Structure | Mw | IUPAC Name | LC/MS |
|---|---|---|---|---|
| 1-28 | 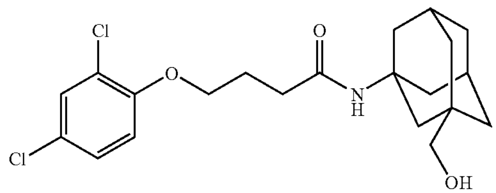 [SMILES: O=C(CCCOc1ccc(Cl)cc1Cl)NC12CC3CC(CC(CO)(C3)C1)C2] | 411.14 | 4-(2,4-Dichloro-phenoxy)-N-(3-hydroxy-methyl-adamantan-1-yl)-butyramide | 412 |
| 1-29 | 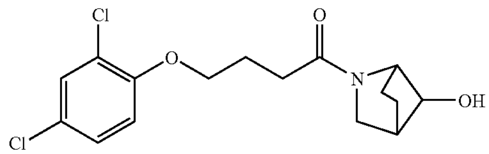 [SMILES: O=C(CCCOc1ccc(Cl)cc1Cl)N1CC2CCC1C2O] | 343.07 | 4-(2,4-Dichloro-phenoxy)-1-(7-hydroxy-2-aza-bicyclo[2.2.1]hept-2-yl)-butan-1-one | 344 |
| 1-30 | 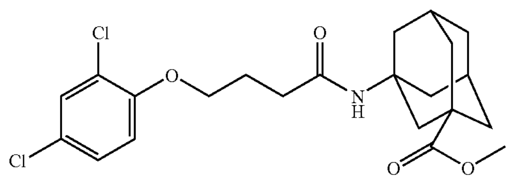 [SMILES: COC(=O)C12CC3CC(CC(NC(=O)CCCOc4ccc(Cl)cc4Cl)(C3)C1)C2] | 439.13 | 3-[4-(2,4-Dichloro-phenoxy)-butyrylamino]-adamantane-1-carboxylic acid methyl ester | 450 |
| 1-31 | 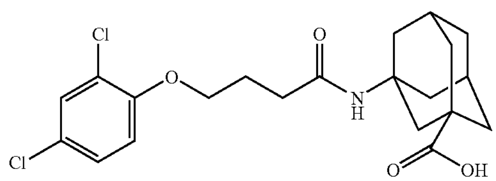 [SMILES: O=C(CCCOc1ccc(Cl)cc1Cl)NC12CC3CC(C1)CC(C(=O)O)(C3)C2] | 425.12 | 3-[4-(2,4-Dichloro-phenoxy)-butyrylamino]-adamantane-1-carboxylic acid | 426 |
| 1-32 | 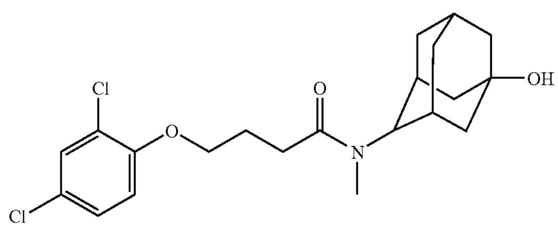 [SMILES: CN(C(=O)CCCOc1ccc(Cl)cc1Cl)C1C2CC3CC1CC(O)(C3)C2] | 411.14 | 4-(2,4-Dichloro-phenoxy)-N-(5-hydroxy-adamantan-2-yl)-N-methyl-butyramide | 412 |
| 1-33 | 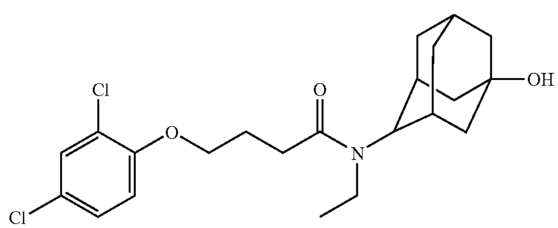 [SMILES: CCN(C(=O)CCCOc1ccc(Cl)cc1Cl)C1C2CC3CC1CC(O)(C3)C2] | 425.15 | 4-(2,4-Dichloro-phenoxy)-N-ethyl-N-(5-hydroxy-adamantan-2-yl)-butyramide | 426 |
| 1-34 | 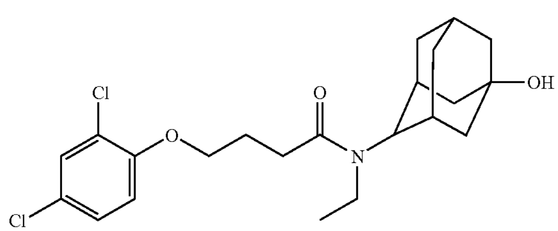 [SMILES: CCN(C(=O)CCCOc1ccc(Cl)cc1Cl)C1C2CC3CC1CC(O)(C3)C2] | 425.15 | 4-(2,4-Dichloro-phenoxy)-N-ethyl-N-(5-hydroxy-adamantan-2-yl)-butyramide | 426 |
| 1-35 | 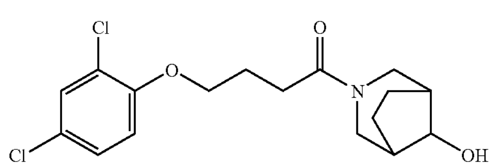 [SMILES: O=C(CCCOc1ccc(Cl)cc1Cl)N1CC2CCC(C1)C2O] | 357.09 | 4-(2,4-Dichloro-phenoxy)-1-(8-hydroxy-3-aza-bicyclo[3.2.1]oct-3-yl)-butan-1-one | 358 |

-continued

| Example No | Structure | Mw | IUPAC Name | LC/MS |
|---|---|---|---|---|
| 1-36 | 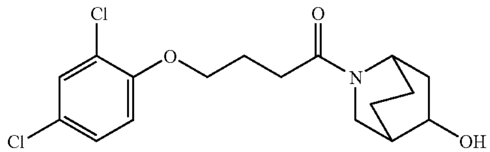 [SMILES: O=C(CCCOc1ccc(Cl)cc1Cl)N1CC2CCC1CC2O] | 357.09 | 4-(2,4-Dichloro-phenoxy)-1-(5-hydroxy-2-aza-bicyclo[2.2.2]oct-2-yl)-butan-1-one | 358 |
| 1-37 | 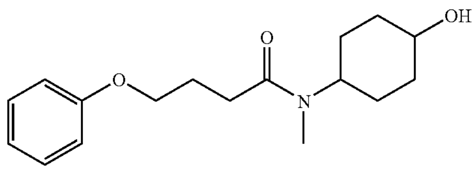 [SMILES: CN(C(=O)CCCOc1ccccc1)C1CCC(O)CC1] | 291.18 | N-(4-Hydroxy-cyclohexyl)-N-methyl-4-phenoxy-butyramide | 292 |
| 1-38 | 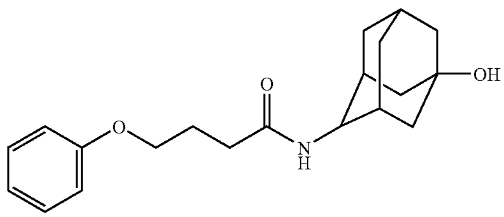 [SMILES: O=C(CCCOc1ccccc1)NC1C2CC3CC1CC(O)(C3)C2] | 329.20 | N-(5-Hydroxy-adamantan-2-yl)-4-phenoxy-butyramide | 330 |
| 1-39 | 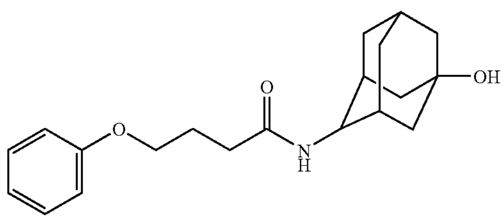 [SMILES: O=C(CCCOc1ccccc1)NC1C2CC3CC1CC(O)(C3)C2] | 329.20 | N-(5-Hydroxy-adamantan-2-yl)-4-phenoxy-butyramide | 339 |
| 1-40 | 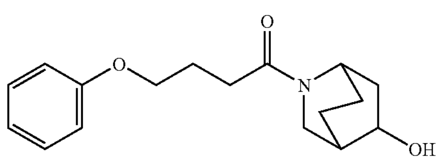 [SMILES: O=C(CCCOc1ccccc1)N1CC2CCC1CC2O] | 289.17 | 1-(5-Hydroxy-2-aza-bicyclo[2.2.2]oct-2-yl)-4-phenoxy-butan-1-one | 290 |
| 1-41 | 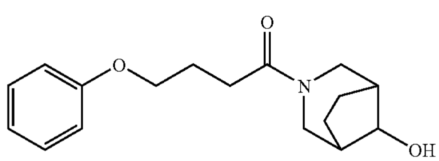 [SMILES: O=C(CCCOc1ccccc1)N1CC2CCC(C1)C2O] | 289.17 | 1-(8-Hydroxy-3-aza-bicyclo[3.2.1]oct-3-yl)-4-phenoxy-butan-1-one | 290 |
| 1-42 | 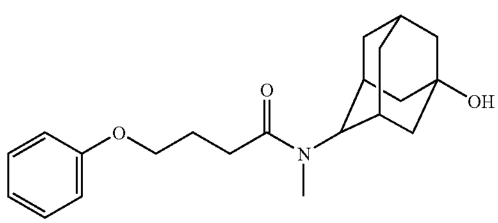 [SMILES: CN(C(=O)CCCOc1ccccc1)C1C2CC3CC1CC(O)(C3)C2] | 343.21 | N-(5-Hydroxy-adamantan-2-yl)-N-methyl-4-phenoxy-butyramide | 344 |
| 1-43 | 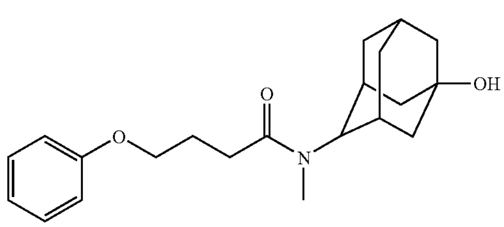 [SMILES: CN(C(=O)CCCOc1ccccc1)C1C2CC3CC1CC(O)(C3)C2] | 343.21 | N-(5-Hydroxy-adamantan-2-yl)-N-methyl-4-phenoxy-butyramide | 344 |

-continued

| Example No | Structure | Mw | IUPAC Name | LC/MS |
|---|---|---|---|---|
| 1-44 | 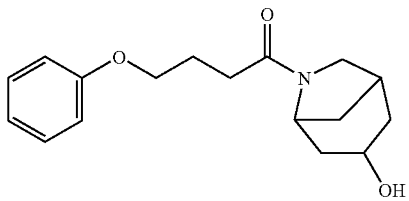 [SMILES: O=C(CCCOc1ccccc1)N1CC2CC(O)CC1C2] | 289.17 | 1-(3-Hydroxy-6-aza-bicyclo[3.2.1]oct-6-yl)-4-phenoxy-butan-1-one | 290 |
| 1-45 | 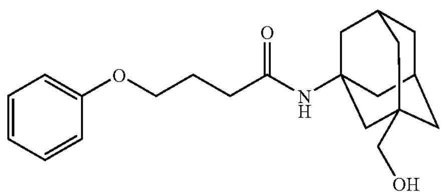 [SMILES: O=C(CCCOc1ccccc1)NC12CC3CC(CC(CO)(C3)C1)C2] | 343.21 | N-(3-Hydroxymethyl-adamantan-1-yl)-4-phenoxy-butyramide | 344 |
| 1-46 | 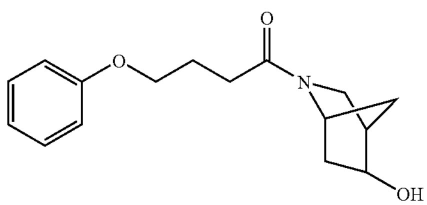 [SMILES: O=C(CCCOc1ccccc1)N1CC2CC1CC2O] | 275.15 | 1-(5-Hydroxy-2-aza-bicyclo[2.2.1]hept-2-yl)-4-phenoxy-butan-1-one | 276 |
| 1-47 | 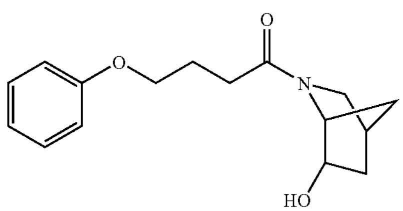 [SMILES: O=C(CCCOc1ccccc1)N1CC2CC(O)C1C2] | 275.15 | 1-(6-Hydroxy-2-aza-bicyclo[2.2.1]hept-2-yl)-4-phenoxy-butan-1-one | 276 |
| 1-48 | 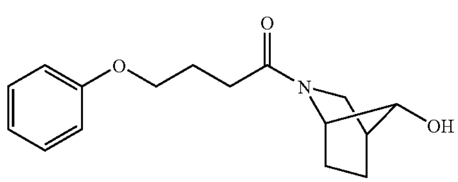 [SMILES: O=C(CCCOc1ccccc1)N1CC2CCC1C2O] | 275.15 | 1-(7-Hydroxy-2-aza-bicyclo[2.2.1]hept-2-yl)-4-phenoxy-butan-1-one | 276 |
| 1-49 | 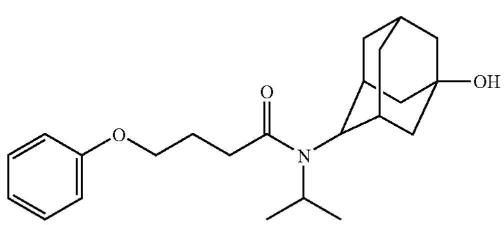 [SMILES: CC(C)N(C(=O)CCCOc1ccccc1)C1C2CC3CC1CC(O)(C3)C2] | 371.51 | N-(5-Hydroxy-adamantan-2-yl)-N-isopropyl-4-phenoxy-butyramide | 372 |
| 1-50 | 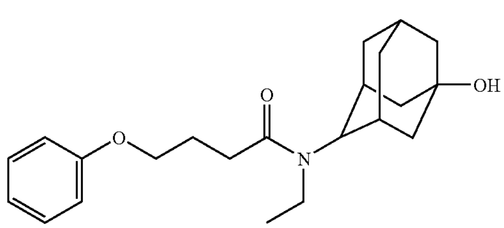 [SMILES: CCN(C(=O)CCCOc1ccccc1)C1C2CC3CC1CC(O)(C3)C2] | 357.49 | N-Ethyl-N-(5-hydroxy-adamantan-2-yl)-4-phenoxy-butyramide | 358 |

-continued

| Example No | Structure | Mw | IUPAC Name | LC/MS |
|---|---|---|---|---|
| 1-51 | 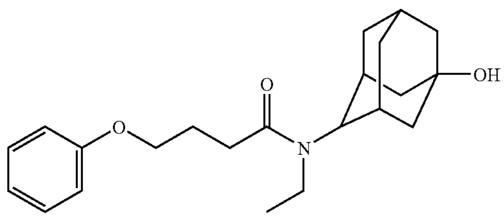 [SMILES: CCN(C(=O)CCCOc1ccccc1)C1C2CC3CC1CC(O)(C3)C2] | 357.49 | N-Ethyl-N-(5-hydroxy-adamantan-2-yl)-4-phenoxy-butyramide | 358 |
| 1-52 | 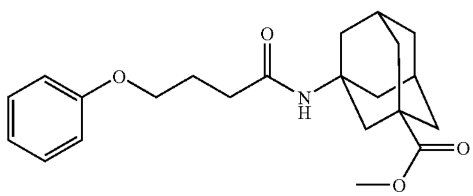 [SMILES: COC(=O)C12CC3CC(CC(NC(=O)CCCOc4ccccc4)(C3)C1)C2] | 371.47 | 3-(4-Phenoxy-butyryl-amino)-adamantane-1-carboxylic acid methyl ester | 372 |
| 1-53 | 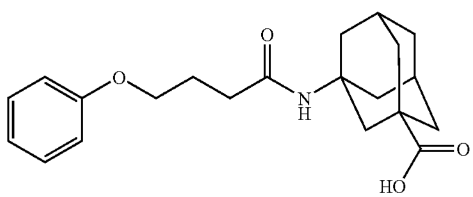 [SMILES: O=C(CCCOc1ccccc1)NC12CC3CC(C1)CC(C(=O)O)(C3)C2] | 357.44 | 3-(4-Phenoxy-butyryl-amino)-adamantane-1-carboxylic acid | 358 |
| 1-54 | 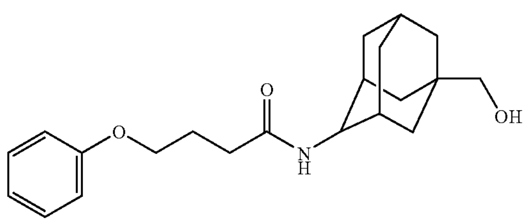 [SMILES: O=C(CCCOc1ccccc1)NC1C2CC3CC1CC(CO)(C3)C2] | 343.46 | N-(5-Hydroxymethyl-adamantan-2-yl)-4-phenoxy-butyramide | 344 |
| 1-55 | 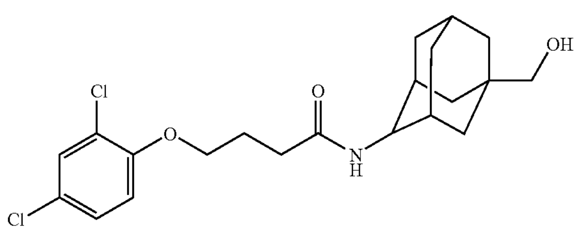 [SMILES: O=C(CCCOc1ccc(Cl)cc1Cl)NC1C2CC3CC1CC(CO)(C3)C2] | 412.35 | 4-(2,4-Dichloro-phenoxy)-N-(5-hydroxy-methyl-adamantan-2-yl)-butyramide | 413 |
| 1-56 | 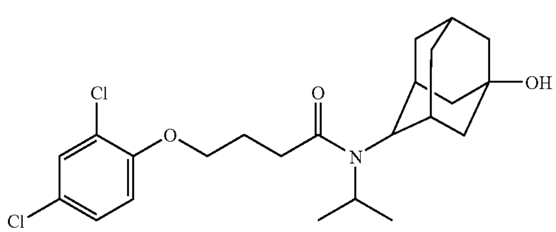 [SMILES: CC(C)N(C(=O)CCCOc1ccc(Cl)cc1Cl)C1C2CC3CC1CC(O)(C3)C2] | 440.4 | 4-(2,4-Dichloro-phenoxy)-N-(5-hydroxy-adamantan-2-yl)-N-isopropyl-butyramide | 441 |
| 1-57 | 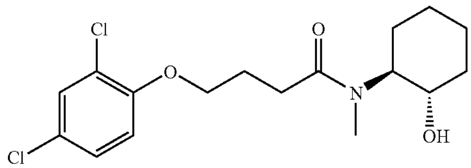 [SMILES: CN(C(=O)CCCOc1ccc(Cl)cc1Cl)[C@H]1CCCC[C@@H]1O] | 359.11 | 4-(2,4-Dichloro-phenoxy)-N-((1S,2S)-2-hydroxy-cyclohexyl)-N-methyl-butyramide | 360 |

-continued

| Example No | Structure | Mw | IUPAC Name | LC/MS |
|---|---|---|---|---|
| 1-58 | 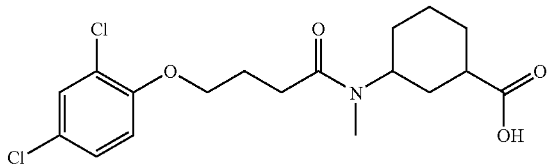 [SMILES: CN(C(=O)CCCOc1ccc(Cl)cc1Cl)C1CCCC(C(=O)O)C1] | 387.10 | 3-{[4-(2,4-Dichloro-phenoxy)-butyryl]-methyl-amino}-cyclo-hexanecarboxylic acid | 388 |
| 1-59 | 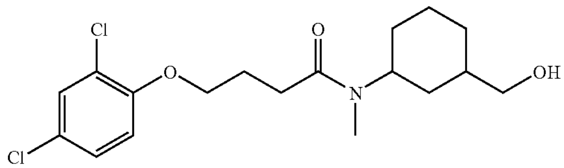 [SMILES: CN(C(=O)CCCOc1ccc(Cl)cc1Cl)C1CCCC(CO)C1] | 373.12 | 4-(2,4-Dichloro-phenoxy)-N-(3-hydroxy-methyl-cyclo-hexyl)-N-methyl-butyramide | 374 |
| 1-60 | 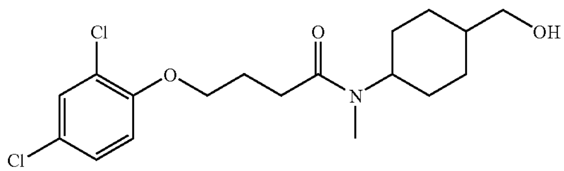 [SMILES: CN(C(=O)CCCOc1ccc(Cl)cc1Cl)C1CCC(CO)CC1] | 373.12 | 4-(2,4-Dichloro-phenoxy)-N-(4-hydroxy-methyl-cyclohexyl)-N-methyl-butyramide | 374 |
| 1-61 | 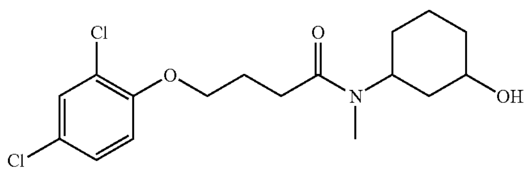 [SMILES: CN(C(=O)CCCOc1ccc(Cl)cc1Cl)C1CCCC(O)C1] | 359.11 | 4-(2,4-Dichloro-phenoxy)-N-(3-hydroxy-cyclohexyl)-N-methyl-butyramide | 360 |
| 1-62 | 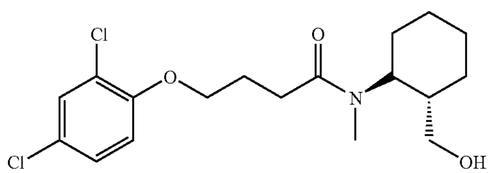 | 373.12 | 4-(2,4-Dichloro-phenoxy)-N-((S)-2-hydroxymethyl-cyclo-hexyl)-N-methyl-butyramide | 374 |
| 1-63 | 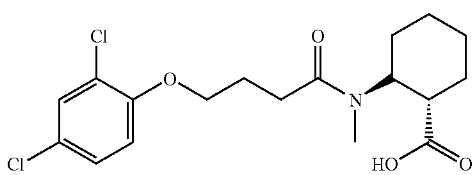 | 387.10 | (S)-2-{(R)-[4-(2,4-Dichloro-phenoxy)-butyryl]-methyl-amino}-cyclohexanecarboxylic acid | 388 |
| 1-64 | 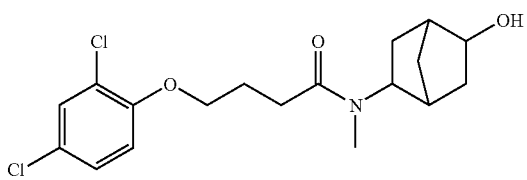 [SMILES: CN(C(=O)CCCOc1ccc(Cl)cc1Cl)C1CC2CC1CC2O] | 371.11 | 4-(2,4-Dichloro-phenoxy)-N-(5-hydroxy-bicyclo[2.2.1]hept-2-yl)-N-methyl-butyramide | 372 |
| 1-65 | 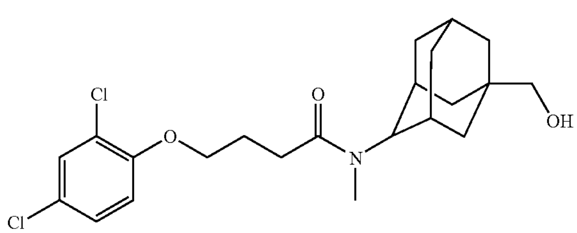 [SMILES: CN(C(=O)CCCOc1ccc(Cl)cc1Cl)C1C2CC3CC1CC(CO)(C3)C2] | 425.15 | 4-(2,4-Dichloro-phenoxy)-N-(5-hydroxy-methyl-adamantan-2-yl)-N-methyl-butyramide | 426 |

-continued

| Example No | Structure | Mw | IUPAC Name | LC/MS |
|---|---|---|---|---|
| 1-66 | 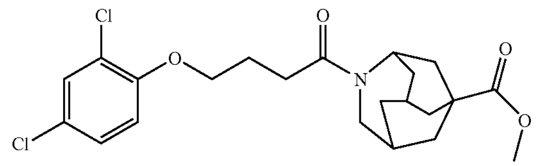 [SMILES: COC(=O)C12CC3CC(CN(C(=O)CCCOc4ccc(Cl)cc4Cl)C(C3)C1)C2] | 439.13 | 4-[4-(2,4-Dichloro-phenoxy)-butyryl]-4-aza-tricyclo[4.3.1.1{3,8}]-undecane-1-carboxylic acid methyl ester | 440 |
| 1-67 | 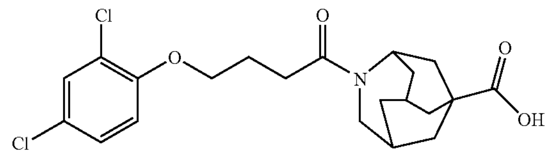 [SMILES: O=C(CCCOc1ccc(Cl)cc1Cl)N1CC2CC3CC1CC(C(=O)O)(C3)C2] | 425.12 | 4-[4-(2,4-Dichloro-phenoxy)-butyryl]-4-aza-tricyclo[4.3.1.1{3,8}]-undecane-1-carboxylic acid | 426 |
| 1-68 | 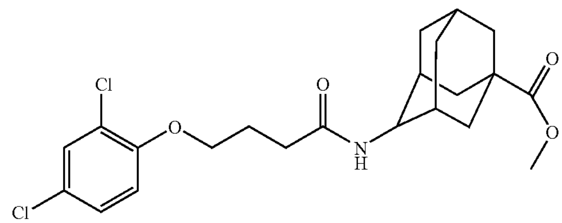 [SMILES: COC(=O)C12CC3CC(C1)C(NC(=O)CCCOc1ccc(Cl)cc1Cl)C(C3)C2] | 439.13 | 4-[4-(2,4-Dichloro-phenoxy)-butyrylamino]-adamantane-1-carboxylic acid methyl ester | 440 |
| 1-69 | 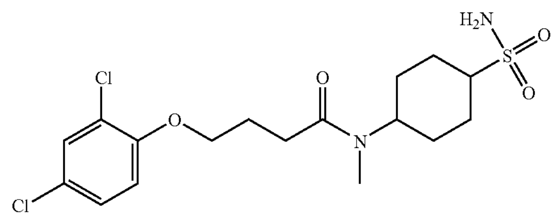 [SMILES: CN(C(=O)CCCOc1ccc(Cl)cc1Cl)C1CCC(S(N)(=O)=O)CC1] | 422.08 | 4-(2,4-Dichloro-phenoxy)-N-methyl-N-(4-sulfamoyl-cyclohexyl)-butyramide | 423 |
| 1-70 | 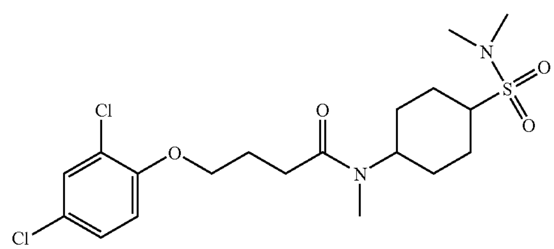 [SMILES: CN(C(=O)CCCOc1ccc(Cl)cc1Cl)C1CCC(S(=O)(=O)N(C)C)CC1] | 450.11 | 4-(2,4-Dichloro-phenoxy)-N-(4-dimethyl-sulfamoyl-cyclohexyl)-N-methyl-butyramide | 451 |
| 1-71 | 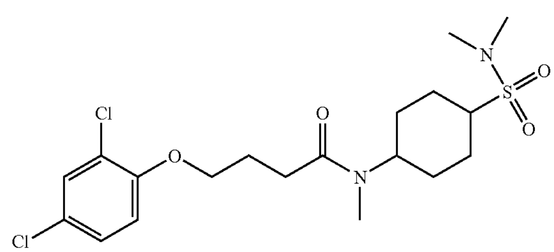 [SMILES: CN(C(=O)CCCOc1ccc(Cl)cc1Cl)C1CCC(S(=O)(=O)N(C)C)CC1] | 450.11 | 4-(2,4-Dichloro-phenoxy)-N-(4-dimethyl-sulfamoyl-cyclohexyl)-N-methyl-butyramide | 451 |
| 1-72 | 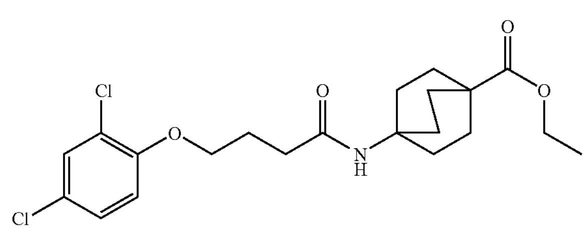 [SMILES: CCOC(=O)C12CCC(NC(=O)CCCOc3ccc(Cl)cc3Cl)(CC1)CC2] | 427.13 | 4-[4-(2,4-Dichloro-phenoxy)-butyrylamino]-bicyclo[2.2.2]octane-1-carboxylic acid ethyl ester | 428 |

-continued

| Example No | Structure | Mw | IUPAC Name | LC/MS |
|---|---|---|---|---|
| 1-73 | 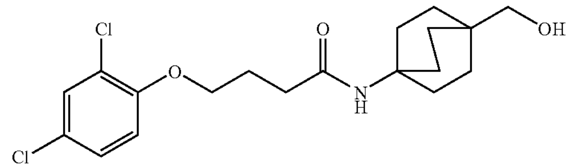 [SMILES: O=C(CCCOc1ccc(Cl)cc1Cl)NC12CCC(CO)(CC1)CC2] | 385.12 | 4-(2,4-Dichloro-phenoxy)-N-(4-hydroxy-methyl-bicyclo[2.2.2]oct-1-yl)-butyramide | 386 |
| 1-74 | 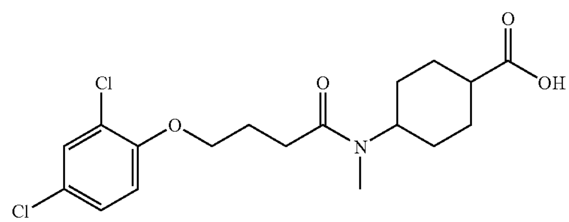 [SMILES: CN(C(=O)CCCOc1ccc(Cl)cc1Cl)C1CCC(C(=O)O)CC1] | 387.1 | 4-{[4-(2,4-Dichloro-phenoxy)-butyryl]-methyl-amino}-cyclo-hexanecarboxylic acid | 388 |
| 1-75 | 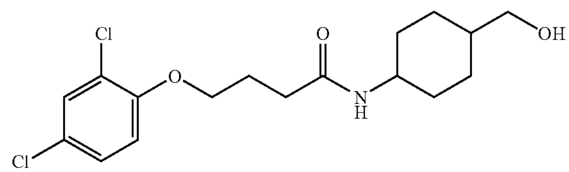 [SMILES: O=C(CCCOc1ccc(Cl)cc1Cl)NC1CCC(CO)CC1] | 359.11 | 4-(2,4-Dichloro-phenoxy)-N-(4-hydroxy-methyl-cyclohexyl)-butyramide | 360 |
| 1-76 | 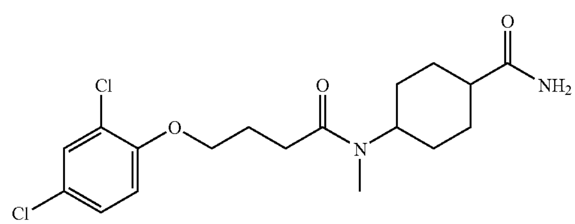 [SMILES: CN(C(=O)CCCOc1ccc(Cl)cc1Cl)C1CCC(C(N)=O)CC1] | 386.12 | 4-{[4-(2,4-Dichloro-phenoxy)-butyryl]-methyl-amino}-cyclo-hexanecarboxylic acid amide | 387 |
| 1-77 | 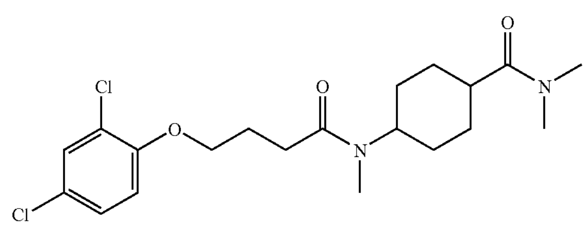 [SMILES: CN(C)C(=O)C1CCC(N(C)C(=O)CCCOc2ccc(Cl)cc2Cl)CC1] | 414.15 | 4-{[4-(2,4-Dichloro-phenoxy)-butyryl]-methyl-amino}-cyclo-hexanecarboxylic acid dimethylamide | 415 |
| 1-78 | 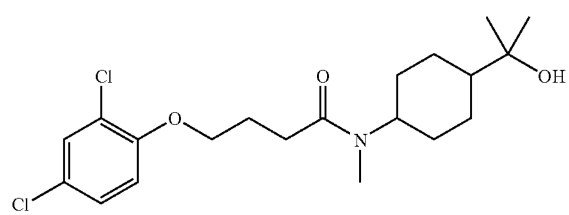 [SMILES: CN(C(=O)CCCOc1ccc(Cl)cc1Cl)C1CCC(C(C)(C)O)CC1] | 401.15 | 4-(2,4-Dichloro-phenoxy)-N-[4-(1-hydroxy-1-methyl-ethyl)-cyclohexyl]-N-methyl-butyramide | 402 |
| 1-79 | 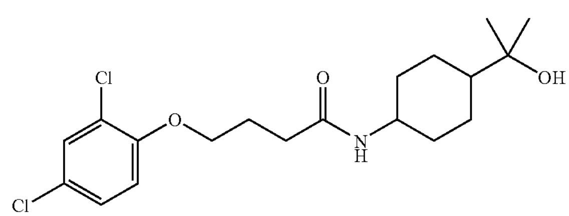 [SMILES: CC(C)(O)C1CCC(NC(=O)CCCOc2ccc(Cl)cc2Cl)CC1] | 387.14 | 4-(2,4-Dichloro-phenoxy)-N-[4-(1-hydroxy-1-methyl-ethyl)-cyclohexyl]-butyramide | 388 |

-continued

| Example No | Structure | Mw | IUPAC Name | LC/MS |
|---|---|---|---|---|
| 1-80 | 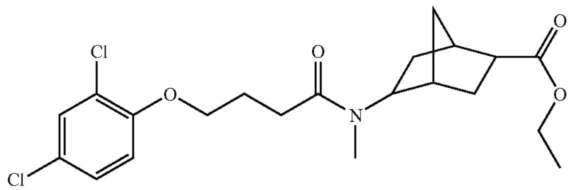 [SMILES: CCOC(=O)C1CC2CC1CC2N(C)C(=O)CCCOc1ccc(Cl)cc1Cl] | 427.13 | 5-{[4-(2,4-Dichloro-phenoxy)-butyryl]-methyl-amino}-bicyclo[2.2.1]heptane-2-carboxylic acid ethyl ester | 428 |
| 1-81 | 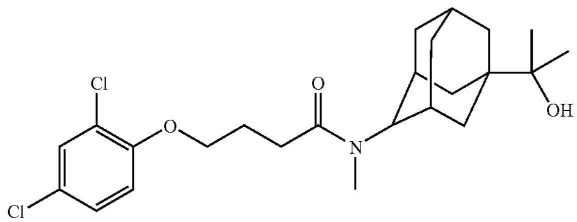 [SMILES: CN(C(=O)CCCOc1ccc(Cl)cc1Cl)C1C2CC3CC1CC(C(C)(C)O)(C3)C2] | 453.18 | 4-(2,4-Dichloro-phenoxy)-N-[5-(1-hydroxy-1-methyl-ethyl)-adamantan-2-yl]-N-methyl-butyramide | 454 |
| 1-82 | 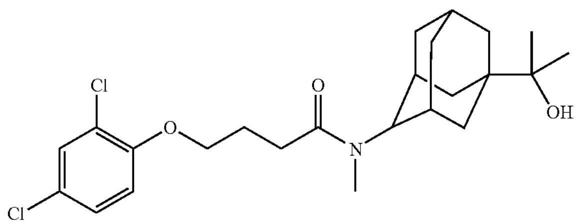 [SMILES: CN(C(=O)CCCOc1ccc(Cl)cc1Cl)C1C2CC3CC1CC(C(C)(C)O)(C3)C2] | 453.18 | 4-(2,4-Dichloro-phenoxy)-N-[5-(1-hydroxy-1-methyl-ethyl)-adamantan-2-yl]-N-methyl-butyramide | 454 |
| 1-83 | 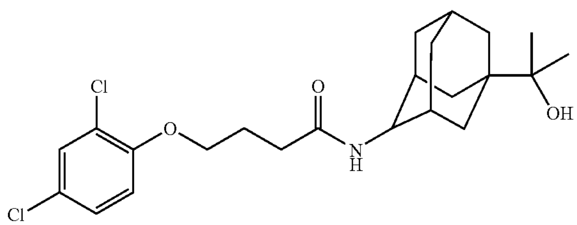 | 439.17 | 4-(2,4-Dichloro-phenoxy)-N-[5-(1-hydroxy-1-methyl-ethyl)-adamantan-2-yl]-butyramide | 440 |
| 1-84 | 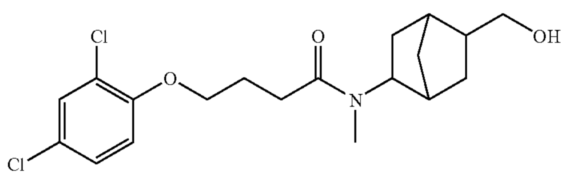 [SMILES: CN(C(=O)CCCOc1ccc(Cl)cc1Cl)C1CC2CC1CC2CO] | 385.12 | 4-(2,4-Dichloro-phenoxy)-N-(5-hydroxy-methyl-adamantan-2-yl)-N-methyl-butyramide | 386 |
| 1-85 | 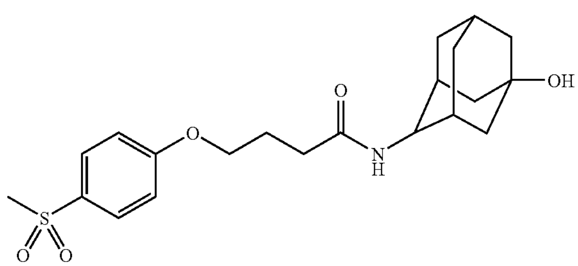 [SMILES: CS(=O)(=O)c1ccc(OCCCC(=O)NC2C3CC4CC2CC(O)(C4)C3)cc1] | 407.18 | N-(5-Hydroxy-adamantan-2-yl)-4-(4-methanesulfonyl-phenoxy)-butyramide | 408 |
| 1-86 | 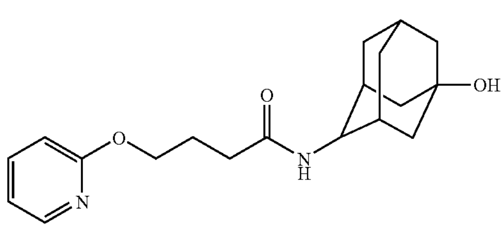 [SMILES: O=C(CCCOc1ccccn1)NC1C2CC3CC1CC(O)(C3)C2] | 330.19 | N-(5-Hydroxy-adamantan-2-yl)-4-(pyridin-2-yloxy)-butyramide | 331 |

-continued

| Example No | Structure | Mw | IUPAC Name | LC/MS |
|---|---|---|---|---|
| 1-87 | 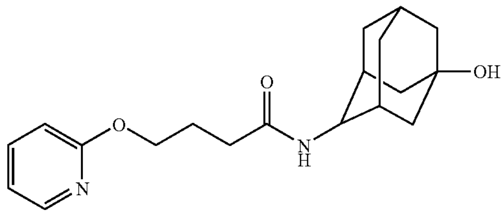 [SMILES: O=C(CCCOc1ccccn1)NC1C2CC3CC1CC(O)(C3)C2] | 330.19 | N-(5-Hydroxy-adamantan-2-yl)-4-(pyridin-2-yloxy)-butyramide | 331 |
| 1-88 | 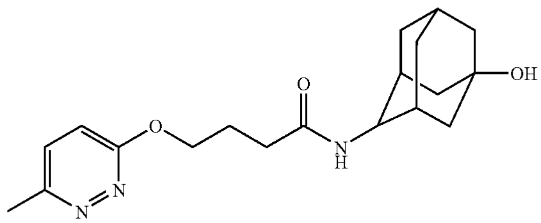 [SMILES: Cc1ccc(OCCCC(=O)NC2C3CC4CC2CC(O)(C4)C3)nn1] | 345.21 | N-(5-Hydroxy-adamantan-2-yl)-4-(6-methyl-pyridazin-3-yloxy)-butyramide | 346 |
| 1-89 | 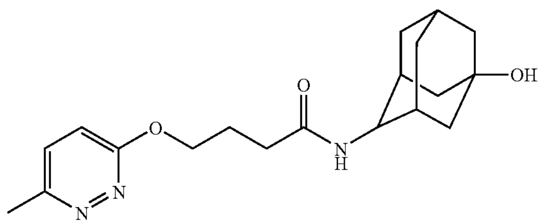 [SMILES: Cc1ccc(OCCCC(=O)NC2C3CC4CC2CC(O)(C4)C3)nn1] | 345.21 | N-(5-Hydroxy-adamantan-2-yl)-4-(6-methyl-pyridazin-3-yloxy)-butyramide | 346 |
| 1-90 | 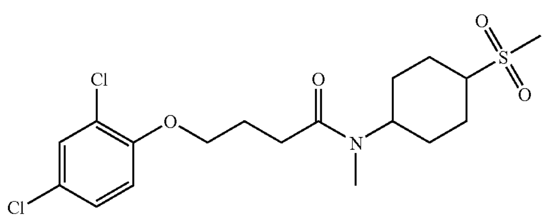 [SMILES: CN(C(=O)CCCOc1ccc(Cl)cc1Cl)C1CCC(S(C)(=O)=O)CC1] | 421.09 | 4-(2,4-Dichloro-phenoxy)-N-(4-methane-sulfonyl-cyclohexyl)-N-methyl-butyramide | 422 |
| 1-91 | 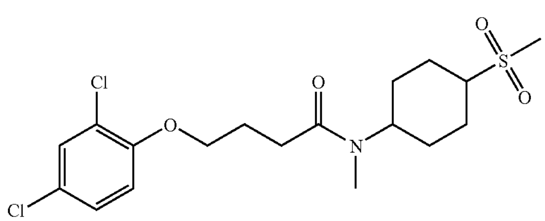 [SMILES: CN(C(=O)CCCOc1ccc(Cl)cc1Cl)C1CCC(S(C)(=O)=O)CC1] | 421.09 | 4-(2,4-Dichloro-phenoxy)-N-(4-methane-sulfonyl-cyclohexyl)-N-methyl-butyramide | 422 |
| 1-92 | 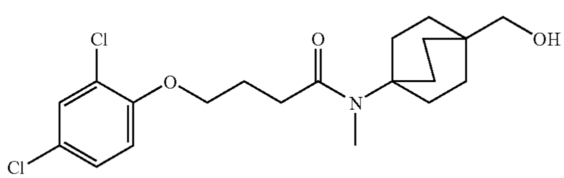 [SMILES: CN(C(=O)CCCOc1ccc(Cl)cc1Cl)C12CCC(CO)(CC1)CC2] | 399.14 | 4-(2,4-Dichloro-phenoxy)-N-(5-hydroxy-methyl-bicyclo[2.2.2]oct-2-yl)-N-methyl-butyramide | 340 |
| 1-93 | 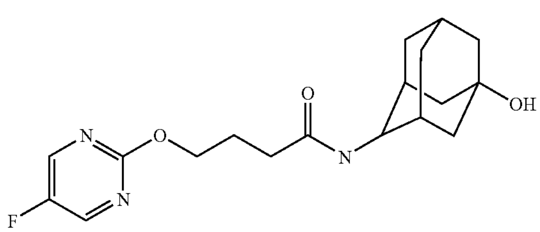 [SMILES: O=C(CCCOc1ncc(F)cn1)NC1C2CC3CC1CC(O)(C3)C2] | 349.41 | 4-(5-Fluoro-pyrimidin-2-yloxy)-N-(5-hydroxy-adamantan-2-yl)-butyramide | 236 |

Example 2-1

4-(2,4-Dichloro-phenoxy)-N-(5-hydroxy-adamantan-2-yl)-2,2-dimethyl-butyramide

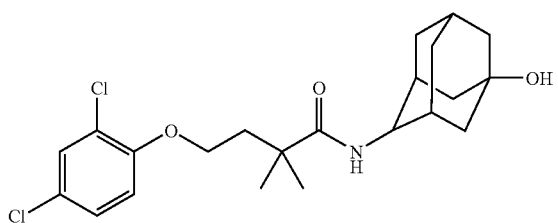 [SMILES: CC(C)(CCOc1ccc(Cl)cc1Cl)C(=O)NC1C2CC3CC1CC(O)(C3)C2]

To a stirred solution of 4-(2,4-dichloro-phenoxy)-2,2-dimethyl-butyric acid (250 g, 0.902 mmol, prepared in a similar way as described in *J. Am. Chem. Soc.* 89, 2500-1 (1967)) in dry DMF (3 mL) was added HOBt (180 mg, 1.173 mmol) and EDAC (225 mg, 1.173 mmol). After stirring for 1 hr at room temperature, DIPEA (306 µL) and 4-amino-adamantan-1-ol (181 mg, 1.082 mmol) were added and the resulting mixture was stirred for 16 hrs. at room temperature. The volatiles were removed in vacuo and the residue was purified using prep. HPLC/MS affording 153 mg (40%) of the title compound as a solid. $^1$H NMR (400 MHz, CDCl$_3$) ☐ 1.34 (s, 6H), 1.52 (q, 4H), 1.69-1.79 (m, 4H), 1.87 (d, 2H), 2.02-2.16 (m, 5H), 2.57 (br.s., 1H), 3.95-4.02 (m, 1H), 4.05 (t, 2H), 6.02 (d, 1H), 6.83 (d, 1H), 7.17 (dd, 1H), 7.35 (d, 1H).

m/z: 426.6 [M+1]+

The following compounds were made in a similar way as described in example 2-1.

| Example No | Structure | Mw | IUPAC Name | LC/MS |
|---|---|---|---|---|
| 2-2 | 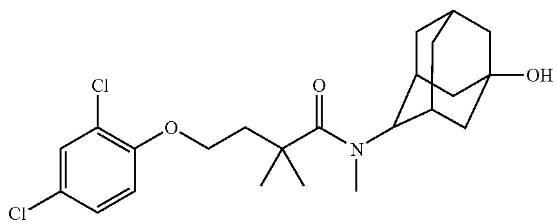 [SMILES: CN(C(=O)C(C)(C)CCOc1ccc(Cl)cc1Cl)C1C2CC3CC1CC(O)(C3)C2] | 440.41 | 4-(2,4-Dichloro-phenoxy)-N-(5-hydroxy-adamantan-2-yl)-2,2,N-trimethyl-butyramide | 441 |
| 2-3 | 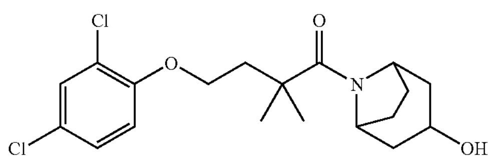 [SMILES: CC(C)(CCOc1ccc(Cl)cc1Cl)C(=O)N1C2CCC1CC(O)C2] | 386.32 | 4-(2,4-Dichloro-phenoxy)-1-(3-hydroxy-8-aza-bicyclo[3.2.1]oct-8-yl)-2,2-dimethyl-butan-1-one | 387 |
| 2-4 | 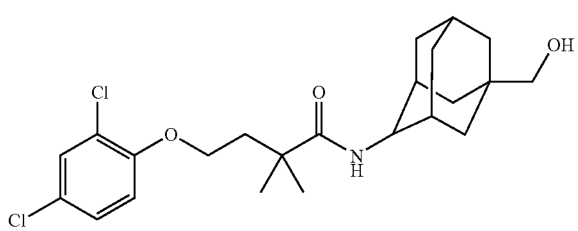 [SMILES: CC(C)(CCOc1ccc(Cl)cc1Cl)C(=O)NC1C2CC3CC1CC(CO)(C3)C2] | 440.41 | 4-(2,4-Dichloro-phenoxy)-N-(5-hydroxymethyl-adamantan-2-yl)-2,2-dimethyl-butyramide | 441 |
| 2-5 | 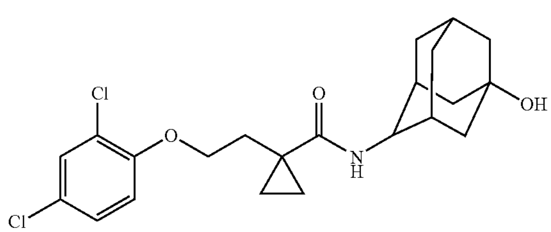 [SMILES: O=C(NC1C2CC3CC1CC(O)(C3)C2)C1(CCOc2ccc(Cl)cc2Cl)CC1] | 424.37 | 1-[2-(2,4-Dichloro-phenoxy)-ethyl]-cyclo-propanecarboxylic acid (5-hydroxy-adamantan-2-yl)-amide | 425 |

Example 3-1

2-(2,4-Dichloro-phenoxy-methanesulfonyl)-N-(5-hydroxy-adamantan-2-yl)-N-methylacetamide

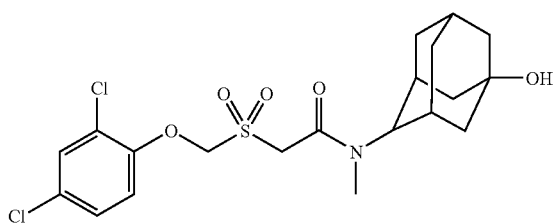 [SMILES: CN(C(=O)CS(=O)(=O)COc1ccc(Cl)cc1Cl)C1C2CC3CC1CC(O)(C3)C2]

To a solution of 2,4-dichloro-phenol (10 g, 61.35 mmol) in dry DMF (100 mL) was added NaH (2.06 g, 85.89 mmol, 60% in mineral oil). The mixture was stirred for 30 min. at room temperature followed by dropwise addition of chloromethylsulfanyl-methane (5.65 mL, 67.48 mmol) and stirring was continued for 16 hrs at ambient temperature. The reaction was quenched by addition of water (150 mL) and extracted with diethyl ether (2×100 mL). The combined organic phases were washed with saturated aq. ammonium chloride (2×100 mL), dried ($Na_2SO_4$), filtered and evaporated in vacuo afforded 17 g crude 2,4-dichloro-1-methylsulfanylmethoxy-benzene which was used without further purification in the next step.

To an ice cooled solution of the above crude 2,4-dichloro-1-methylsulfanylmethoxy-benzene (17 g) in DCM (200 mL) was added portion wise m-CPBA (13.8 g, 79.75 mmol) during 30 min. The resulting mixture was allowed to reach room temperature and stirring was continued for 16 hrs. The organic phase was washed with water (2×100 mL), 1N NaOH until pH 6-7, dried ($Na_2SO_4$), filtered and evaporated in vacuo. The residue was purified on silicagel (10 cm) using first heptane (1 L) followed by EtOAc:heptane (1:1) (1 L) and finally EtOAc as eluents. Pure fractions were collected from the pure EtOAc phase and evaporated in vacuo affording 10.1 g (69%) of 2,4-dichloro-1-methanesulfinylmethoxy-benzene as a solid.

$^1$H-NMR (400 MHz, CDCl$_3$) δ 2.76 (s, 3H), 5.00 (q, 2H), 7.20 (q, 2H), 7.40 (s, 1H).

To an ice-water cooled solution of 2,4-dichloro-1-methanesulfinylmethoxy-benzene (8 g, 33.46 mmol) in DCM (100 mL) was added dropwise a solution of acetylchloride (2.6 mL, 36.80 mmol) in DCM (10 mL). The reaction mixture was allowed to reach room temperature during 2 hrs at which time the volatiles were evaporated in vacuo affording ~7 g of crude 2,4-dichloro-1-chloromethoxy-benzene which was used without further purification.

To a solution of mercapto-acetic acid ethyl ester (2.4 g, 19.86 mmol) in dry DMF (20 mL) was added NaH (556 mg, 23.27 mmol, 60% in mineral oil). The mixture was stirred for 30 min. at room temperature followed by dropwise addition of 2,4-dichloro-1-chloromethoxy-benzene (3.5 g, 16.55 mmol), stirring was continued for 16 hrs at ambient temperature. The reaction was quenched by addition of water (50 mL) and extracted with diethyl ether (2×50 mL). The combined organic phases were washed with saturated aq. ammonium chloride (50 mL), dried ($Na_2SO_4$), filtered and evaporated in vacuo. The residue was dissolved in EtOH (20 mL) and to this solution was added aq. 32% NaOH (1 mL) and water (10 mL). Stirring was continued for 16 hrs at room temperature. The volatiles were evaporated in vacuo, water (20 mL) was added followed by washing with diethyl ether (20 mL). The aqueous phase was acidified to pH~1 with conc. HCl followed by extraction with diethyl ether (2×25 mL). The combined organic phases were dried ($Na_2SO_4$), filtered and the solvent evaporated in vacuo affording 2.5 g (57%) of crude (2,4-dichloro-phenoxymethylsulfanyl)-acetic acid as a solid.

m/z: 289 [M+23]+

To a stirred solution of (2,4-dichloro-phenoxymethylsulfanyl)-acetic acid (125 mg, 0.47 mmol) in dry THF (20 mL) was added HOBt (76 mg, 0.56 mmol) and EDAC (108 mg, 0.56 mmol). After stirring for 1 hr at room temperature, DIPEA (180 µL) and 4-methylaminoadamantan-1-ol (93 mg, 0.52 mmol) were added and the resulting mixture was stirred for 16 hrs. at room temperature. The volatiles were removed in vacuo and the residue was purified using prep. HPLC/MS affording crude 2-(2,4-dichloro-phenoxymethylsulfanyl)-N-(5-hydroxy-adamantan-2-yl)-N-methyl-acetamide which was used without further purification in the next step.

The crude sulfanyl was dissolved in AcOH (4 mL) and to this solution was added 35% $H_2O_2$ (1 mL). The mixture was stirred for 60 hrs and the volatiles were removed in vacuo. The residue was purified using prep. HPLC/MS affording 70 mg (32%) of the title compound as an oil.

$^1$H-NMR (400 MHz, CDCl$_3$) δ 1.50-1.62 (m, 1H), 1.61-1.97 (m, 9H), 2.19-2.30 (m, 2H), 2.30-2.48 (m, 2H), 3.22 (s, 3H), 4.13 (br.s., 1H), 4.33 (br.s., 2H), 5.35 (br.s., 2H), 7.11 (d, 1H), 7.22 (dd, 1H), 7.39 (d, 1H).

m/z: 462+464 [M]+

The following compounds were made in a similar way as described in example 3-1.

| Example No | Structure | Mw | IUPAC Name | LC/MS |
|---|---|---|---|---|
| 3-2 | 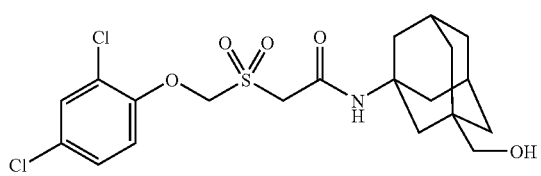 [SMILES: O=C(CS(=O)(=O)COc1ccc(Cl)cc1Cl)NC12CC3CC(CC(CO)(C3)C1)C2] | 462.40 | 2-(2,4-Dichloro-phenoxy-methanesulfonyl)-N-(3-hydroxymethyl-adamantan-1-yl)-acetamide | 463 |

| Example No | Structure | Mw | IUPAC Name | LC/MS |
|---|---|---|---|---|
| 3-3 | 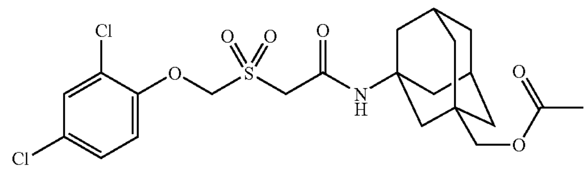 [SMILES: CC(=O)OCC12CC3CC(C1)CC(NC(=O)CS(=O)(=O)COc1ccc(Cl)cc1Cl)(C3)C2] | 504.43 | Acetic acid 3-[2-(2,4-dichloro-phenoxy-methanesulfonyl)-acetylamino]-adamantan-1-ylmethyl ester | 505 |

Pharmacological Methods
11βHSD1 Enzyme Assay
Materials $^3$H-cortisone and anti-rabbit Ig coated scintillation proximity assay (SPA) beads were purchased from Amersham Pharmacia Biotech, β-NADPH was from Sigma and rabbit anti-cortisol antibodies were from Fitzgerald. An extract of yeast transformed with h-11βHSD1 (Hutt et al., FEBS Lett., 441, 25 (1998)) was used as the source of enzyme. The test compounds were dissolved in DMSO (10 mM). All dilutions were performed in a buffer containing 50 mM TRIS-HCl (Sigma Chemical Co), 4 mM EDTA (Sigma Chemical Co), 0.1% BSA (Sigma Chemical Co), 0.01% Tween-20 (Sigma Chemical Co) and 0.005% bacitracin (Novo Nordisk NS), pH=7.4. Optiplate 96 wells plates were supplied by Packard. The amount of $^3$H-cortisol bound to the SPA beads was measured on TopCount NXT, Packard.

Methods h-11βHSD1, 120 nM $^3$H-cortisone, 4 mM β-NADPH, antibody (1:200), serial dilutions of test compound and SPA particles (2 mg/well) were added to the wells. The reaction was initiated by mixing the different components and was allowed to proceed under shaking for 60 min at 30° C. The reaction was stopped be the addition of 10 fold excess of a stopping buffer containing 500 μM carbenoxolone and 1 μM cortisone. Data was analysed using GraphPad Prism software.

TABLE 1

Inhibition of human 11βHSD1 by compounds of the invention

| Example No. | h-11βHSD1 IC$_{50}$ values (nM) |
|---|---|
| 1-1 | 27 |
| 1-3 | 405 |
| 1-4 | 296 |
| 1-10 | 201 |
| 1-11 | 271 |
| 1-15 | 52 |
| 1-17 | 7 |
| 1-18 | 209 |
| 1-19 | 24 |
| 1-20 | 13 |
| 1-21 | 1 |
| 1-22 | 6 |
| 1-23 | 151 |
| 1-24 | 20 |
| 1-25 | 185 |
| 1-26 | 21 |
| 1-27 | 4 |
| 1-28 | 1 |
| 1-29 | 14 |
| 1-30 | 10 |
| 1-31 | 11 |
| 1-32 | 4 |
| 1-33 | 7 |
| 1-34 | 172 |
| 1-35 | 252 |
| 1-36 | 397 |
| 1-37 | 1823 |
| 1-39 | 50 |
| 1-42 | 1342 |
| 1-43 | 58 |
| 1-45 | 9 |
| 1-46 | 1507 |
| 1-48 | 1078 |
| 1-49 | 141 |
| 1-51 | 61 |
| 1-52 | 54 |
| 1-53 | 194 |
| 1-54 | 10 |
| 1-55 | 2 |
| 1-56 | 322 |
| 1-57 | 628 |
| 1-58 | 55 |
| 1-59 | 3 |
| 1-60 | 1 |
| 1-61 | 56 |
| 1-62 | 123 |
| 1-64 | 2 |
| 1-65 | 4 |
| 1-66 | 3 |
| 1-67 | 25 |
| 1-68 | 17 |
| 1-69 | 2 |
| 1-70 | 479 |
| 1-71 | 21 |
| 1-72 | 198 |
| 1-73 | 1 |
| 1-74 | 809 |
| 1-75 | 27 |
| 1-76 | 18 |
| 1-78 | 23 |
| 1-79 | 300 |
| 1-80 | 700 |
| 1-81 | 187 |
| 1-82 | 4 |
| 1-83 | 9 |
| 1-84 | 30 |
| 1-87 | 227 |
| 2-1 | 2 |
| 2-3 | 206 |
| 2-4 | 3 |
| 2-5 | 4 |

While the invention has been described and illustrated with reference to certain preferred embodiments thereof, those skilled in the art will appreciate that various changes, modifications, and substitutions can be made therein without departing from the spirit and scope of the present invention. For example, effective dosages other than the preferred dosages as set forth herein may be applicable as a consequence of variations in the responsiveness of the mammal being treated.

Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Accordingly, the invention is not to be limited as by the appended claims.

The features disclosed in the foregoing description and/or in the claims may both separately ans in any combination thereof be material for realising the invention in diverse forms thereof.

Preferred features of the invention:
1. A compound of formula (I):

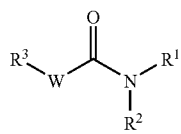

wherein
$R^1$ is hydrogen, methyl, ethyl, isopropyl and cyclopropyl;
$R^2$ is selected from one of the following structural elements:

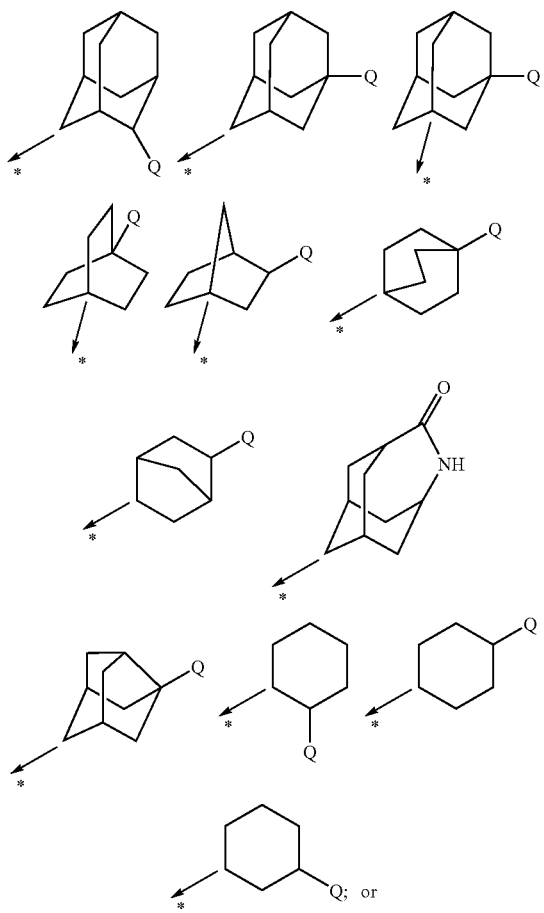

$R^2$ is selected from $C_1$-$C_6$alkyl, $C_3$-$C_{10}$cycloalkyl, aryl, hetaryl, arylC$_1$-C$_6$alkyl, and hetarylC$_1$-C$_6$alkyl, wherein each of the alkyl, cycloalkyl, aryl, and hetaryl groups are independently substituted with 0-3 $R^{11}$;

alternatively, $R^1$ and $R^2$ together with the nitrogen to which they are attached, is selected from the following structural elements:

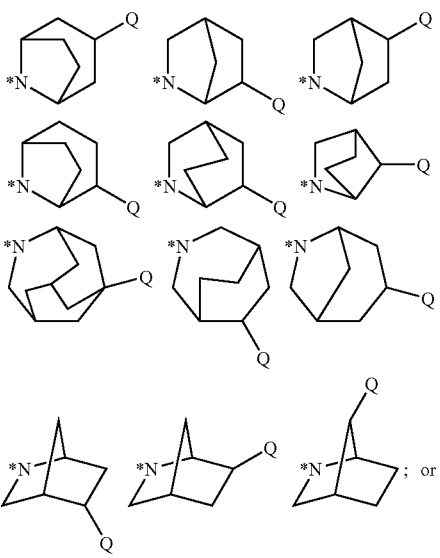

$R^1$ and $R^2$ together with the nitrogen to which they are attaced, form a 5-12 membered saturated or partially saturated monocyclic, bicyclic, or tricyclic ring consisting of the shown nitrogen, 4-10 carbon atoms, and 0-2 additional heteroatoms selected from nitrogen, oxygen, and S(O)$_m$, wherein this ring is substituted with 0-3 groups selected from $C_1$-$C_6$alkyl, $C_3$-$C_{10}$cycloalkyl, $C_3$-$C_{10}$hetcycloalkyl, $C_3$-$C_6$-spirocycloalkyl, 3-6 membered spirohetcycloalkyl, aryl, hetaryl, arylC$_1$-C$_6$alkyl, hetarylC$_1$-C$_6$alkyl, —C(=O)R$^{12}$, —S(O)$_n$R$^{12}$—OH, oxo, $C_1$-$C_6$alkyloxy, arylC$_1$-C$_6$alkyl-oxy, hetarylC$_1$-C$_6$alkyloxy, $C_1$-$C_6$alkyloxyC$_1$-C$_6$alkyl, $C_1$-$C_6$alkylcarboxy, arylcarboxy, hetarylcarboxy, arylC$_1$-C$_6$alkylcarboxy, and hetarylC$_1$-C$_6$alkylcarboxy, wherein each alkyl and aryl/hetaryl group is substituted with 0-3 $R^{11}$;

Q is selected from hydroxy, carboxy, hydroxymethylene, —SO$_2$NR$^4$R$^5$, —SO$_2$R$^6$, $C_1$-$C_6$alkyl, $C_3$-$C_6$cycloalkyl or —C(O)R$^6$; wherein the alkyl and cycloalkyl groups are optionally substituted with hydroxy, —OC(=O)CH$_3$ or —C(=O)OCH$_3$;

W is —Y—(CR$^7$R$^8$)$_n$—X—(CR$^9$R$^{10}$)$_m$—;
X is a chemical bond or S(O)$_n$;
Y is O or S;
m is 0, 1 or 2;
n is 1 or 2;
$R^3$ is selected from $C_3$-$C_{10}$cycloalkyl, 3-10 membered heterocycloalkyl, aryl or hetaryl, wherein the alkyl, cycloalkyl, aryl and hetaryl groups are independently substituted with 0-3 $R^{11}$;

$R^4$ and $R^5$ are independently selected from hydrogen, $C_1$-$C_6$alkyl, $C_3$-$C_{10}$cycloalkyl, aryl, hetaryl, arylC$_1$-C$_6$alkyl, and hetarylC$_1$-C$_6$alkyl, wherein each of the alkyl, cycloalkyl, aryl, and hetaryl groups are independently substituted with 0-3 $R^{11}$;

alternatively, $R^4$ and $R^5$ together with the nitrogen to which they are attaced, form a 5-12 membered saturated or partially saturated monocyclic, bicyclic, or tricyclic ring consisting of the shown nitrogen, 4-10 carbon atoms, and 0-2 additional heteroatoms selected from nitrogen, oxygen, and S(O)$_m$, wherein this ring is substituted with 0-3 groups selected from C$_1$-C$_6$alkyl, aryl, hetaryl, arylC$_1$-C$_6$alkyl, hetarylC$_1$-C$_6$alkyl, OH, oxo, C$_1$-C$_6$alkyloxy, arylC$_1$-C$_6$alkyloxy, hetarylC$_1$-C$_6$alkyloxy, C$_1$-C$_6$alkyloxoC$_1$-C$_6$alkyl, C$_1$-C$_6$alkylcarbonyl, arylcarbonyl, hetarylcarbonyl, arylC$_1$-C$_6$alkylcarbonyl, hetarylC$_1$-C$_6$alkylcarbonyl, C$_1$-C$_6$alkylcarboxy, arylcarboxy, hetarylcarboxy, arylC$_1$-C$_6$alkylcarboxy, and hetarylC$_1$-C$_6$alkylcarboxy;

R$^6$ is selected from OH, C$_1$-C$_6$alkyl, C$_3$-C$_{10}$cycloalkyl, 3-10 membered heterocycloalkyl, trihalomethyl, trihalomethyloxy, C$_1$-C$_6$alkyloxy, aryl, aryloxy, arylC$_1$-C$_6$alkyl, arylC$_1$-C$_6$alkyloxy, hetaryl, hetaryloxy, hetarylC$_1$-C$_6$alkyl, hetarylC$_1$-C$_6$alkyloxy, and NR$^4$R$^5$;

R$^7$ and R$^8$ are independently selected from hydrogen, halo, cyano, trihalomethyl, trihalomethyloxy, C$_1$-C$_6$alkyl, C$_3$-C$_6$cycloalkyl, 3-10 membered hetcycloalkyl, aryl, hetaryl, arylC$_1$-C$_6$alkyl, hetarylC$_1$-C$_6$alkyl, —C(O)R$^6$, —S(O)$_n$R$^6$, —S(O)$_n$NR$^4$R$^5$, —N(R$^4$)S(O)$_n$R$^6$, —N(R$^4$)C(O)NR$^4$R$^5$, OH, oxo, C$_1$-C$_6$alkyloxy, arylC$_1$-C$_6$alkyloxy, hetarylC$_1$-C$_6$alkyloxy, C$_1$-C$_6$alkyloxoC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, cycloalkyl and aryl/hetaryl group is optionally substituted with 0-3 R$^{12}$;

alternatively, R$^7$ and R$^8$ together with the carbon atom to which they are attached forms a C$_3$-C$_6$cycloalkyl or a 3-10 membered hetcycloalkyl ring optionally substituted with 0-3 R$^{12}$;

R$^9$ and R$^{10}$ are selected from hydrogen, halo, cyano, trihalomethyl, trihalomethyloxy, C$_1$-C$_6$alkyl, C$_3$-C$_6$cycloalkyl, 3-10 membered hetcycloalkyl, aryl, hetaryl, arylC$_1$-C$_6$alkyl, hetarylC$_1$-C$_6$alkyl, —C(O)R$^6$, —S(O)$_n$R$^6$, —S(O)$_n$NR$^4$R$^5$, —N(R$^4$)S(O)$_n$R$^6$, —N(R$^4$)C(O)NR$^4$R$^5$, OH, oxo, C$_1$-C$_6$alkyloxy, arylC$_1$-C$_6$alkyloxy, hetarylC$_1$-C$_6$alkyloxy, C$_1$-C$_6$alkyloxoC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, cycloalkyl and aryl/hetaryl group is optionally substituted with 0-3 R$^{12}$;

alternatively, R$^9$ and R$^{10}$ together with the carbon atom to which they are attached forms a C$_3$-C$_6$cycloalkyl or a 3-10 membered hetcycloalkyl ring optionally substituted with 0-3 R$^{12}$;

R$^{11}$ is selected from halo, cyano, trihalomethyl, trihalomethyloxy, C$_1$-C$_6$alkyl, C$_3$-C$_6$cycloalkyl, 3-10 membered hetcycloalkyl, C$_3$-C$_6$-spirocycloalkyl, 3-6 membered spirohetcycloalkyl, aryl, hetaryl, arylC$_1$-C$_6$alkyl, hetarylC$_1$-C$_6$alkyl, —C(O)R$^6$, —S(O)$_n$R$^6$, —S(O)$_n$NR$^4$R$^5$, —N(R$^4$)S(O)$_n$R$^6$, —N(R$^4$)C(O)NR$^4$R$^5$, OH, oxo, C$_1$-C$_6$alkyloxy, arylC$_1$-C$_6$alkyloxy, hetarylC$_1$-C$_6$alkyloxy, C$_1$-C$_6$alkyloxoC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, cycloalkyl and aryl/hetaryl group is optionally substituted with 0-3 R$^{12}$;

R$^{12}$ is selected from halo, OH, oxo, COOH, cyano, C$_1$-C$_6$alkyloxy, trihalomethyl, C$_3$-C$_{10}$-cycloalkyloxy, aryloxy, hetaryloxy, hetarylthio and arylC$_1$-C$_6$alkyloxy;

or a salt thereof with a pharmaceutically acceptable acid or base, or any optical isomer or mixture of optical isomers, including a racemic mixture, or any tautomeric forms.

2. A compound of formula (I):

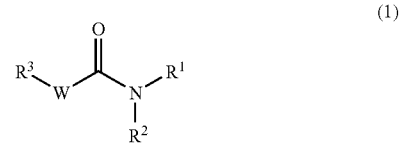

wherein

R$^1$ is hydrogen, methyl, ethyl, isopropyl and cyclopropyl;

R$^2$ is selected from one of the following structural elements:

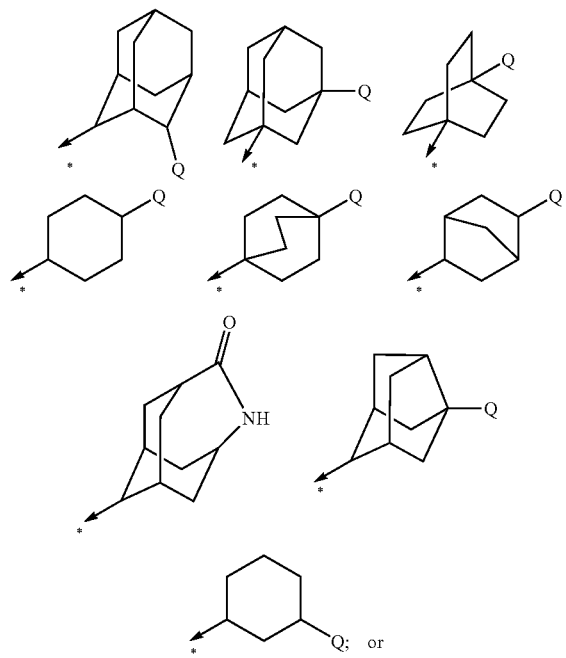

R$^2$ is selected from C$_1$-C$_6$alkyl, C$_3$-C$_{10}$cycloalkyl, aryl, hetaryl, arylC$_1$-C$_6$alkyl, and hetarylC$_1$-C$_6$alkyl, wherein each of the alkyl, cycloalkyl, aryl, and hetaryl groups are independently substituted with 0-3 R$^{11}$;

alternatively, R$^1$ and R$^2$ together with the nitrogen to which they are attached, is selected from the following structural elements:

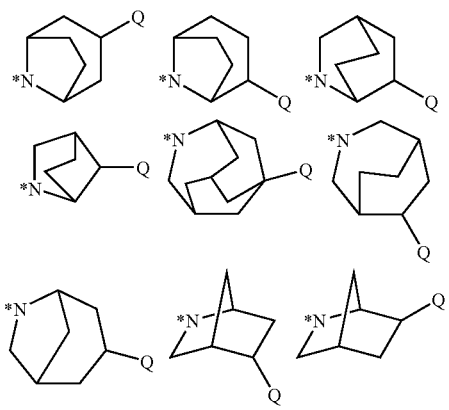

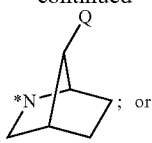; or $R^1$ and $R^2$ together with the nitrogen to which they are attaced, form a 5-12 membered saturated or partially saturated monocyclic, bicyclic, or tricyclic ring consisting of the shown nitrogen, 4-10 carbon atoms, and 0-2 additional heteroatoms selected from nitrogen, oxygen, and $S(O)_m$, wherein this ring is substituted with 0-3 groups selected from $C_1$-$C_6$alkyl, $C_3$-$C_{10}$cycloalkyl, $C_3$-$C_{10}$hetcycloalkyl, $C_3$-$C_6$-spirocycloalkyl, 3-6 membered spirohetcycloalkyl, aryl, hetaryl, arylC$_1$-C$_6$alkyl, hetarylC$_1$-C$_6$alkyl, —C(=O)R$^{12}$, —S(O)$_n$R$^{12}$—OH, oxo, $C_1$-$C_6$alkyloxy, arylC$_1$-C$_6$alkyl-oxy, hetarylC$_1$-C$_6$alkyloxy, $C_1$-$C_6$alkyloxyC$_1$-C$_6$alkyl, $C_1$-$C_6$alkylcarboxy, arylcarboxy, hetarylcarboxy, arylC$_1$-C$_6$alkylcarboxy, and hetarylC$_1$-C$_6$alkylcarboxy, wherein each alkyl and aryl/hetaryl group is substituted with 0-3 $R^{11}$;

Q is selected from hydroxy, carboxy, hydroxymethylene, —SO$_2$NR$^4$R$^5$, $C_1$-$C_6$alkyl, $C_3$-$C_6$-cycloalkyl or —C(O) $R^6$; wherein the alkyl, and cycloalkyl groups are optionally substituted with hydroxy;

W is —Y—(CR$^7$R$^8$)$_n$—X—(CR$^9$R$^{10}$)$_m$—;

X is a chemical bond or $S(O)_n$;

Y is O or S;

m is 0, 1 or 2;

n is 1 or 2;

$R^3$ is selected from $C_3$-$C_{10}$cycloalkyl, 3-10 membered heterocycloalkyl, aryl or hetaryl, wherein the alkyl, cycloalkyl, aryl and hetaryl groups are independently substituted with 0-3 $R^{11}$;

$R^4$ and $R^5$ are independently selected from hydrogen, $C_1$-$C_6$alkyl, $C_3$-$C_{10}$cycloalkyl, aryl, hetaryl, arylC$_1$-C$_6$alkyl, and hetarylC$_1$-C$_6$alkyl, wherein each of the alkyl, cycloalkyl, aryl, and hetaryl groups are independently substituted with 0-3 $R^{11}$;

alternatively, $R^4$ and $R^5$ together with the nitrogen to which they are attaced, form a 5-12 membered saturated or partially saturated monocyclic, bicyclic, or tricyclic ring consisting of the shown nitrogen, 4-10 carbon atoms, and 0-2 additional heteroatoms selected from nitrogen, oxygen, and $S(O)_m$, wherein this ring is substituted with 0-3 groups selected from $C_1$-$C_6$alkyl, aryl, hetaryl, arylC$_1$-C$_6$alkyl, hetarylC$_1$-C$_6$alkyl, OH, oxo, $C_1$-$C_6$alkyloxy, arylC$_1$-C$_6$alkyloxy, hetarylC$_1$-C$_6$alkyloxy, $C_1$-$C_6$alkyloxoC$_1$-C$_6$alkyl, $C_1$-$C_6$alkylcarbonyl, arylcarbonyl, hetarylcarbonyl, arylC$_1$-C$_6$alkylcarbonyl, hetarylC$_1$-C$_6$alkylcarbonyl, $C_1$-$C_6$alkylcarboxy, arylcarboxy, hetarylcarboxy, arylC$_1$-C$_6$alkylcarboxy, and hetarylC$_1$-C$_6$alkylcarboxy;

$R^6$ is selected from OH, $C_1$-$C_6$alkyl, $C_3$-$C_{10}$cycloalkyl, 3-10 membered heterocycloalkyl, trihalomethyl, trihalomethyloxy, $C_1$-$C_6$alkyloxy, aryl, aryloxy, arylC$_1$-C$_6$alkyl, arylC$_1$-C$_6$alkyloxy, hetaryl, hetaryloxy, hetarylC$_1$-C$_6$alkyl, hetarylC$_1$-C$_6$alkyloxy, and NR$^4$R$^5$;

$R^7$ and $R^8$ are independently selected from hydrogen, halo, cyano, trihalomethyl, trihalomethyloxy, $C_1$-$C_6$alkyl, $C_3$-$C_6$cycloalkyl, 3-10 membered hetcycloalkyl, aryl, hetaryl, arylC$_1$-C$_6$alkyl, hetarylC$_1$-C$_6$alkyl, —C(O)R$^6$, —S(O)$_n$R$^6$, —S(O)$_n$NR$^4$R$^5$, —N(R$^4$)S(O)$_n$R$^6$, N(R$^4$)C(O)NR$^4$R$^5$, OH, oxo, $C_1$-$C_6$alkyloxy, arylC$_1$-C$_6$alkyloxy, hetarylC$_1$-C$_6$alkyloxy, $C_1$-$C_6$alkyloxoC$_1$-C$_6$alkyl, $C_1$-$C_6$alkylcarboxy, arylcarboxy, hetarylcarboxy, arylC$_1$-C$_6$alkylcarboxy, and hetarylC$_1$-C$_6$alkylcarboxy, wherein each alkyl, cycloalkyl and aryl/hetaryl group is optionally substituted with 0-3 $R^{12}$;

alternatively, $R^7$ and $R^8$ together with the carbon atom to which they are attached forms a $C_3$-$C_6$cycloalkyl or a 3-10 membered hetcycloalkyl ring optionally substituted with 0-3 $R^{12}$;

$R^9$ and $R^{10}$ are selected from hydrogen, halo, cyano, trihalomethyl, trihalomethyloxy, $C_1$-$C_6$alkyl, $C_3$-$C_6$cycloalkyl, 3-10 membered hetcycloalkyl, aryl, hetaryl, arylC$_1$-C$_6$alkyl, hetarylC$_1$-C$_6$alkyl, —C(O)R$^6$, —S(O)$_n$R$^6$, —S(O)$_n$NR$^4$R$^5$, —N(R$^4$)S(O)$_n$R$^6$, —N(R$^4$)C(O)NR$^4$R$^5$, OH, oxo, $C_1$-$C_6$alkyloxy, arylC$_1$-C$_6$alkyloxy, hetarylC$_1$-C$_6$alkyloxy, $C_1$-$C_6$alkyloxoC$_1$-C$_6$alkyl, $C_1$-$C_6$alkylcarboxy, arylcarboxy, hetarylcarboxy, arylC$_1$-C$_6$alkylcarboxy, and hetarylC$_1$-C$_6$alkylcarboxy, wherein each alkyl, cycloalkyl and aryl/hetaryl group is optionally substituted with 0-3 $R^{12}$;

alternatively, $R^9$ and $R^{10}$ together with the carbon atom to which they are attached forms a $C_3$-$C_6$cycloalkyl or a 3-10 membered hetcycloalkyl ring optionally substituted with 0-3 $R^{12}$; $R^{11}$ is selected from halo, cyano, trihalomethyl, trihalomethyloxy, $C_1$-$C_6$alkyl, $C_3$-$C_6$cycloalkyl, 3-10 membered hetcycloalkyl, $C_3$-$C_6$-spirocycloalkyl, 3-6 membered spirohetcycloalkyl, aryl, hetaryl, arylC$_1$-C$_6$alkyl, hetarylC$_1$-C$_6$alkyl, —C(O)R$^6$, —S(O)$_n$R$^6$, —S(O)$_n$NR$^4$R$^5$, N(R$^4$)S(O)$_n$R$^6$, —N(R$^4$)C(O)NR$^4$R$^5$, OH, oxo, $C_1$-$C_6$alkyloxy, arylC$_1$-C$_6$alkyloxy, hetarylC$_1$-C$_6$alkyloxy, $C_1$-$C_6$alkyloxoC$_1$-C$_6$alkyl, $C_1$-$C_6$alkylcarboxy, arylcarboxy, hetarylcarboxy, arylC$_1$-C$_6$alkylcarboxy, and hetarylC$_1$-C$_6$alkylcarboxy, wherein each alkyl, cycloalkyl and aryl/hetaryl group is optionally substituted with 0-3 $R^{12}$;

$R^{11}$ is selected from halo, hydroxy, oxo, —COOH, —S(O)$_n$R$^{13}$, cycloalkyl, —OR$^{13}$, $C_1$-$C_6$alkyl, $C_1$-$C_6$alkyloxy, aryl and hetaryl, wherein $R^{13}$ is $C_1$-$C_6$alkyl; and wherein each alkyl, cycloalkyl and aryl, hetaryl group is optionally substituted with 0-3 $R^{12}$;

$R^{12}$ is selected from halo, OH, oxo, COOH, cyano, $C_1$-$C_6$alkyloxy, trihalomethyl, $C_3$-$C_{10}$-cycloalkyloxy, aryloxy, hetaryloxy, hetarylthio and arylC$_1$-C$_6$alkyloxy;

or a salt thereof with a pharmaceutically acceptable acid or base, or any optical isomer or mixture of optical isomers, including a racemic mixture, or any tautomeric forms.

3. The compound according to clause 1, wherein $R^2$ is selected from:

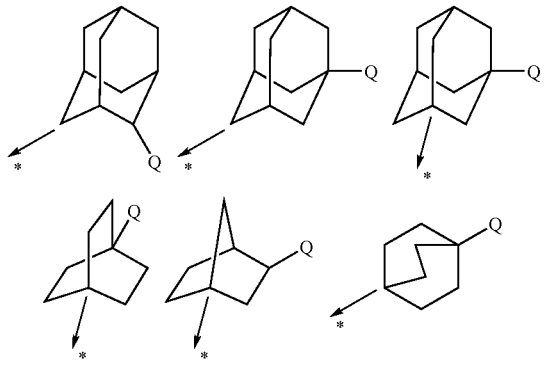

-continued

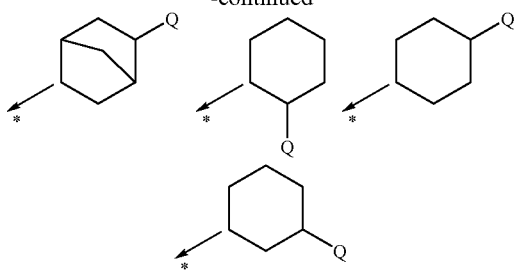

4. The compound according to clause 1 or 2, wherein R² is selected from:

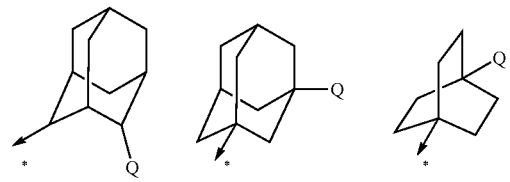

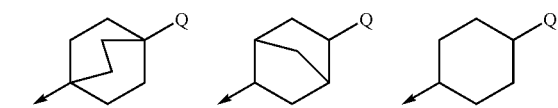

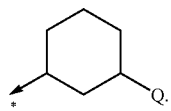

5. The compound according to clause 1 or 3, wherein R² is selected from:

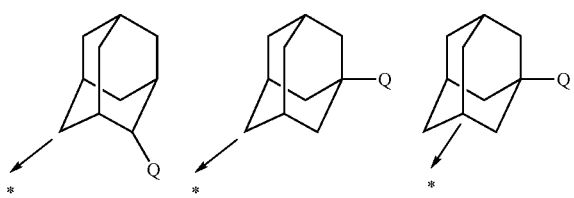

6. The compound according to clause 1 or 3, wherein R² is selected from:

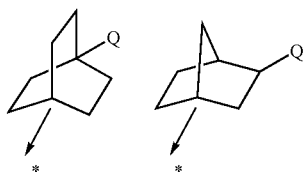

7. The compound according to clause 1 or 3, wherein R² is selected from:

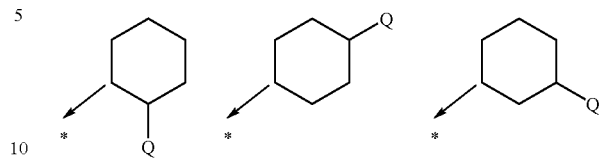

8. The compound according to any one of the clauses 1-3, wherein R² is:

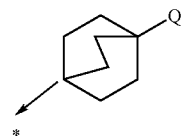

9. The compound according to any one of the clauses 1-3, wherein R² is:

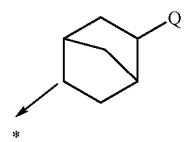

10. The compound according to any one of the clauses 1-9, wherein R¹ and R² together with the nitrogen to which they are attaced attached, is selected from the following structural elements:

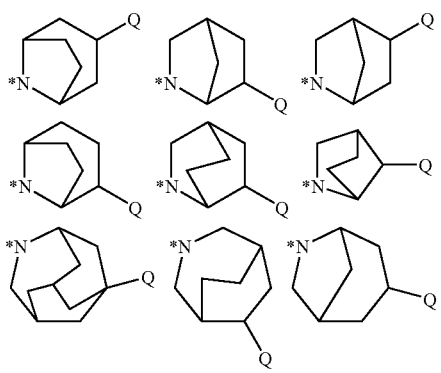

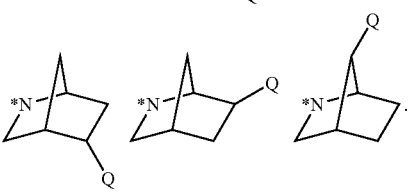

11. The compound according to clause 1, wherein R¹ and R² together with the nitrogen to which they are attaced attached, is selected from the following structural elements:

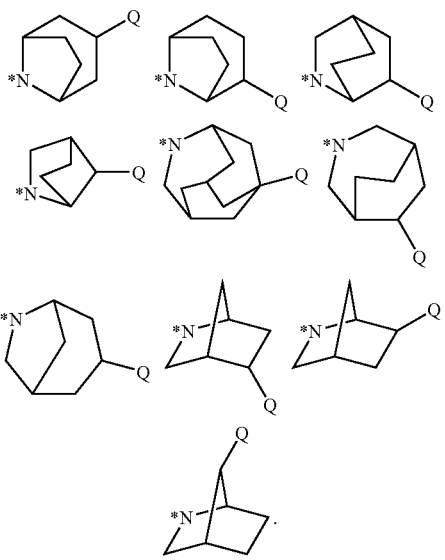

12. The compound according to any one of the clauses 1-10, wherein $R^1$ and $R^2$ together with the nitrogen to which they are attaced attached, is selected from the following structural elements:

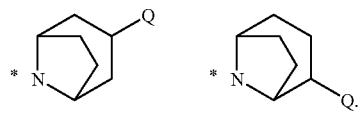

13. The compound according to any one of the clauses 1-10, wherein $R^1$ and $R^2$ together with the nitrogen to which they are attaced attached, is selected from the following structural elements:

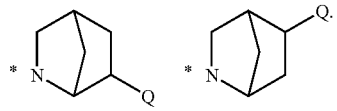

14. The compound according to any one of the clauses 1-10, wherein $R^1$ and $R^2$ together with the nitrogen to which they are attaced attached, is selected from the following structural elements:

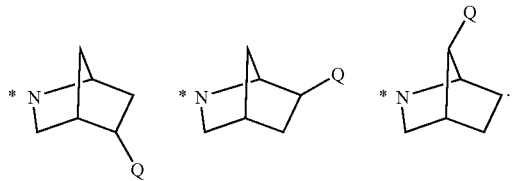

15. The compound according to any one of the clauses 1-10, wherein $R^1$ and $R^2$ together with the nitrogen to which they are attaced attached, is selected from the following structural elements:

16. The compound according to any one of the clauses 1-10, wherein $R^1$ and $R^2$ together with the nitrogen to which they are attaced attached, is selected from the following structural elements:

17. The compound according to any one of the clauses 1-10, wherein $R^1$ and $R^2$ together with the nitrogen to which they are attaced attached, is selected from the following structural elements:

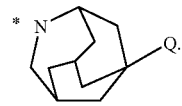

18. The compound according to any one of the clauses 1-10, wherein $R^1$ and $R^2$ together with the nitrogen to which they are attaced attached, is selected from the following structural elements:

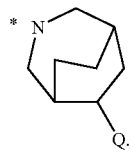

19. The compound according to any one of the clauses 1-10, wherein $R^1$ and $R^2$ together with the nitrogen to which they are attaced attached, is selected from the following structural elements:

20. The compound according to any one of the clauses 1-19, wherein $R^3$ is selected from $C_3$-$C_{10}$cycloalkyl or 3-10 membered heterocycloalkyl each of which is substituted with 0-3 $R^{11}$.
21. The compound according to any one of the clauses 1-19, wherein $R^3$ is selected from aryl or hetaryl, each of which is optionally substituted.
22. The compound according to any one of the clauses 1-21, wherein Q is selected from hydroxy, carboxy, —SO$_2$R$^6$, $C_1$-$C_6$alkyl, $C_3$-$C_6$cycloalkyl or —C(O)R$^6$; wherein the alkyl and cycloalkyl groups are optionally substituted with hydroxy, —OC(=O)CH$_3$ or —C(=O)OCH$_3$;
23. The compound according to clause 22, wherein Q is selected from hydroxy, carboxy, $C_1$-$C_6$alkyl, C$_3$-C$_6$cycloalkyl or —C(O)R$^6$; wherein the alkyl, and cycloalkyl groups are optionally substituted with hydroxy.

24. The compound according to any one of the clauses 1-23 wherein the compound is selected from the group consisting of:

1-[2-(4-Chloro-phenyl)-pyrrolidin-1-yl]-4-(2,4-dichloro-phenoxy)-butan-1-one;
N-(Cyclopropyl-phenyl-methyl)-4-(2,4-dichloro-phenoxy)-butyramide;
1-[2-(2-Chloro-phenyl)-piperidin-1-yl]-4-(2,4-dichloro-phenoxy)-butan-1-one;
4-(2,4-Dichloro-phenoxy)-N-(1-phenyl-cyclobutyl)-butyramide;
4-(2,4-Dichloro-phenoxy)-N-(1-phenyl-cyclopropyl)-butyramide;
4-(2,4-Dichloro-phenoxy)-N-[1-(3-trifluoromethyl-phenyl)-cyclopropyl]butyramide;
N-[1-(3-Chloro-phenyl)-cyclobutyl]-4-(2,4-dichloro-phenoxy)-butyramide;
4-(2,4-Dichloro-phenoxy)-1-(4-phenyl-piperidin-1-yl)-butan-1-one;
4-(2,4-Dichloro-phenoxy)-1-(2-phenyl-piperidin-1-yl)-butan-1-one;
4-(2,4-Dichloro-phenoxy)-N-((1S,2R,5S)-6,6-dimethyl-bicyclo[3.1.1]hept-2-ylmethyl)butyramide;
N-[(1R,2R)-2-(4-Chloro-phenyl)-cyclopentyl]-4-(2,4-dichloro-phenoxy)-butyramide;
N-[(1R,2S)-2-(4-Chloro-phenyl)-cyclopentyl]-4-(2,4-dichloro-phenoxy)-butyramide;
4-(2,4-Dichloro-phenoxy)-N-(2-phenyl-cyclopentyl)-butyramide;
1-(3-Aza-bicyclo[3.2.2]non-3-yl)-4-(2,4-di-chloro-phenoxy)-butan-1-one;
(1S,2R,3S,4R)-3-[4-(2,4-Dichloro-phenoxy)-butyrylamino]-bicyclo-[2.2.1]heptane-2-carboxylic acid ethyl ester;
8-[4-(2,4-Dichloro-phenoxy)-butyryl]-8-aza-bicyclo[3.2.1]octane-3-carboxylic acid methyl ester;
N-Cyclopropyl-4-(2,4-dichloro-phenoxy)-N-(5-hydroxy-adamantan-2-yl)-butyramide;
N-Cyclopropyl-4-(2,4-dichloro-phenoxy)-N-(5-hydroxy-adamantan-2-yl)-butyramide;
4-(2,4-Dichloro-phenoxy)-N-(5-hydroxy-adamantan-2-yl)-2,2,N-trimethyl-butyramide;
3-[4-(2,4-Dichloro-phenoxy)-butyrylamino]-adamantane-1-carboxylic acid;
4-(2,4-Dichloro-phenoxy)-N-(5-hydroxy-methyl-adamantan-2-yl)-2,2-dimethyl-butyramide;
4-(2,4-Dichloro-phenoxy)-N-(5-hydroxy-adamantan-2-yl)-2,2-dimethyl-butyramide;
4-(2,4-Dichloro-phenoxy)-N-(4-hydroxy-methyl-adamantan-2-yl)-butyramide;
4-(2,4-Dichloro-phenoxy)-1-(1-hydroxy-4-aza-tricyclo[4.3.1.1{3,8}]undec-4-yl)-butan-1-one;
4-(2,4-Dichloro-phenoxy)-1-(3-hydroxy-8-aza-bicyclo[3.2.1]oct-8-yl)-2,2-dimethyl-butan-1-one;
1-[2-(2,4-Dichloro-phenoxy)-ethyl]cyclo-propanecarboxylic acid (5-hydroxy-adamantan-2-yl)-amide;
2-(2,4-Dichloro-phenoxy-methanesulfonyl)-N-(5-hydroxy-adamantan-2-yl)-N-methylacetamide;
2-(2,4-Dichloro-phenoxy-methanesulfonyl)-N-(3-hydroxymethyl-adamantan-1-yl)-acetamide; Acetic acid 3-[2-(2,4-dichloro-phenoxy-methanesulfonyl)-acetylamino]-adamantan-1-ylmethyl ester;
4-(2,4-Dichloro-phenoxy)-1-(6-hydroxy-2-aza-bicyclo[2.2.1]hept-2-yl)-butan-1-one;
4-(2,4-Dichloro-phenoxy)-1-(5-hydroxy-2-aza-bicyclo[2.2.1]hept-2-yl)-butan-1-one;
4-(2,4-Dichloro-phenoxy)-1-(3-hydroxy-6-aza-bicyclo[3.2.1]oct-6-yl)-butan-1-one;
4-(2,4-Dichloro-phenoxy)-N-(4-hydroxy-cyclohexyl)-N-methyl-butyramide;
4-(2,4-Dichloro-phenoxy)-N-(5-hydroxy-adamantan-2-yl)-butyramide;
4-(2,4-Dichloro-phenoxy)-N-(3-hydroxy-methyl-adamantan-1-yl)-butyramide;
4-(2,4-Dichloro-phenoxy)-1-(7-hydroxy-2-aza-bicyclo[2.2.1]hept-2-yl)-butan-1-one;
3-[4-(2,4-Dichloro-phenoxy)-butyrylamino]-adamantane-1-carboxylic acid methyl ester;
3-[4-(2,4-Dichloro-phenoxy)-butyrylamino]-adamantane-1-carboxylic acid;
4-(2,4-Dichloro-phenoxy)-N-(5-hydroxy-adamantan-2-yl)-N-methyl-butyramide;
4-(2,4-Dichloro-phenoxy)-N-ethyl-N-(5-hydroxy-adamantan-2-yl)-butyramide;
4-(2,4-Dichloro-phenoxy)-N-ethyl-N-(5-hydroxy-adamantan-2-yl)-butyramide;
4-(2,4-Dichloro-phenoxy)-1-(8-hydroxy-3-aza-bicyclo[3.2.1]oct-3-yl)-butan-1-one;
4-(2,4-Dichloro-phenoxy)-1-(5-hydroxy-2-aza-bicyclo[2.2.2]oct-2-yl)-butan-1-one;
N-(4-Hydroxy-cyclohexyl)-N-methyl-4-phenoxy-butyramide;
N-(5-Hydroxy-adamantan-2-yl)-4-phenoxy-butyramide;
N-(5-Hydroxy-adamantan-2-yl)-4-phenoxy-butyramide;
1-(5-Hydroxy-2-aza-bicyclo[2.2.2]oct-2-yl)-4-phenoxy-butan-1-one;
1-(8-Hydroxy-3-aza-bicyclo[3.2.1]oct-3-yl)-4-phenoxy-butan-1-one;
N-(5-Hydroxy-adamantan-2-yl)-N-methyl-4-phenoxy-butyramide;
N-(5-Hydroxy-adamantan-2-yl)-N-methyl-4-phenoxy-butyramide;
1-(3-Hydroxy-6-aza-bicyclo[3.2.1]oct-6-yl)-4-phenoxy-butan-1-one;
N-(3-Hydroxymethyl-adamantan-1-yl)-4-phenoxy-butyramide;
1-(5-Hydroxy-2-aza-bicyclo[2.2.1]hept-2-yl)-4-phenoxy-butan-1-one;
1-(6-Hydroxy-2-aza-bicyclo[2.2.1]hept-2-yl)-4-phenoxy-butan-1-one;
1-(7-Hydroxy-2-aza-bicyclo[2.2.1]hept-2-yl)-4-phenoxy-butan-1-one;
N-(5-Hydroxy-adamantan-2-yl)-N-isopropyl-4-phenoxy-butyramide;
N-Ethyl-N-(5-hydroxy-adamantan-2-yl)-4-phenoxy-butyramide;
N-Ethyl-N-(5-hydroxy-adamantan-2-yl)-4-phenoxy-butyramide;
3-(4-Phenoxy-butyryl-amino)adamantane-1-carboxylic acid methyl ester;
3-(4-Phenoxy-butyryl-amino)-adamantane-1-carboxylic acid;
N-(5-Hydroxymethyl-adamantan-2-yl)-4-phenoxy-butyramide;
4-(2,4-Dichloro-phenoxy)-N-(5-hydroxy-methyl-adamantan-2-yl)-butyramide;
4-(2,4-Dichloro-phenoxy)-N-(5-hydroxy-adamantan-2-yl)-N-isopropyl-butyramide;
4-(2,4-Dichloro-phenoxy)-N-((1S,2S)-2-hydroxy-cyclohexyl)-N-methyl-butyramide;

3-{[4-(2,4-Dichloro-phenoxy)-butyryl]-methyl-amino}-cyclo-hexanecarboxylic acid;
4-(2,4-Dichloro-phenoxy)-N-(3-hydroxy-methyl-cyclohexyl)-N-methyl-butyramide;
4-(2,4-Dichloro-phenoxy)-N-(4-hydroxy-methyl-cyclohexyl)-N-methyl-butyramide;
4-(2,4-Dichloro-phenoxy)-N-(3-hydroxy-cyclohexyl)-N-methyl-butyramide;
4-(2,4-Dichloro-phenoxy)-N—((S)-2-hydroxymethyl-cyclo-hexyl)-N-methyl-butyramide;
(S)-2-{(R)-[4-(2,4-Dichloro-phenoxy)-butyryl]methyl-amino}-cyclohexanecarboxylic acid;
4-(2,4-Dichloro-phenoxy)-N-(5-hydroxy-bicyclo[2.2.1]hept-2-yl)-N-methyl-butyramide;
4-(2,4-Dichloro-phenoxy)-N-(5-hydroxy-methyl-adamantan-2-yl)-N-methyl-butyramide;
4-[4-(2,4-Dichloro-phenoxy)-butyryl]-4-aza-tricyclo[4.3.1.1{3,8}]undecane-1-carboxylic acid methyl ester;
4-[4-(2,4-Dichloro-phenoxy)-butyryl]-4-aza-tricyclo[4.3.1.1{3,8}]undecane-1-carboxylic acid;
4-[4-(2,4-Dichloro-phenoxy)-butyrylamino]-adamantane-1-carboxylic acid methyl ester;
4-(2,4-Dichloro-phenoxy)-N-methyl-N-(4-sulfamoyl-cyclohexyl)-butyramide;
4-(2,4-Dichloro-phenoxy)-N-(4-dimethyl-sulfamoyl-cyclohexyl)-N-methyl-butyramide;
4-(2,4-Dichloro-phenoxy)-N-(4-dimethyl-sulfamoyl-cyclohexyl)-N-methyl-butyramide;
4-[4-(2,4-Dichloro-phenoxy)-butyrylamino]bicyclo[2.2.2]octane-1-carboxylic acid ethyl ester;
4-(2,4-Dichloro-phenoxy)-N-(4-hydroxy-methyl-bicyclo[2.2.2]oct-1-yl)-butyramide;
4-{[4-(2,4-Dichloro-phenoxy)-butyryl]-methyl-amino}-cyclo-hexanecarboxylic acid;
4-(2,4-Dichloro-phenoxy)-N-(4-hydroxy-methyl-cyclohexyl)-butyramide;
4-{[4-(2,4-Dichloro-phenoxy)-butyryl]-methyl-amino}-cyclo-hexanecarboxylic acid amide;
4-{[4-(2,4-Dichloro-phenoxy)-butyryl]-methyl-amino}-cyclo-hexanecarboxylic acid dimethylamide;
4-(2,4-Dichloro-phenoxy)-N-[4-(1-hydroxy-1-methyl-ethyl)-cyclohexyl]-N-methyl-butyramide;
4-(2,4-Dichloro-phenoxy)-N-[4-(1-hydroxy-1-methyl-ethyl)-cyclohexyl]butyramide;
5-{[4-(2,4-Dichloro-phenoxy)-butyryl]-methyl-amino}-bi-cyclo[2.2.1]heptane-2-carboxylic acid ethyl ester;
4-(2,4-Dichloro-phenoxy)-N-[5-(1-hydroxy-1-methyl-ethyl)-adamantan-2-yl]-N-methyl-butyramide;
4-(2,4-Dichloro-phenoxy)-N-[5-(1-hydroxy-1-methyl-ethyl)-adamantan-2-yl]-N-methylbutyramide;
4-(2,4-Dichloro-phenoxy)-N-[5-(1-hydroxy-1-methyl-ethyl)-adamantan-2-yl]butyramide;
4-(2,4-Dichloro-phenoxy)-N-(5-hydroxymethyl-adamantan-2-yl)-N-methyl-butyramide;
N-(5-Hydroxy-adamantan-2-yl)-4-(4-methanesulfonyl-phenoxy)-butyramide
N-(5-Hydroxy-adamantan-2-yl)-4-(pyridin-2-yloxy)-butyramide;
N-(5-Hydroxy-adamantan-2-yl)-4-(pyridin-2-yloxy)-butyramide;
N-(5-Hydroxy-adamantan-2-yl)-4-(6-methyl-pyridazin-3-yloxy)-butyramide;
N-(5-Hydroxy-adamantan-2-yl)-4-(6-methyl-pyridazin-3-yloxy)-butyramide;
4-(2,4-Dichloro-phenoxy)-N-(4-methane-sulfonyl-cyclohexyl)-N-methyl-butyramide;
4-(2,4-Dichloro-phenoxy)-N-(4-methane-sulfonyl-cyclohexyl)-N-methyl-butyramide;
4-(2,4-Dichloro-phenoxy)-N-(5-hydroxy-methyl-bicyclo[2.2.2]oct-2-yl)-N-methyl-butyramide;
4-(2,4-Dichloro-phenoxy)-N-((1R,3S,5R,7S)-3-hydroxy-adamantan-1-yl)-butyramide; or
a salt thereof with a pharmaceutically acceptable acid or base, or any optical isomer or mixture of optical isomers, including a racemic mixture, or any tautomeric forms.

25. The compound according to any of the clauses 1-24, which is an agent useful for the treatment of conditions, disorders, or diseases wherein a modulation or an inhibition of the activity of 11βHSD1 is beneficial.

26. The compound according to clause 25, wherein the conditions, disorders, and diseases are influenced by intracellular glucocorticoid levels.

27. The compound according to clause 25 wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), progression from IGT to type 2 diabetes, progression of metabolic syndrome into type 2 diabetes, diabetic late complications, neurodegenerative and psychiatric disorders, and the adverse effects of glucocorticoid receptor agonist treatment or therapy.

28. A pharmaceutical composition comprising, as an active ingredient, at least one compound according to any one of the clauses 1-24 together with one or more pharmaceutically acceptable carriers or excipients.

29. The use of a compound according to any of clauses 1-24, for the preparation of a pharmaceutical composition for the treatment of conditions, disorders, or diseases wherein a modulation or an inhibition of the activity of 11βHSD1 is beneficial.

30. The use according to clause 29, wherein the conditions, disorders and diseases are influenced by intracellular glucocorticoid levels.

31. The use according to clause 29, wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), the progression from IGT to type 2 diabetes, the progression of the metabolic syndrome into type 2 diabetes, diabetic late complications, neurodegenerative and psychiatric disorders, and the adverse effects of glucocorticoid receptor agonist treatment or therapy.

32. A method for the treatment of conditions, disorders, or diseases wherein a modulation or an inhibition of the activity of 11βHSD1 is beneficial, the method comprising administering to a subject in need thereof an effective amount of a compound according to any of clauses 1-24.

33. The method according to clause 32, wherein the conditions, disorders, and diseases are influenced by intracellular glucocorticoid levels.

34. The method according to clause 32 wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), progression from IGT to type 2 diabetes, progression of metabolic syndrome into type 2 diabetes, diabetic late complications, neurodegenerative and psychiatric disorders, and the adverse effects of glucocorticoid receptor agonist treatment or therapy.

What is claimed is:

1. A compound selected from the group consisting of:
N-cyclopropyl-4-(2,4-dichloro-phenoxy)-N-(5-hydroxy-adamantan-2-yl)-butyramide;
4-(2,4-dichloro-phenoxy)-N-(5-hydroxy-adamantan-2-yl)-butyramide;
4-(2,4-dichloro-phenoxy)-N-(5-hydroxy-adamantan-2-yl)-N-methyl-butyramide;
4-(2,4-dichloro-phenoxy)-N-ethyl-N-(5-hydroxy-adamantan-2-yl)-butyramide;
4-(2,4-dichloro-phenoxy)-N-(5-hydroxy-methyl-adamantan-2-yl)-butyramide;
4-(2,4-dichloro-phenoxy)-N-(5-hydroxy-adamantan-2-yl)-N-isopropyl-butyramide;
4-(2,4-dichloro-phenoxy)-N-(5-hydroxy-methyl-adamantan-2-yl)-N-methyl-butyramide;
4-(2,4-dichloro-phenoxy)-N-(5-hydroxy-adamantan-2-yl)-2,2-dimethyl-butyramide;
4-(2,4-dichloro-phenoxy)-N-(5-hydroxy-adamantan-2-yl)-2,2,N-trimethyl-butyramide;
and 4-(2,4-dichloro-phenoxy)-N-(5-hydroxy-methyl-adamantan-2-yl)-2,2-dimethyl-butyramide;
or a pharmaceutically acceptable salt thereof.

2. 4-(2,4-Dichloro-phenoxy)-N-(5-hydroxy-adamantan-2-yl)-butyramide, or a pharmaceutically acceptable salt thereof.

3. 4-(2,4-Dichloro-phenoxy)-N-(5-hydroxy-methyl-adamantan-2-yl)-butyramide, or a pharmaceutically acceptable salt thereof.

4. A pharmaceutical composition comprising a compound of claim 1 and a pharmaceutically acceptable carrier or excipient.

5. A pharmaceutical composition comprising a compound of claim 2 and a pharmaceutically acceptable carrier or excipient.

6. A pharmaceutical composition comprising a compound of claim 3 and a pharmaceutically acceptable carrier or excipient.

* * * * *